United States Patent [19]
Labrie et al.

[11] Patent Number: 5,686,465
[45] Date of Patent: Nov. 11, 1997

[54] SEX STEROID ACTIVITY INHIBITORS

[75] Inventors: Fernand Labrie; Yves Merand, both of Quebec, Canada

[73] Assignee: Endorecherche Inc., Quebec, Canada

[21] Appl. No.: 485,739

[22] Filed: Jun. 7, 1995

Related U.S. Application Data

[62] Division of Ser. No. 285,354, Aug. 3, 1994, which is a division of Ser. No. 801,704, Dec. 2, 1991, Pat. No. 5,395,842, which is a continuation-in-part of Ser. No. 377,010, Jul. 7, 1989, abandoned, and Ser. No. 265,150, Oct. 31, 1988, abandoned.

[51] Int. Cl.$^6$ .................. A61K 31/43; A61K 31/54; A61K 31/545; A61K 31/445

[52] U.S. Cl. ............... 514/320; 514/196; 514/211; 514/222.2; 514/200; 514/319; 514/321; 514/324; 514/326; 514/358; 514/510; 514/456; 546/202; 546/456

[58] Field of Search ............... 514/456, 320, 514/319, 358, 211, 510, 222.2, 186, 321, 324, 326; 546/456, 205

[56] References Cited

U.S. PATENT DOCUMENTS

| | | | |
|---|---|---|---|
| 2,875,199 | 2/1959 | Cella | 260/239.57 |
| 3,321,483 | 5/1967 | Crenshaw et al. | 260/293.4 |
| 3,396,169 | 8/1968 | Lednicer et al. | 260/293.4 |
| 3,471,520 | 10/1969 | Irmscher et al. | 260/345.2 |
| 3,597,431 | 8/1971 | Coppola et al. | 260/288 |
| 3,995,060 | 11/1976 | Neri | 424/324 |
| 4,094,994 | 6/1978 | Schonenberger | 42/341 |
| 4,139,638 | 2/1979 | Neri | 424/324 |
| 4,161,540 | 7/1979 | Neri | 424/324 |
| 4,368,080 | 1/1983 | Crossley | 424/209 |
| 4,472,382 | 9/1984 | Labrie | 424/177 |
| 4,659,516 | 4/1987 | Bowler | 514/15 |
| 4,659,695 | 4/1987 | Labrie | 514/510 |
| 4,732,912 | 3/1988 | Pilgrim | 514/510 |
| 4,751,240 | 6/1988 | Bowler | 514/510 |
| 4,760,061 | 7/1988 | Edwards | 514/211 |
| 4,904,661 | 2/1990 | Pilgrim et al. | 514/510 |
| 4,950,684 | 8/1990 | Koszyk et al. | 514/456 |
| 4,963,568 | 10/1990 | Schoenleber et al. | 514/320 |
| 4,975,455 | 12/1990 | Brion et al. | 514/456 |
| 5,021,432 | 6/1991 | Yamanaka et al. | 514/337 |
| 5,098,903 | 3/1992 | Magarian et al. | 514/255 |
| 5,204,337 | 4/1993 | Labrie et al. | 514/182 |
| 5,407,947 | 4/1995 | Bryant et al. | 514/320 |

FOREIGN PATENT DOCUMENTS

| | | |
|---|---|---|
| 124369 | 4/1984 | European Pat. Off. . |
| 138504 | 4/1985 | European Pat. Off. . |
| 160508 | 4/1985 | European Pat. Off. . |
| 163416 | 4/1985 | European Pat. Off. . |
| 166509 | 4/1985 | European Pat. Off. . |
| 280618 | 2/1988 | European Pat. Off. . |
| 305242 | 7/1988 | European Pat. Off. . |
| 367576 | 10/1989 | European Pat. Off. . |
| 470310 | 2/1992 | European Pat. Off. . |
| 0652006 | 5/1995 | European Pat. Off. . |
| 2528434 | 6/1982 | France . |
| 3242894 | 11/1982 | Germany . |
| 3821148 | 12/1990 | Germany . |
| 8601105 | 2/1986 | WIPO . |
| 9010462 | 9/1990 | WIPO . |
| 9117749 | 5/1991 | WIPO . |
| 9221669 | 12/1992 | WIPO . |
| 9310741 | 6/1993 | WIPO . |

OTHER PUBLICATIONS

Jones et al., *Journal of Medicinal Chemistry*, vol. 22, No. 8 (1979).
Dhar, et al., *Contraception*, vol. 44, No. 4, (1991) pp. 461–472.
Stoessel, et al., *Journal of Steroid Biochem.*, vol. 25, No. 5A (1986) pp. 677–682.
Crenshaw, et al., *Journal of Medicinal Chemistry*, vol. 14, No. 2 (1971) pp.1185–1190.
Pruitt, et al., *Organic Prep. and Proc. Int'l.* vol. 22, No. 2 (1990) pp. 235–244.
CA:113(23)—No. 211775W p. 744, Dec. 1990—Sharma, et al.
CA:117(9)—No. 90146p p. 90147, Sep. 1992—Kapil, et al.
CA:86(1)—No. 5271Z p. 5280, Jan. 1977—Badran, et al.
CA:107—No. 154111(b) p. 678, Oct. 1987—Alberola, et al.
Asselin, et al., *J. Steroid Biochem.* 9:1079–1081 (1978).
Auchus, et al., *Biochemistry* 25:7295–7300 (1986).
Bhatnagar, et al., *J. Biol. Chem.* 253:811–815 (1978).
Blickenstaff, et al., *Steroids* 46:889–902 (1985).
Bucourt, et al., *J. Biol. Chem.* 253:8221–8228 (1978).
Chin, et al., *J. Biol. Chem.* 250:7682–7686 (1975).
Chin, et al., *J. Biol. Chem.* 255:3660–3664 (1980).
Durani, et al., *J. Med. Chem.* 32:1700–1707 (1989).
Furr, et al., *J. Endocr.* 113:R7–R9 (1987).
Jordan, et al., *Endocrinology* 124:1717–1726 (1989).
Klijn, et al., *J. Steroid Biochem.* 20(6B):1381, No. A33 (Abstr.) (1984).

(List continued on next page.)

*Primary Examiner*—Theodore J. Criares
*Attorney, Agent, or Firm*—Ostrolenk, Faber, Gerb & Soffen, LLP

[57] ABSTRACT

Inhibitors of sex steroid activity, for example those having the general structure

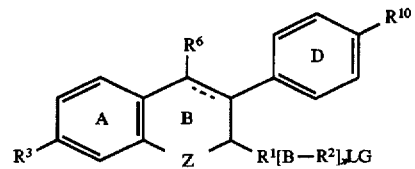

may be used as part of a pharmaceutical composition to provide antiestrogenic effects and/or to suppress estrogen synthesis. Such pharmaceutical compositions are useful for the treatment of breast cancer or other diseases whose progress is aided by activation of sex steroid receptors.

5 Claims, 5 Drawing Sheets

OTHER PUBLICATIONS

Poulin, et al., *Cancer Res.* 46:4933–4937 (1986).
Saeed, et al., *J. Med. Chem.* 33:3210–3216 (1990).
Sharma, et al., *J. Med. Chem.* 33:3216–3229 (1990).
Simard, et al., *Mol. Cell. Endo.* 39:141–144 (1985).
Simard, et al., *Mol. Cell. Endo.* 2:775–784 (1988).
Simard, et al., *Endocrinology* 126:3223–3231 (1990).
Thomas, et al., *J. Biol. Chem.* 258:1587–1590 (1983).
Thomas et al., *J. Biol. Chem.* 258:11500–11508 (1983).
Tobias, et al., *J. Biol. Chem.* 257:2783–2786 (1982).
von Angerer, et al., *J. Med. Chem.* 33:2635–2640 (1990).
von Angerer, et al., *J. Med. Chem.* 27:1439–1447 (1984).
Wakeling, et al., *Cancer Res.* 51:3867–3873.
Wakeling, et al., *J. Endo.* 112:R7–R10 (1987).
Wakeling, et al., *Steroid Biochem.* 30:141–147 (1988).

SEX STEROID ACTIVITY INHIBITORS

RELATED APPLICATIONS

This application is a divisional of U.S. patent application Ser. No. 08/285,354, pending, filed Aug. 3, 1994, which is in turn a divisional of U.S. patent application Ser. No. 07/801,704, filed Dec. 2, 1991, now U.S. Pat. No. 5,395,842, which is, in turn, a continuation-in-part of both U.S. patent application Ser. No. 07/377,010, filed Jul. 7, 1989, now abandoned and U.S. patent application Ser. No. 07/265,150, filed Oct. 31, 1988, now abandoned.

BACKGROUND OF THE INVENTION

This invention relates to novel inhibitors of sex steroid activity such as antiestrogen compounds having effective antagonistic capability while substantially lacking agonistic effects. More particularly, certain preferred embodiments of the invention relate to certain estradiol and diphenylethylene analogs which have high affinity for estrogen receptors but do not activate such receptors and/or which inhibit the production of sex steroids or their precursors.

During the treatment of certain sex steroid-dependent diseases, it is important to greatly reduce or, if possible, eliminate certain sex steroid-induced effects. For this purpose, it is desirable both to block receptor sites stimulated by sex steroids and also to reduce the amount of sex steroid available to act at these sites. For example, alternative or concurrent therapy to administration of antiestrogens could involve attempts to block the production of estrogens (e.g. by ovariectomy) such that less is available to activate receptor sites. However, prior art methods for blocking estrogen production insufficiently inhibit estrogen-induced functions. Indeed, it is possible that even in the total absence of sex steroid, some receptors may be activated. See Simard and Labrie, "Keoxifene shows pure antiestrogenic activity in pituitary gonadotrophs", Mol. Cell. Endocrinol. 39: 141–144, (1985), especially page 144.

Hence, antagonists of sex steroids may produce greater therapeutic results than therapy which only inhibits sex steroid production. Prior art antagonists, however, often have insufficient affinity for receptors, and some, although capable of binding the receptors, may themselves act as agonists and undesirably activate the very receptors they are intended to shield from activation.

There is, therefore, a need in the art for antiestrogens which effectively block estrogen receptors with minimal or no agonistic effect. In Wakeling and Bowler, "Steroidal Pure Antioestrogens", J. Endocrinol. 112: R7–R10 (1987), a steroid derivative is said to act as an antiestrogen but to exhibit some estrogen activity. The net effectiveness of a compound is effected by both its agonistic (undesirable) and antagonistic (desirable) activities.

In U.S. Pat. No. 4,094,994, it is disclosed that the use of certain antiestrogens may inhibit certain human breast tumor cells.

H. Mouridsen et al., Cancer Treatm. Rev. 5: 131–141 (1978), discloses that Tamoxifen, an antiestrogen, is effective in remission of advanced breast cancer in about 30 percent of the women patients treated.

The combined use of the antiestrogen Tamoxifen and a luteinizing hormone-releasing hormone agonist, Buserelin, is also known for treatment of breast cancer. See, for instance, Klijn et al. J. Steroid Biochem. 420: no. 6B, 1381 (1984). The objective remission of such cancers, however, remains unacceptably low.

It has been found that certain 7α-substituted derivatives of estradiol, for example a 7α-$(CH_2)_{10}$CONMeBu substitution possess antiestrogenic activity (Bowler et al., 1985; Eur. Patent Application 0138504; Wakeling and Bowler, J. Steroid Biochem. 30: 141–147 (1988). See also U.S. Pat. No. 4,659,516. The substitution $(CH_2)_9SOC_5H_6F_5$ has also been used on certain compounds (Wakeling et al., Cancer Res. 51: 3867–3873, 1991).

Certain —$(CH_2)_{10}$CONMeBu substituted compounds are also disclosed in U.S. Pat. No. 4,732,912 (See e.g. example 5 and 16). See also EP Pat. No. 166 509, EP Pat No. 124 369, EP Pat. No. 160 508, EP Pat. No. 163 416, U.S. Pat. No. 4,760,061, U.S. Pat. No. 4,751,240 and Wakeling A. E. and Bowler, J., J. Endocrinol. 112: R7–R10 (1987).

Estradiol derivatives bearing a carboxyalkyl substituent at the 7α-position maintained their affinity for the estrogen receptor when linked via their carboxy group to agarose or polyacrylamide resin for affinity chromatography purification of the estrogen receptor (Bucourt et al., J. Biol. Chem. 253: 8221, 1978).

Some steroid derivatives, such as 16-methylene estradiol and 16-methylene estrone, have been described as inhibitors of 17β-hydroxysteroid dehydrogenase activity (Thomas et al., J. Biol. Chem. 258: 11500, 1983).

Certain nonsteroidal compounds which are stated to have antiandrogenic effect are described by Furr et al., J. Endocrinol. 113: R7–R9 (1987).

U.S. Pat. No. 4,659,695 relates to a method of treatment of prostate cancer for susceptible male animals including humans whose testicular hormonal secretions are blocked by surgical or chemical means, e.g., by use of an LHRH agonist, e.g., [D-Trp$^6$, des-Gly-NH$_2^{10}$]LHRH ethylamide. The treatment includes administering an antiandrogen, e.g., flutamide in association with at least one inhibitor of sex steroid biosynthesis, e.g., aminoglutethimide and/or ketoconazole. See also U.S. Pat. No. 85/01454 (International Publication Number WO 86/01105) regarding combination therapy for treating hormonal-dependent cancers.

U.S. Pat. No. 4,472,382 relates to a method of treating prostate cancer using the combination of an antiandrogen and an LHRH agonist.

In U.S. Pat. No. 4,386,080 relates to new amide derivatives, and more particularly to novel acylanilides, possessing antiandrogenic properties.

In French Patent 2528434 and in Jordan and Koch, "Regulation of Prolactin Synthesis in vitro by estrogenic and antiestrogenic derivatives of estradiol and Estrone", Endocrinology 124(4): 1717–1725 (1989), antiestrogenic effects are described for certain 11β-substituted estradiol derivatives.

In U.S. Pat. No. 3,995,060, U.S. Pat. No. 4,161,540 and U.S. Pat. No. 4,139,638, it is disclosed that certain 4'-substituted and 3'-,4'-disubstituted anilides have antiandrogenic properties.

For a number of years, researchers have attempted to develop compounds which can efficiently inhibit androgen and/or estrogen formation without causing adverse effects to healthy tissues. More particularly, the inhibition of 17β-hydroxysteroid dehydrogenase, which is involved in the biosynthesis of testosterone, androst-5-ene-3β,17β-diol and estradiol, has been studied by some workers. Some affinity-label inhibitors for human placental estradiol 17β-dehydrogenase have been described (C. C. Chin and J. C. Warren, J. Biol. Chem. 250: 7682–7686, 1975; Y. M. Bhatnagar et al, J. Biol. Chem. 253: 811–815, 1978; C. C. Chin et al., J. Biol. Chem. 255: 3660–3664, 1980; J. L. Thomas and R. C. Strickler, J. Biol. Chem. 258: 1587–1590, 1983).

B. Tobias et al, J. Biol. Chem. 257: 2783–2786 (1982) and R. J. Auchus and D. F. Covey, Biochemistry 25: 7295–7300 (1986) disclose, respectively, the use of 17β-propynyl-substituted progestins and propynyl-substituted 3-hydroxy-14,15-secoestra-1,3,5(10)-trien-17-one as inhibitors of the 17β-estradiol dehydrogenase.

Thomas J. L. et al., J. Biol. Chem. 258: 11500 (1983) have described that 16-methylene estradiol and 16-methylene estrone are inhibitors of 17β-hydroxysteroid dehydrogenase activity.

Prior art methods have not been completely effective in inhibiting sex steroid synthesis while avoiding undesirable side effects.

Von Angerer et al. discuss other antiestrogens in "1-(aminoalkyl)-2-phenylindoles as Novel Pure Estrogen Antagonists", J. Med. Chem. 1990; 33: 2635–2640. In U.S. Pat. No. 4,094,994, where it is said that the use of certain antiestrogens inhibit certain human breast tumor cells. See also DE 3821148.

A. Saeed et al., J. Med. Chem. 33: 3210–3216, 1990; A. P. Sharma et al., J. Med. Chem. 33: 3216–3222 and 3222–3229 (1990) described the synthesis and biological activities of 2,3-diaryl-2H-1-benzopyrans analogs as antiestrogens having the following molecular structure:

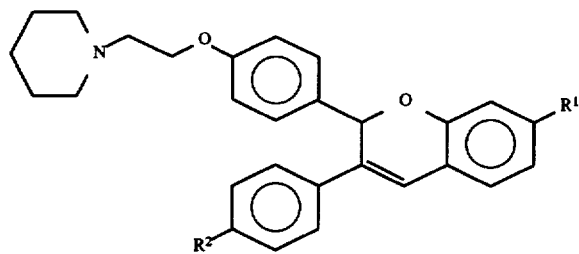

N. Durani et al., J. Med. Chem. 32: 1700–1707 (1989) describe the synthesis and biological activities of benzofuran and triarylfuran analogues as antiestrogens.

The European counterpart of priority applications 07/377,010 and 07/265,150 was published on May 9, 1990 as European Application No 0367576. The European Search report for that case disclosed the following publications:

In E.P. Patent No 305 242, Nique et al relates to the synthesis and the use of 17-acyl steroids as drugs. The Search Report emphasized page 7, compound I'C.

In E.P. Patent No 280 618, Nique et al. relates to 7-substituted 19-nor-steroids for drugs. The Search Report emphasized Examples 2, 3, pages 22, 23 and the claims.

In D.E. Patent No 32 42 894 A1, Neef et al relates to 17or-substituted equilenin for inhibition of progesterone biosynthesis and control of the fertility.

In U.S. Pat. No 2,875,199, Cella, J. A. discuss 17-carboxylated estradiols for decreasing the serum concentration of cholesterol.

Blickenstaff et al. (Steroids, Vol. 46, No 4 et 5, pages 889–902) described the synthesis of 16 and 17-substituted estradiols suitable for coupling to vinblastine species.

Other Search Report References were previously discussed herein.

OBJECTS OF THE INVENTION

It is an object of the present invention to provide methods of inhibiting sex steroid activity. Such methods may be useful in the treatment of sex steroid-related diseases.

It is another object of the invention to provide a pure antiestrogen for therapeutic use.

It is another object of the invention to provide compositions capable of inhibiting sex steroid synthesis, especially estrogen synthesis.

It is another object to provide an antiestrogen having good affinity for estrogen receptors, but substantially lacking undesirable agonistic activity regarding these receptors and substantially lacking hormonal activity.

It is another object of the invention to provide a therapeutic antiestrogenic composition useful in the treatment of estrogen-related diseases. These diseases include, but are not limited to breast cancer, uterine cancer, ovarian cancer, endometriosis, uterine fibroma, precocious puberty and benign prostatic hyperplasia.

It is another object of the invention to provide inhibitors of sex steroid activity useful in the treatment of both estrogen- and androgen-related diseases. Androgen-related diseases include but are not limited to prostate cancer, acne vulgaris, hirsutism, precocious puberty, benign prostatic hyperplasia, seborrhea, androgenic alopecia and sexual deviants. Control of androgen activity may also be useful in male contraception.

SUMMARY OF THE INVENTION

In accordance with the invention, a pharmaceutical composition is provided comprising a therapeutically effective amount of the diphenylethylene derivatives specified herein. One embodiment of the diphenylethyl framework is illustrated below:

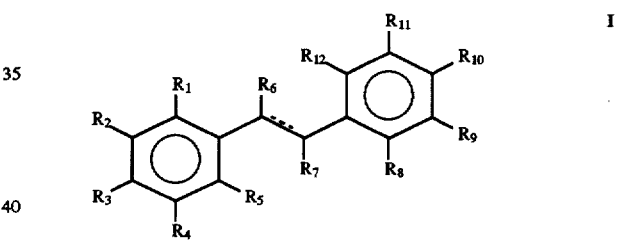

where the dotted line represents an optional double bond of Z or E configuration. Certain preferred substituents include, but are not limited to the following:

$R_1$, $R_5$, $R_8$, and $R_{12}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitro, nitrile and nitroso.

$R_2$, $R_4$, $R_9$ and $R_{11}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitrile, nitro, nitroso, azido, ($C_1$–$C_7$) alkanoyl mercuryl, lower alkylamino, dilower alkylamino, $AXR_{21}$, $Y_7$—$A^1$[$Y$—$A^{11}$]$_u$ —$XR_{21}$, and $A^1$[$Y$—$A^{11}$]$_u$—$XR_{21}$ wherein:

A is straight- or branched-chain ($C_1$–$C_{30}$) alkylene, ($C_2$–$C_{30}$) alkenylene, ($C_2$–$C_{30}$) alkynylene or fluoro-substituted analogs of the foregoing; wherein u is an integer from 0 to 5; wherein $Y_7$ is absent or selected from the group consisting of carbonyl and carboxyl. $A^1$ and $A^{11}$ may be the same or different and are independently either absent or selected from the group consisting of straight- or branched-chain alkylene, straight- or branched-chain alkynylene, straight- or branched-chain alkenylene, phenylene and fluoro-substituted analogs of the foregoing, wherein $A^1$ and $A^{11}$ together have a total of from 3 to 20 carbon atoms and Y is selected from the group consisting of —O—, —S—, —Se—, —SO—, —SO$_2$—, —CO—, —NR$_{22}$—, SiR$_{22}$R$_{22}$—, —CR$_{22}$OR$_{22}$—, —NR$_{22}$CO—, —NR$_{22}$CS—, —CONR$_{22}$—, —COO—, —COS—, —SCO—, —CSS—, —SCS—, —OCO— and phenylene ($R_{22}$ being hydrogen or lower alkyl), wherein $R_{21}$ is selected from the group consisting of hydrogen, straight- or branched-chain lower alkyl, lower alkenyl or lower alkynyl, ($C_3$–$C_7$) cycloalkyl, halogeno(lower) alkyl, carboxy(lower)alkyl, (lower)alkoxycarbonyl (lower)alkyl, ($C_6$–$C_{10}$) aryl, ($C_6$–$C_{10}$) arylalkyl, di(lower)alkylamino(lower)alkyl and fluoro-substituted analogs of the foregoing, and wherein X is selected from the group consisting of —CONR$_{23}$—, —CSNR$_{23}$—, —NR$_{24}$CO—, —NR$_{24}$CS—, —NR$_{24}$CONR$_{23}$—, —NR$_{24}$—C(NR$_{25}$)—NR$_{23}$, —SO$_2$NR$_{23}$—, —CO—, —CSS—, —SCS—, —O—, —NR$_{23}$—, —(NO)R$_{23}$—, —(PO)R$_{23}$—, —NR$_{24}$COO—, —NR$_{24}$SO$_2$—, —S—, —SO— and —SO$_2$— ($R_{23}$ being selected from the group consisting of hydrogen, lower alkyl, a species which, together with $R_{21}$, forms a saturated or unsaturated heterocyclic ring having at least one nitrogen atom and in certain embodiments, at least one other heteroatom selected from the group consisting of oxygen, sulfur, silicon, selenium and nitrogen, and fluoro-substituted analogs of the foregoing; and $R_{24}$ being hydrogen or lower alkyl, and $R_{25}$ being hydrogen, nitrile or nitro). In certain preferred embodiments, $XR_{21}$ forms a tetrazole ring.

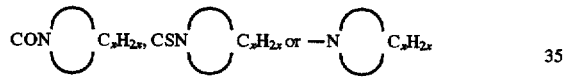

(where x is an integer from 4–6).

$R_3$ and $R_{10}$ are preferably independently selected from the group consisting of hydrogen, hydroxyl, halogen, lower alkyl, lower alkoxy, lower alkoxy carbonyloxy, carboxyl, ($C_1$–$C_{20}$) alkanoyloxy, ($C_3$–$C_{20}$) alkenoyloxy, ($C_3$–$C_{20}$) alkynoyloxy, ($C_7$–$C_{11}$) aroyloxy and alkylsilyloxy.

$R_6$ and $R_7$ are preferably independently selected from the group consisting of hydrogen, amino, lower alkylamino, dilower alkyl amino, nitro, nitrile, nitroso, halogen, lower alkyl, lower alkenyl, lower alkynyl, halogeno lower alkyl, halogeno lower alkenyl, halogeno lower alkynyl, alkyl sulfonyl, aryl sulfonyl, a substituted 5 to 7 member heterocyclic ring having at least one heteroatom (selected from oxygen, sulfur, silicon, selenium, nitrogen), —(CH$_2$)$_s$W (wherein W is nitrile, hydroxyl, azido, nitroso, alkoxy, nitro, thionitrile, halogen, alkyl sulfonyl or aryl sulfonyl and s is an integer from 1 to 6), a moiety of the formula:

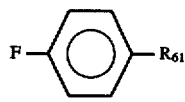

II wherein:

F is absent or selected from the group consisting of alkyl, carbonyl or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_6(CH_2)_nY_6$ ($X_6$ being selected from the group consisting of —O—, —S—, —Se—, —SO—, —SO$_2$— and —CO—, and $Y_6$ being selected from the group consisting of hydroxyl, amino, monoalkyl amino, dialkyl amino, dimethyl N-oxide, N-aziridyl, guanidine, N-pyrrolidino, N-piperidino, N-methylpiperazino, N-morpholino and alkoxy, and n being an integer from 1 to 6, preferably 3), $AXR_{21}$, $Y_7$—$A^1$—$[Y—A^{11}]_u$—$XR^{21}$, and $A^1$—$[Y—A^{11}]_u$—$XR^{21}$, wherein:

A is selected from the group consisting of straight- or branched-chain ($C_1$–$C_{30}$) alkylene, ($C_2$–$C_{30}$) alkenylene, ($C_2$–$C_{30}$) alkynylene and fluoro-substituted analogs of the foregoing, wherein u is an integer from 0 to 5, wherein $Y_7$ is absent or is selected from the group consisting of carbonyl, carboxyl, —CH$_2$S— and —CH$_2$O—, wherein $A^1$ and $A^{11}$ may be the same or different and may be absent or selected from the group consisting of straight- or branched-chain alkylene, straight- or branched-chain alkynylene, straight- or branched chain alkenylene, phenylene and fluoro-substituted analogs of the foregoing, wherein $A^1$ and $A^{11}$ together have a total of from 2 to 30 carbon atoms, wherein Y is selected from the group consisting of —O—, —S—, —Se—, —SO—, —SO$_2$—, —CO—, —NR$_{22}$—, —SiR$_{22}$ R$_{22}$—, —CR$_{22}$OR$_{22}$—; —NR$_{22}$CO—, —NR$_{22}$CS—, —CONR$_{22}$—, —CSNR$_{22}$—, —COO—, —COS—, —SCO—, —CSS—, —SCS—, —OCO— and phenylene ($R_{22}$ being hydrogen or lower alkyl), wherein $R_{21}$ is selected from the group consisting of hydrogen, straight or branched chain lower alkyl, lower alkenyl, lower alkynyl, ($C_3$–$C_7$) cycloalkyl, halogeno (lower) alkyl, carboxy(lower)alkyl, (lower)alkoxycarbonyl(lower) alkyl, ($C_6$–$C_{10}$)aryl, ($C_7$–$C_{11}$) arylalkyl, all(lower) alkylamino (lower) alkyl and fluoro-substituted analogs of the foregoing, wherein X is selected from the group consisting of —CONR$_{23}$—, —CSNR$_{23}$—, —NR$_{24}$CO—, —NR$_{24}$CS—, —NR$_{24}$CONR$_{23}$—, —NR$_{24}$—C(NR$_{25}$)—NR$_{23}$—, —SO$_2$NR$_{23}$—, —CO—, —CSS—, —SCS—, —O—, —NR$_{23}$—, —(NO)R$_{23}$—, —(PO)R$_{23}$—, —NR$_{24}$COO—, —NR$_{24}$SO$_2$—, —S—, —SO— and —SO$_2$— ($R_{23}$ being selected from the group consisting of hydrogen, lower alkyl and a species which, together with $R_{21}$, forms a saturated or unsaturated heterocyclic ring having at least one nitrogen atom and, in certain embodiments at least one other heteroatom selected from the group consisting of oxygen, sulfur, silicon, selenium and nitrogen, and fluoro-substituted analogs of the foregoing, $R_{24}$ being hydrogen or lower alkyl and $R_{25}$ being hydrogen, nitrile or nitro). In certain preferred embodiments, $XR_{21}$ forms a tetrazole ring.

$R_6$ and $R_7$ may also be a species which, in combination with another substituent of general molecular formula I, forms a moiety selected from the group consisting of: —CH$_2$—, —CHX—, —CX$_2$— (X being halogen, carboxyl or alkoxycarbonyl), —O—, —S—, —Se—, >N—CN, >NR$_{29}$ and >NCO$_2$R$_{29}$— ($R_{29}$ being hydroxy or lower alkyl), lower alkylene, —(CH$_2$)$_r$O(CH$_2$)s—, —(CH$_2$)$_r$S(CH$_2$)$_s$—, —(CH$_2$)$_r$Se(CH$_2$)$_s$—, —(CH$_2$)$_r$SO(CH$_2$)$_s$—, —(CH$_2$)$_r$SO$_2$(CH$_2$)$_s$—, (CH$_2$)$_r$CO(CH$_2$)$_s$—, —(CH$_2$)$_r$NR$_{22}$(CH$_2$)$_s$—, —(CH$_2$)$_r$SiR$_{22}$R$_{22}$(CH$_2$)$_s$— or —(CH$_2$)$_r$CR$_{22}$(CH$_2$)$_s$— ($R_{22}$ being hydrogen or lower alkyl, r and s being independent integers from 0 to 3), a moiety of the formula:

$$\underset{Z}{\overset{R_{71}}{\diagdown}}A^1-[Y-A^{11}]_u XR_{21} \qquad \text{III}$$

wherein $A^1$, Y, $A^{11}$, u, X and $R_{21}$ are as defined above, wherein Z is absent or is selected from the group consisting of lower alkylene, halogeno lower alkylene,—$(CH_2)_n O$—, —$(CH_2)_n S$—, —$(CH_2)_n Se$—, —$(CH_2)_n SO$—, —$(CH_2)_n SO_2$—, —$(CH_2)_n CO$—, —$(CH_2)_n NR_{22}$—, —$(CH_2)_n SiR_{22}R_{22}$— and —$(CH_2)_n CR_{22}OR_{22}$—, $R_{12}$ is as defined above, n being an integer from 0 to 3, and $R_{71}$ being selected from a group consisting of hydrogen, hydroxyl, halogen, lower alkyl, lower alkoxy and lower alkylsilyl, a moiety of the formula:

$$>N-A^1[Y,-A^{11}]_u-XR^{21} \qquad \text{IV}$$

wherein N is nitrogen atom and $A^1$, Y, $A^{11}$, u, X and $R_{21}$ are as defined above.

In preferred embodiments, moieties which are combinations of R groups from general structure I, are combinations of $R_6$ and $R_7$, $R_6$ with $R_1$ or $R_{12}$, or $R_7$ with $R_5$ or $R_8$.

The invention further provides an inhibitor of sex steroid activity having, as part of its molecular structure, a substituted or unsubstituted estrogenic nucleus of general formula V:

wherein $R^5$ and $R^6$ are hydrogen lower alkyl, alkoxy carbonyl, ($C_1$–$C_{20}$) alkanoyl, ($C_3$–$C_{20}$) alkenoyl, ($C_3$–$C_{20}$) alkynoyl, ($C_7$–$C_{11}$) aroyl and alkylsilyl, wherein dotted lines are optional pi bonds. In some embodiments, the optional pi bonds are not simultaneously present when aromaticity would result from such simultaneous presence; $R^{15}$ is either a direct bond from e to the number 5 carbon or a methylene or ethylene linkage to the number 5 carbon or a lower alkyl substituent, wherein e is selected from the group consisting of carbon, sulfur and nitrogen, q is absent or is a divalent methyl or ethyl moiety; said inhibitor further having a side chain of the formula —$R^1$[—B—$R^2$—]$_x$L—G wherein in at least one of said side chains is substituted at a position selected from the group consisting of carbon 2, carbon 4, carbon 5, carbon 10, carbon 11, carbon 13, q and e atom wherein:

x is an integer from 0 to 6, wherein at least one of L and G is a polar moiety distanced from the substitution point by at least three intervening atoms, and wherein:

$R^1$ and $R^2$ are independently either absent or selected from the group consisting of straight- or branched-chain alkylene, straight- or branched-chain alkynylene, straight- or branched-chain alkenylene, phenylene, and fluoro-substituted analogs of the foregoing;

B is either absent or selected from the group consisting of —O—, —S—, —Se—, —SO—, —SO$_2$—, —NR$^3$—, —SiR$^3$$_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene ($R^3$ being hydrogen or lower alkyl);

L is either a moiety which together with G, forms a heterocyclic ring having at least one nitrogen atom or is selected from the group consisting of lower alkyl, —CONR$_4$—, —CSNR$^4$—, —NR$^5$CO—, —NR$^5$CS—, —NR$^5$CONR$^4$—, —NR$^5$C(NR$^6$)—NR$^4$—, —SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— ($R^4$ and $R^5$ being independently selected from the group consisting of hydrogen and lower alkyl; and $R^6$ being selected from the group consisting of hydrogen, nitrile and nitro); and G is either a moiety which together with L forms a heterocyclic ring having at least one nitrogen atom or is selected from the group consisting of hydrogen, lower alkyl, lower alkenyl, lower alkynyl, ($C_3$–$C_7$) cycloalkyl, bromo (lower)alkyl, chloro(lower)alkyl, fluoro(lower)alkyl, iodo (lower)alkyl, cyano(lower)alkyl, carboxy(lower)alkyl, (lower)alkoxycarbonyl(lower)alkyl, ($C_6$–$C_{10}$) aryl, ($C_7$–$C_{11}$)arylalkyl, di(lower)alkylamino(lower)alkyl, fluoro-substituted analogs of the foregoing.

This invention further provides a pharmaceutical composition comprising a pharmaceutically acceptable diluent or carrier and a therapeutically effective amount of the foregoing sex steroid activity inhibitor.

The inhibitor is preferably hydroxy-substituted in at least the 3 or 12 positions, and is preferably substituted at the 7 position with a $C_1$–$C_4$ alkyl. Compounds of formula V above may be used, preferably as part of pharmaceutical compositions including acceptable diluents or carriers, to treat sex steroid dependent diseases by inhibiting sex steroid activity.

In another embodiment, the invention provides a pharmaceutical composition comprising a pharmaceutically acceptable diluent or carrier and a therapeutically effective amount of a sex steroid activity inhibitor having, as part of its molecular structure, an estrogenic nucleus of the formula:

wherein said sex steroid activity inhibitor includes, as another part of its molecular structure, a side chain of the formula $R^1$(B—$R^2$)$_x$LG substituted onto a ring carbon of said estrogenic nucleus to form:

wherein x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched-chain alkynylene, straight- or branched-chain alkenylene, phenylene, and fluoro-substituted analogs of the foregoing;

B is either absent or selected from the group consisting of —O—, —S—, —Se—, —SO—, —SO$_2$—, —NR$^{30}$—, —SiR$^{30}$$_2$—, —CR$^{30}$OR$^{30}$—, —NR$^3$CO—, —NR$^{30}$CS—, —CONR$^{30}$—, —CSNR$^{30}$—, —COO—, —COS—, —SCO—, —CSS—, —SCS—, —OCO— and phenylene ($R^{30}$ being hydrogen or lower alkyl);

L is either a moiety which together with G, forms a heterocyclic ring having at least one nitrogen atom or is selected from the group consisting of lower alkyl, —CONR⁴—, —CSNR⁴—, —NR⁵CO—, —NR⁵CS—, —NR⁵CONR⁴—, —NR⁵C(NR⁶⁰)NR⁴—, —SO₂NR⁴—, —CSS—, —SCS—, —(NO)R⁴—, —(PO)R⁴—, —NR⁵COO—, —NR⁵COO—, —NR⁵SO₂—, —O—, —NR⁴—, —S—, —SO—, and —SO₂— ($R^4$ and $R^5$ being independently selected from the group consisting of hydrogen and lower alkyl; and $R^{60}$ being selected from the group consisting of hydrogen, nitrile and nitro);

G is either a moiety which together with L forms a heterocyclic ring having at least one nitrogen atom or is selected from the group consisting of hydrogen, lower alkyl, lower alkenyl, lower alkynyl, ($C_3$–$C_7$)cycloalkyl, bromo (lower)alkyl, chloro(lower)alkyl, fluoro(lower)alkyl, iodo (lower)alkyl, cyano(lower)alkyl, carboxy(lower)alkyl, (lower)alkoxycarbonyl(lower)alkyl, ($C_6$–$C_{10}$)aryl, ($C_7$–$C_{11}$)arylalkyl, di(lower)alkylamino(lower)alkyl, and fluoro-substituted analogs of the foregoing;

wherein Z is selected from the group consisting of lower alkylene, halogeno lower alkylene, —(CH₂)ₙO—, —(CH₂)ₙS—, —(CH₂)ₙSe—, —(CH₂)ₙSO—, —(CH₂)ₙSO₂—, —(CH₂)ₙCO—, —(CH₂)ₙNR₂₂—, —(CH₂)ₙSiR₂₂R₂₂— and —(CH₂)ₙCR₂₂OR₂₂ (wherein $R_{22}$ is hydrogen or lower alkyl and n is an integer from 0 to 3);

wherein $R^3$ and $R^{10}$ are independently selected from the group consisting of hydrogen, hydroxyl, halogen, lower alkyl, lower alkoxy, lower alkoxy carbonyloxy, carboxyl, ($C_1$–$C_{20}$) alkanoyloxy, ($C_3$–$C_{20}$) alkenoyloxy; ($C_3$–$C_{20}$) alkynoyloxy, OR'₃, and OR'₁₀, (wherein R'₃ and R'₁₀ are hydrogen, alkyl, ($C_1$–$C_{20}$) alkanoyl, ($C_3$–$C_{20}$) alkenoyl, ($C_3$–$C_{20}$) alkynoyl or ($C_7$–$C_{11}$) aroyl); and wherein $R^6$ is selected from the group consisting of hydrogen, lower alkyl, lower alkenyl and lower alkynyl.

when L and G are together a nitrogen hetero ring, such ring is preferably

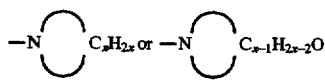

(where x is an integer from 4–6).

$R_6$ is preferably methyl, ethyl or propyl. Unsaturated analogs such as ethenyl or ethynyl may also be used. In some embodiments, at least one of the A and D rings is substituted with hydroxyl or a moiety converted in vivo to hydroxyl (e.g. hydrogen in positions 3 and 10, acetoxy, benzoyloxy, akanoyloxy, alkenoyloxy and aroyloxy). For example, $R^3$ and/or $R^{10}$ may be hydroxyl. The ring-closing moiety, Z, is preferably —O—, —S—, —NH— or —CH₂—, and in some embodiments is a bivalent moiety containing carbon, sulfur or nitrogen. Preferred side chains (e.g. $R^1$(B—$R^2$)ₓLG) are discussed in the detailed description and examples herein.

In another embodiment, the estrogenic nucleus may include a ring nitrogen onto which is substituted the side chain. Thus, the invention provides a pharmaceutical composition comprising a pharmaceutically acceptable carrier or diluent and a therapeutically effective amount of a compound of the formula:

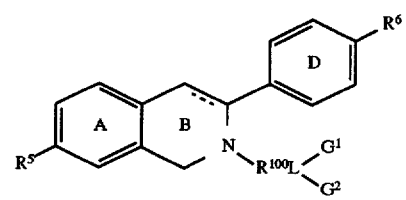

wherein the dotted line represents an optional double bond, wherein $R_5$ and $R_6$ are independently hydrogen, hydroxy or a moiety which is converted to hydroxy in vivo;

wherein $R^{100}$ is bivalent moiety which distances L from the B-ring by 4–10 intervening atoms;

wherein L is a bivalent or trivalent polar moiety selected from the group consisting of —CO—, —SO—, —CON<, —N< and —SON<;

wherein $G^1$ is either absent or selected from the group consisting of hydrogen, a $C_1$ to $C_5$ hydrocarbon, a substituted or unsubstituted $C_5$ to $C_7$ cycloalkyl, a bivalent moiety which joins $G^2$ and L to form a 5- to 7-membered heterocyclic ring, and halo-substituted derivatives of the foregoing; and wherein $G^2$ is either absent or selected from the group consisting of hydrogen, a $C_1$ to $C_5$ hydrocarbon, a substituted or unsubstituted bivalent moiety which joins $G^1$ and L to form a 5- to 7-membered heterocyclic ring and halo-substituted derivatives of the foregoing.

In another embodiment, the invention provides a pharmaceutical composition comprising a pharmaceutically acceptable carrier or diluent and a therapeutically effective amount of an estrogen activity inhibitor of the following formula:

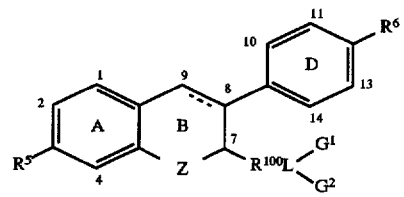

wherein the dotted line is an optional double bond;

wherein $R_5$ and $R_6$ are independently hydrogen, hydroxyl or a moiety which is converted to hydroxyl in vivo;

wherein Z is a bivalent ring closing moiety.

wherein $R^{100}$ is a bivalent moiety which distances L from the B-ring by 4–10 intervening atoms;

wherein L is a bivalent or trivalent polar moiety selected from the group consisting of —CO—, —SO—, —CON<, —N< and —SON<.

wherein $G^1$ is either absent or selected from the group consisting of hydrogen, a $C_1$ to $C_5$ hydrocarbon, a saturated or unsaturated $C_5$ to $C_7$ cycloalkyl, a bivalent moiety which joins $G^2$ and L to form a 5- to 7-membered heterocyclic ring, and halo-substituted derivatives of the foregoing;

wherein $G^2$ is either absent or selected from the group consisting of hydrogen, a $C_1$ to $C_5$ hydrocarbon, a substituted or unsubstituted $C_5$ to $C_7$ cycloalkyl, a bivalent moiety which joins $G^1$ and L to form a 5- to 7-membered heterocyclic ring and halo-substituted derivatives of the foregoing.

In one embodiment, Z includes a carbon, sulfur or nitrogen atom. In another embodiment, Z in —CH₂—, —NH—, —S— or —O—. In the side chain

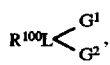

it is preferred that at least one of $G^1$ and $G^2$ has at least two carbon atoms. $G^1$ and $G^2$, in some embodiments, are independently absent or are selected from the group consisting of hydrogen, $C_1$ to $C_5$ hydrocarbon, a substituted or unsubstituted $C_5$ to $C_7$ cycloalkyl and halo-substituted derivatives of the foregoing. $R^{100}$, in some embodiments, is a straight or branched chain alkylene, alkenylene or alkynylene which distances L from the B ring by 4–10 intervening atoms. Unsaturation in $R^{100}$ may include, for example, phenylene or alkynylene. Preferred moieties for $R^{100}$ include but are not limited to $R^1(B—R^2)_x$ from the side chain $R^1(B—R^2)_x$ LG discussed above or $A'—(Y—A'')_u$ from the side chain $A'—(Y—A'')_uXR^{21}$ discussed above. Preferred side chains include but are not limited to —$(CH_2)_{10}CONCH_3C_4H_9$, —$(CH_2)_9SOC_5H_6F_5$, —$(CH_2)_6NC_5H_{10}$ and —$\emptyset$—$O(CH_2)_2NC_5H_{10}$. When $G^1$, $G^2$ and L combine to form a nitrogen-containing heterocyclic moiety, such moiety is preferably, but is not limited to,

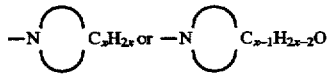

(where x is an integer from 5–7).

As used herein, the term "sex steroid activity inhibitor" includes any compound which suppresses the activity of sex steroids by any mechanism including, for example, inhibition of sex steroid synthesis or antagonistic blocking of sex steroid receptors. "Androgen activity inhibitors" and "estrogen activity inhibitors" are sex steroid inhibitors capable of inhibiting the activity of androgens and estrogens, respectively. For example, estrogen activity inhibitors include, but are not limited to antiestrogens which block estrogen receptors, thereby making them unavailable to estrogen compounds which could otherwise activate those receptors. Sex steroid activity inhibitors also include compounds which inhibit the formation of compounds capable of activating sex steroid receptors such as inhibitors of the production of natural sex steroids (e.q. 17β-estradiol) or inhibitors of production of precursors of natural sex steroids. One mechanism by which these sex steroid production inhibitors may operate is by blocking enzymes which catalyze production of natural sex steroids or their precursors (e.g. inhibitors of enzymes such as aromatase, 17β-hydroxysteroid dehydrogenase, 3β-hydroxysteroid dehydrogenase and the like).

As used herein, the term "estrogenic nucleus" includes any compound which, in the absence of the side chain substituent sped fled herein, is capable of acting as an estrogen as determined by a weight increase of at least 100 percent over a seven-day period of the uterus of ovariectomized rats treated with the compound in question (0.5 mg twice daily per 100 grams of body weight) versus a control group of ovariectomized rats. Treatment should start on the day of castration. The precise test, other than any parameters set forth in this paragraph, is that reported in Simard et al., Mol. Endocrinol. 2: 775–784 (1988).

The following conventions apply to structural formulae set forth herein. Unless specifically designated to the contrary, substituents may have either α or β stereochemistry or, where valence permits may represent one substituent in α position and another in β position. Presence of optional pi bonds are independent of each other. All structures include salts thereof. Atoms of any estrogenic nucleus for which no substituent is shown or described may optionally be substituted or unsubstituted so long as such substitution does not prevent the nucleus from functioning as an "estrogenic nucleus" as defined herein. Those atoms having a defined substituent may optionally be further substituted by other substituents where their valence permits such further substitution. As used herein, the term "lower", when describing a chemical moiety means a moiety having 8 or fewer atoms. For instance, a "lower alkyl" means a $C_1$ to $C_8$ alkyl. Any moiety of more than two atoms may be straight- or branched-chain unless otherwise specified.

BRIEF DESCRIPTION OF DRAWINGS

FIG. 5 shows the comparative inhibitory activity of various concentrations of EM 343 and EM 312 on the growth of human breast cancer ZR-75-1 cells stimulated by 17β-estradiol. The respective IC$_{50}$ values are calculated at $2.55 \times 10^{-10}$ M for EM 343 and $8.43 \times 10^{-10}$ for EM 312, thus indicating a 3-fold better activity for EM 343.

DETAILED DESCRIPTION OF THE PREFERRED EMBODIMENTS

Figure 1:
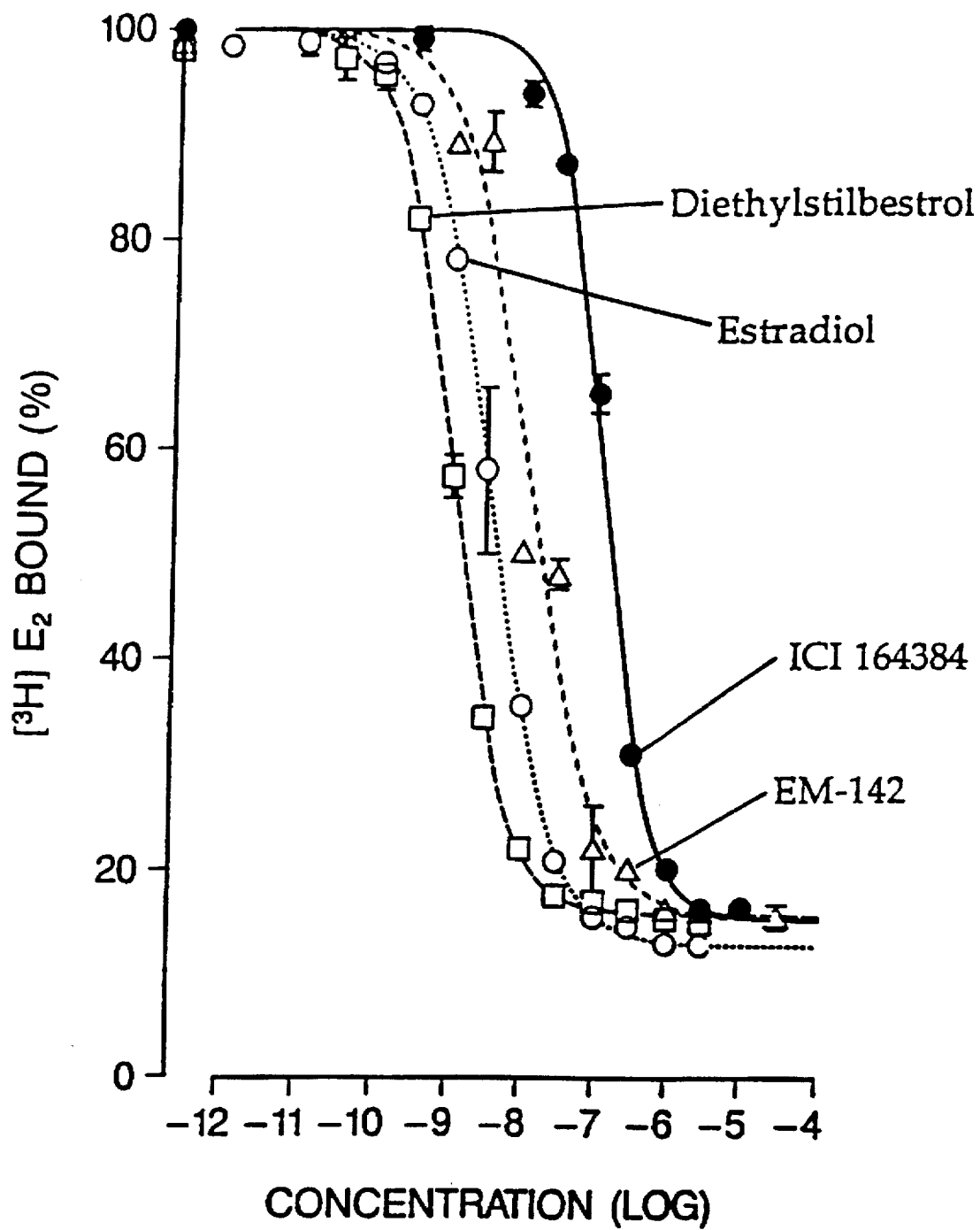
FIG. 1 illustrates a competition binding assay of the affinity of estradiol, diethylstilbestrol, ICI 164384 (Wakeling, A. E. and Bowler, L, 1987; J. Endocrinol. 112: R7–R110) and EM-142 (an antiestrogen having a nonsteroidal nucleus and synthesized in example 1, herein) for the rat uterine cytosol receptor (Asselin et al., 1978; J. Steroid Biochem. 9: 1079–1082).

In certain preferred embodiments of the invention, the R$_3$ and R$_{10}$ substituents on the nucleus of structure I supra are hydroxyl, (C$_1$–C$_{20}$) alkanoyloxy (C$_3$–C$_{20}$) alkenoyloxy, (C$_3$–C$_{20}$) alkynoyloxy, (C$_7$–C$_{10}$) aroyloxy and/or the R$_7$ substituent is A$^1$—[Y—A$^{11}$]u—X—R$_{21}$. It is also preferred that the R$_7$ substituent have between 7 and 20 carbon atoms. It is also preferred that R$_6$ of structure I, supra be lower alkyl, ethyl, fluoroethyl, or (CH$_2$)$_2$W, wherein W is a halogen or lower alkoxy, unsaturated lower alkenyl or alkynyl groups may also be used. In certain embodiments, therapeutic compositions may be comprise one or more compounds represented by Formula I. Preferably, at least one antiestrogenic compound is represented by the formula:

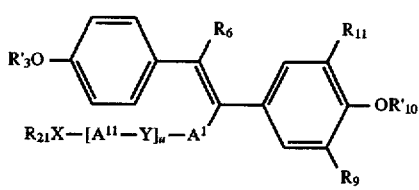

VI wherein $A^1$, $A^{11}$, Y, u, X and $R_{21}$ are defined as previously for $R_6$ and $R_7$ in the formula I, wherein the double bond is in trans configuration, wherein $R'_3$ and $R'_{10}$ are hydrogen, alkyl, $(C_1-C_{20})$ alkanoyl $(C_3-C_{20})$ alkenoyl, $(C_3-C_{26})$ alkynoyl or $(C_7-C_{11})$ aroyl, wherein $R_6$ is preferably selected from the group consisting of hydrogen, nitro, nitrile, halogen, lower alkyl, lower alkynyl, halogeno lower alkyl, halogeno lower alkenyl, halogeno lower alkynyl, alkyl sulfonyl, aryl sulfonyl, a substituted 5 to 7 member heterocyclic ring having at least one hetero atom (selected from oxygen, sulfur, silicon, selenium, nitrogen), $-(CH_2)_sW$ (wherein W is nitrile, hydroxyl, azido, nitroso, alkoxy, nitro, thionitrile, halogen, alkyl sulfonyl, aryl sulfonyl and s is an integer from 1 to 6), or has the formula:

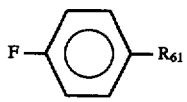

wherein:

F is present or selected from the group consisting of alkyl, carbonyl or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_6(CH_2)_nY_6$, wherein $X_6$ is selected from the group consisting $-O-$, $-S-$, $-Se-$, $-SO-$, $-SO_2-$ and $-CO-$ and $Y_6$ is selected from the group consisting hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n is an integer from 1 to 6 preferable 3.

$R_9$ and $R_{11}$ are preferably independently selected from the group consisting of hydrogen, hydroxyl, halogen, lower alkyl, lower alkoxy, lower alkylsilyl, amino, nitrile, nitro, nitroso, azido, lower alkylamino, dilower alkylamino, $AXR_{21}$ and $A^1[Y-A^{11}]u-X-R_{21}$, wherein A, $A^1$, $A^{11}$, Y, X, $R_{21}$ and u are as defined previously from $R_6$ and $R_7$.

When administered systemically, pharmaceuticals of the inventions may be used in the treatment of breast cancer, uterine cancer, ovarian cancer, endometriosis, uterine fibroma, precocious puberty and benign prostatic hyperplasia.

When sex steroid activity inhibitors are administered in accordance with the invention, they are preferably administered at a dosage from about 1 mg to about 2000 mg of active expedient (e.g. sex steroid activity inhibitor), per day per 50 kg of body weight, most preferably from about 10 mg to about 100 mg per day per 50 kg of body weight.

Pharmaceutical compositions comprise therapeutically effective amounts of one or more of the sex steroid activity inhibitors (including antiestrogens) discussed herein wherein a pharmaceutically acceptable diluent or carrier is included with the active compound(s). The diluent or carrier will vary in accordance with known techniques depending upon the manner in which the pharmaceutical composition is to be administered.

A composition suitable for oral administration may preferably include at least one inhibitor of sex steroid activity wherein the total concentration of all such inhibitors in said pharmaceutical composition is from about 1% to about 95% of the composition (by weight), and preferably from about 5% to about 20%. The composition preferably further includes a pharmaceutically acceptable diluent, for example, starch or lactose with or without tartrazine.

When prepared for parenteral injection, an inhibitor of sex steroid activity is preferably added at a concentration between about 1 mg/ml and about 100 mg/ml (preferably about 2 mg/ml to about 10 mg/ml) into a carrier preferably selected from the group consisting of saline, water, aqueous ethanol, aqueous dimethylsulfoxide and oil.

A composition suitable for parenteral administration preferably contains a carrier and an antiestrogen in accordance with the invention at a concentration sufficient to introduce from about 1 mg to about 1000 (preferably 5 to 50) mg of the antiestrogen per 50 kg of body weight per day. The volume flow will, of course, vary with the concentration at which the pharmaceutical composition is being administered.

During the early course of treatment, it is preferred to take occasional blood samples and to alter dosage as necessary to maintain serum concentration of the sum of the active compounds between about 0.2 µg/ml and 10 µg/ml.

In certain alternative embodiments, the pharmaceutical composition of the invention may be formulated for sustained release in accordance with known techniques. These sustained release formulations are preferably prepared in an appropriate manner for either oral, intramuscular, or subcutaneous administration.

Other alternative preferred embodiments include pharmaceutical compositions comprising therapeutically effective amounts of compounds of the formula:

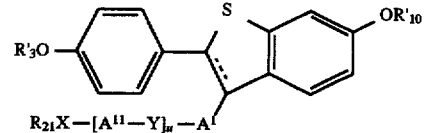

VII wherein the dotted line represents an optional pi bond, wherein $R'_3$, $R'_{10}$, $A^1$, Y, $A^{11}$, X, $R_{21}$ and u are defined as previously in formula VI especially $A^1-[Y-A^{11}]_u-XR_{21}$ is $-CO-p-C_6H_4-O-(CH_2)_nCONR_{21}R_{22}$;

wherein $R_{21}$ and $R_{22}$ are defined as previously for $R_6$ or $R_7$ in formula I and n is an integer from 1 to 15; or:

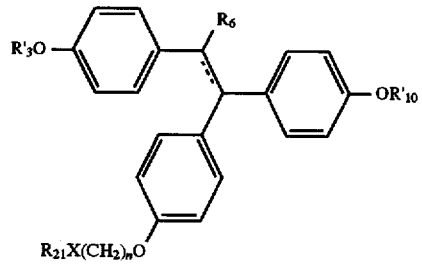

VIII wherein the dotted line represents optional double bond, especially in trans configuration, wherein $R'_3$, $R'_{10}$, $R_6$ are defined as previously; wherein $R_{21}$ is selected from the group consisting of hydrogen, straight- or branched-chain lower alkyl, lower alkenyl or lower alkynyl, $(C_3-C_7)$ cycloalkyl, halogeno(lower)alkyl, carboxy(lower)alkyl, (lower)alkoxycarbonyl(lower)alkyl, $(C_6-C_{10})$aryl, $(C_7-C_{11})$ arylalkyl, di(lower)alkylamino (lower)alkyl and fluoro-substituted analogs of the foregoing, wherein X is
—CONR$_{23}$—, —CSNR$_{23}$—, —NR$_{24}$CO—, —NR$_{24}$CS—,
—NR$_{24}$CONR$_{23}$—, —NR$_2$C(NR$_{25}$)NR$_{23}$—,
—SO$_2$NR$_{23}$—, —CO—, —CSS—, —SCS—, —O—,
—NR$_{23}$—, —(NO)R$_{23}$—, —(PO)R$_{23}$—, —NR$_{24}$COO—,
—NR$_{24}$SO$_2$—, —S—, —SO— or —SO$_2$—, wherein R$_{23}$ is
selected from the group consisting of hydrogen, lower alkyl
and a species which, together with R$_{21}$, forms a saturated or
unsaturated heterocyclic ring having at least one nitrogen
atom and fluoro-substituted analogs of the foregoing,
wherein R$_{24}$ is hydrogen or lower alkyl and wherein R$_{25}$ is
hydrogen, nitrile or nitro; or XR$_{21}$ forms a tetrazole ring; or

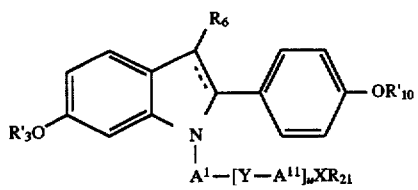

IX wherein the dotted line represents an optional pi bond,
wherein R'$_3$, R$_6$, R'$_{10}$, A$^1$, A$^{11}$, Y, X, R$_{21}$ and u are as defined
previously; or

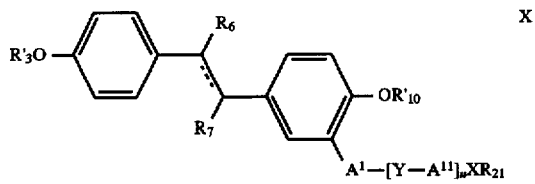

X wherein the dotted line represents an optional pi bond,
especially in trans configuration, wherein R'$_3$, R'$_{10}$, R$_6$, A$^1$,
A$^{11}$, Y, X, R$_{21}$ and u are defined as previously, wherein R$_7$
is preferably selected from the group consisting of
hydrogen, halogen, lower alkyl, amino, nitro, nitroso, nitrile,
lower alkylamino and dilower alkylamino; or

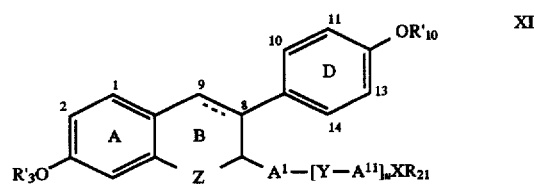

XI wherein the dotted line represents an optional double
bond, wherein R'$_3$, R'$_{10}$, A$^1$, A$^{11}$, Y, X, R$_{21}$ and u are defined
as previously for the formula I and VI, wherein A$^1$—[Y—
A$^{11}$]$_u$XR$_{21}$ is preferred in α configuration and wherein Z is
absent or selected from the group consisting of lower
alkylene, halogeno lower alkylene, —(CH$_2$)$_n$O—, —(CH$_2$)$_n$
S—, —(CH$_2$)$_n$Se—, —(CH$_2$)$_n$SO—, —(CH$_2$)$_n$SO$_2$—,
—(CH$_2$)$_n$CO—, —(CH$_2$)$_n$NR$_{22}$—, —(CH$_2$)$_n$SiR$_{22}$R$_{22}$— or
—(CH$_2$)$_n$CR$_{22}$OR$_{22}$—, (wherein R$_{22}$ is defined as previously and n is an integer from 0 to 3).

Preferred methods of treating of sex steroid-related
diseases, especially estrogen-related diseases, and preferred
methods of blocking estrogen receptors comprise administering to a patient in need of such treatment, a therapeutically effective amount (discussed supra) of a sex steroid-activity inhibitor as defined above.

Preferred estrogenic nuclei suitable for substitution with
the —R$^1$[—B—R$^2$]$_L$—G side chain in accordance with the
invention include but are not limited to compounds reported
in the literature as having estrogenic activity, natural estrogens such as estradiol, estrogenic derivatives thereof, and
other nuclei which provide the threshold increase in uterine
weight of ovariectomized rats set forth above as defining an
estrogenic nucleus (Simard et al., Mol. Endocrinol. 2:
775–784, 1988).

Some preferred estrogenic nuclei include but are not
limited to:

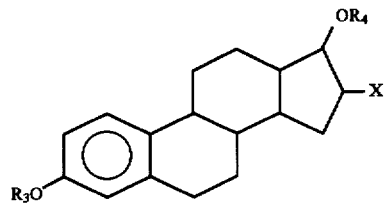

wherein x is a halogen, preferably chlorine or iodine;
wherein R$_3$ and R$_4$ are independently selected from the
group consisting of hydrogen, lower alkyl, lower alkoxy
carbonyl, (C$_1$–C$_{20}$), alkanoyl, (C$_3$–C$_{20}$)alkenoyl, (C$_3$–C$_{20}$)
alkynoyl and (C$_7$–C$_{11}$) aroyl, alkylsilyl, 1-alkyloxy-alkyl
and 1-alkyloxy cycloalkyl; - or -

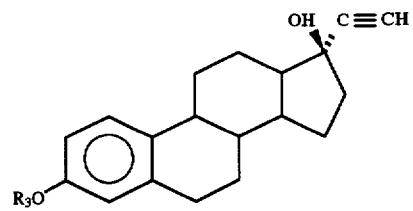

wherein R$_3$ is selected from the group consisting of
hydrogen, lower alkyl, lower alkoxy carbonyl, (C$_1$–C$_{20}$),
alkanoyl, (C$_3$–C$_{20}$) alkenoyl, (C$_3$–C$_{20}$) alkynoyl and
(C$_7$–C$_{11}$) aroyl, alkylsilyl, 1-alkyloxy-alkyl and 1-alkyloxy
cycloalkyl; - or -

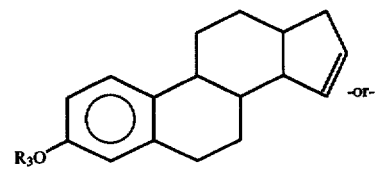

-or-

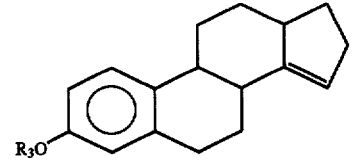

wherein R$_3$ is selected from the group consisting of
hydrogen, lower alkyl, lower alkoxy carbonyl, (C$_1$–C$_{20}$),
alkanoyl, (C$_3$–C$_{20}$) alkenoyl, (C$_3$–C$_{20}$) alkynoyl and
(C$_7$–C$_{11}$) aroyl, alkylsilyl, 1-alkyloxy-alkyl and 1-alkyloxy
cycloalkyl; - or -

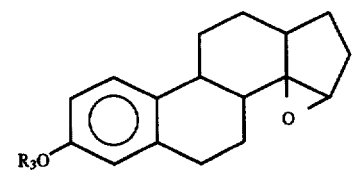

wherein R$_3$ is selected from the group consisting of
hydrogen, lower alkyl, lower alkoxy carbonyl, (C$_1$–C$_{20}$),
alkanoyl, (C$_3$–C$_{20}$) alkenoyl, (C$_3$–C$_{20}$) alkynoyl and ($C_7$–$C_{11}$) aroyl, alkylsilyl, 1-alkyloxy-alkyl and 1-alkyloxy cycloalkyl; - or -

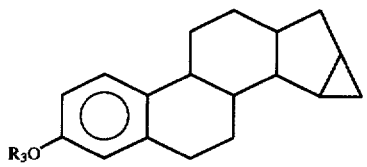

wherein $R_3$ is selected from the group consisting of hydrogen, lower alkyl, lower alkoxy carbonyl, ($C_1$–$C_{20}$), alkanoyl, ($C_3$–$C_{20}$) alkenoyl, ($C_3$–$C_{20}$), alkynoyl and ($C_7$–$C_{11}$) aroyl, alkylsilyl, 1-alkyloxy-alkyl and 1-alkyloxy cycloalkyl; - or -

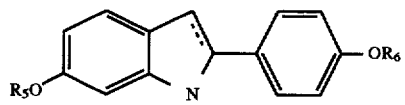

wherein the dotted line are an optional double bonds;
wherein $R_5$ and R6 are independently selected from the group consisting of hydrogen, lower alkyl, lower alkoxy carbonyl, ($C_1$–$C_{20}$), alkanoyl, ($C_3$–$C_{20}$) alkenoyl, ($C_3$–$C_{20}$) alkenoyl, ($C_3$–$C_{20}$) alkynoyl and ($C_7$–$C_{11}$) aroyl, alkylsilyl, 1-alkyloxy-alkyl and 1-alkyloxy cycloalkyl; - or-

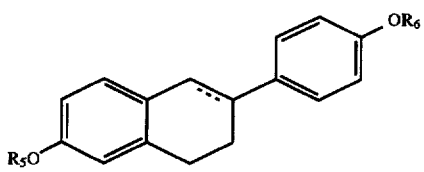

wherein the dotted line is an optional double bond;
wherein $R_5$ and $R_6$ are independently selected from the group consisting of hydrogen, lower alkyl, lower alkoxy carbonyl, ($C_1$–$C_{20}$), alkanoyl, ($C_3$–$C_{20}$) alkenoyl, ($C_3$–$C_{20}$) alkynoyl and ($C_7$–$C_{11}$) aroyl, alkylsilyl, 1-alkyloxy-alkyl and 1-alkyloxy cycloalkyl; - or -

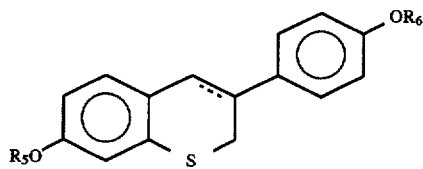

wherein the dotted lines are optional double bonds;
wherein $R_5$ and $R_6$ are independently selected from the group consisting of hydrogen, lower alkyl, lower alkoxy carbonyl, ($C_1$–$C_{20}$), alkanoyl, ($C_3$–$C_{20}$) alkenoyl, ($C_3$–$C_{20}$) alkynoyl and ($C_7$–$C_{11}$) aroyl, alkylsilyl, 1-alkyloxy-alkyl and 1-alkyloxy cycloalkyl; - or -

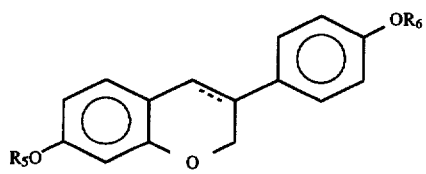

wherein the dotted line is an optional double bond
wherein $R_5$ and $R_6$ are independently selected from the group consisting of hydrogen, lower alkyl, lower alkoxy carbonyl, ($C_1$–$C_{20}$), alkanoyl, ($C_3$–$C_{20}$) alkenoyl, ($C_3$–$C_{20}$) alkynoyl and ($C_7$–$C_{11}$) aroyl, alkylsilyl, 1-alkyloxy-alkyl and 1-alkyloxy cycloalkyl; - or -

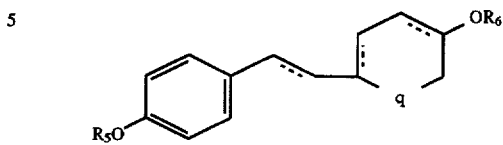

wherein q is absent, methylene or ethylene
wherein $R_5$ and $R_6$ are independently selected from the group consisting of hydrogen, lower alkyl, lower alkoxy carbonyl, ($C_7$–$C_{11}$) aroyl, alkylsilyl, 1-alkyloxy-alkyl and 1-alkyloxy cycloalkyl; - or -

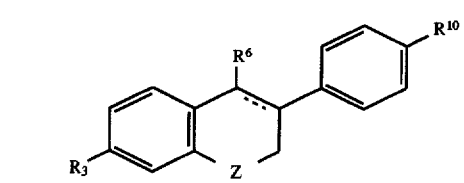

wherein Z is selected from the group consisting of lower alkylene, halogeno lower alkylene, —($CH_2$)$_n$O—, —($CH_2$)$_n$S—, —($CH_2$)$_n$Se—, —($CH_2$)$_n$SO—, —($CH_2$)$_n$SO$_2$—, —($CH_2$)$_n$CO—, —($CH_2$)$_n$NR$_{22}$—, —($CH_2$)$_n$SiR$_{22}$R$_{22}$— or —($CH_2$)$_n$CR$_{22}$OR$_{22}$ (wherein $R_{22}$ is defined as previously and n is an integer from 0 to 3);

wherein $R_3$ and $R_{10}$ are preferably independently selected from the group consisting of hydrogen, hydroxyl, OR$_3$', OR$_{10}$', halogen, lower alkyl, lower alkoxy, lower alkoxy carbonyloxy, carboxyl, ($C_1$–$C_{20}$) alkanoyloxy, ($C_3$–$C_{20}$) alkenoyloxy ($C_3$–$C_{20}$) alkynoyloxy, ($C_7$–$C_{11}$) aroyloxy and alkylsilyloxy;

wherein R'$_3$ and R'$_{10}$ are hydrogen, alkyl, ($C_1$–$C_{20}$) alkanoyl, ($C_3$–$C_{20}$) alkenoyl, ($C_3$–$C_{20}$) alkynoyl or ($C_7$–$C_{11}$) aroyl;

wherein $R_6$ is preferably selected from the group consisting of hydrogen, nitro, nitrile, halogen, lower alkyl, lower alkenyl, lower alkynyl, halogeno lower alkyl, halogeno lower alkenyl, halogeno lower alkynyl, alkyl sulfonyl, aryl sulfonyl, a substituted 5 to 7 member heterocyclic ring having at least one hetero atom (selected from oxygen, sulfur, silicon, selenium, nitrogen), —($CH_2$)$_s$W (wherein W is nitrile, hydroxyl, azido, nitroso, alkoxy, nitro, thionitrile, halogen, alkyl sulfonyl, aryl sulfonyl and s in an integer from 1 to 6), or has the formula:

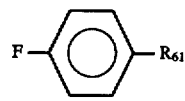

II wherein:
F is absent or selected from the group consisting of alkyl, carbonyl or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_6$($CH_2$)$_n$$Y_6$, wherein $X_6$ is selected from the group consisting —O—, —S—, —Se—, —SO—, —SO$_2$— and —CO—, and $Y_6$ is selected from the group consisting hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n is an integer from 1 to 6 preferably 3.

Preferred sex steroid activity inhibitors result from substituting estrogenic nuclei such as those set forth in the foregoing examples with the preferred substituents set forth herein, including the side chains defined above (e.g. —R¹—[—B—R²—]$_x$L—G). Preferred sex steroid activity inhibitors in accordance with the invention include are not limited to:

N-n-butyl-N-methyl-11-(16'α-bromo-3',17'β-dihydroxy-estra-1',3',5'(10')-trien-7'α-yl) undecanamide ("EM 105"):

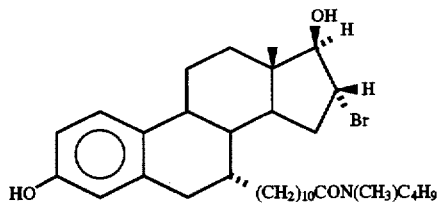

N-n-butyl-N-methyl-11-(16'α-bromo-3',17'α-dihydroxy-estra-1',3',5'(10')-trien-7'α-yl) undecanamide ("EM 171"):

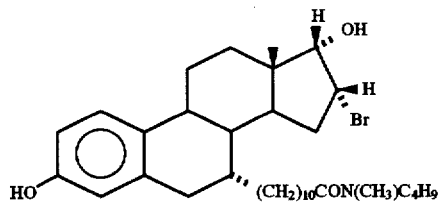

N-n-butyl-N-methyl-11-(16'α-chloro-3',17'β-dihydroxy-estra-1',3',5'(10')-trien-7'α-yl) undecanamide ("EM 139"):

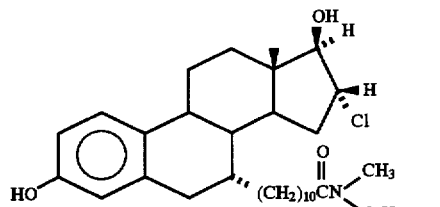

N-n-butyl-N-methyl-11-(16'α-chloro-3',17'α-dihydroxy-estra-1',3',5'(10')-trien-7'α-yl) undecanamide ("EM 170"):

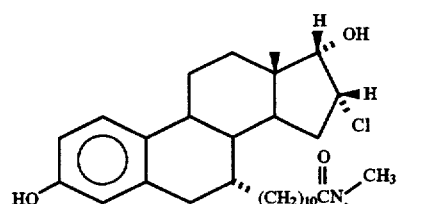

N-n-butyl-N-methyl-11-(16'α-iodo-3',17'β-dihydroxy-estra-1',3',5'(10')-trien-7'α-yl) undecanamide ("EM 156"):

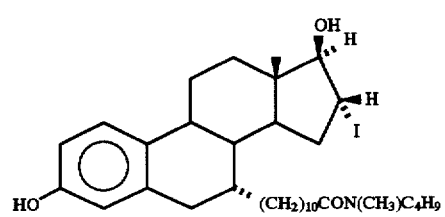

-continued

N-n-butyl-N-methyl-11-(3'-hydroxy-17'-oxo-estra-1',3',5'(10'),15'-tetraen-7'α-yl) undecanamide ("EM 112"):

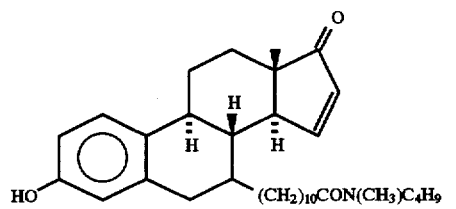

N-n-butyl-N-methyl-11-(3',17'β-dihydroxy-17'α-ethynyl-estra-1',3',5'(10'),15'-tetraen-7'α-yl)undecanamide ("EM 123"):

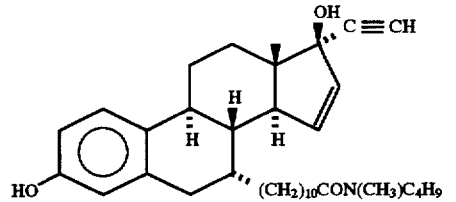

N-n-butyl-N-methyl-11-(3',17'β-dihydroxy-17'α-ethynyl-estra-1',3',5'(10'),14'-tetraen-7'α-yl)undecanamide ("EM 140"):

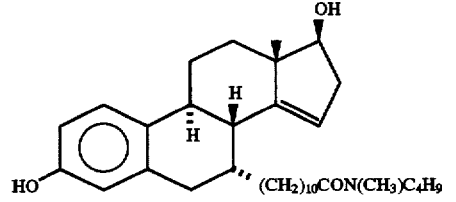

N-n-butyl-N-methyl-11-(3',17'β-dihydroxy-15'β,16'β-methylene-estra-1',3',5'(10'),15'-trien-7'α-yl)undecanamide ("EM 136"):

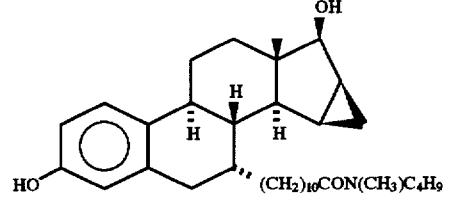

N-n-butyl-N-methyl-11-(3',17'β-dihydroxy-17'α-ethynyl-estra-15'β,16'β-methylene-estra-1',3',5+(10')-trien-7'α-yl)undecanamide ("EM 138"):

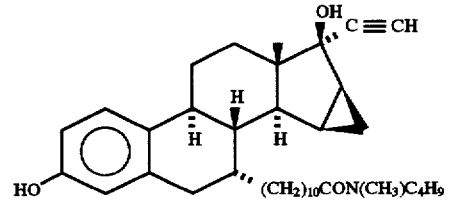

N-n-butyl-N-methyl-11-(3'-hydroxy-15'β,16'β-methylene-17'-oxo-estra-1',3',5'(10')-trien-7'α-yl)undecanamide ("EM 137"):

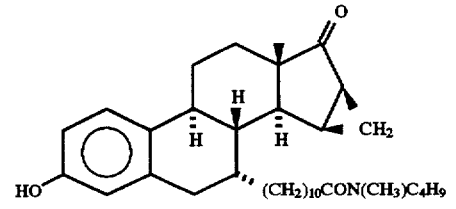

-continued

N-n-butyl-N-methyl-11-(3'-hydroxy-16'-methylene-17'-oxo-estra-1',3',5'(10')-trien-7'α-yl) undecanamide ("EM 175"):

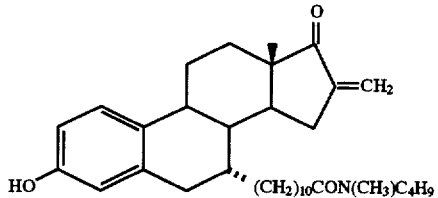

N-n-buty-N-methyl-11-(3',17'β-dibenzoyl-14'β,15'β-epoxy-estra-1',3',5'(10')-trien-7'α-yl)undecanamide ("EM 180"):

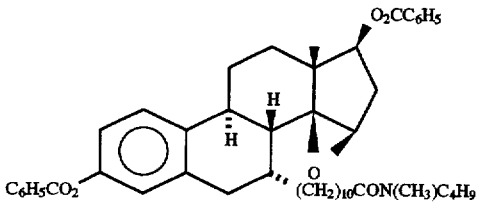

N-n-butyl-N-methyl-11-(3',17'β-dibenzoyl-14'α,15'α-epoxy-estra-1',3',5'(10')-trien-7'α-yl)undecanamide ("EM 181"):

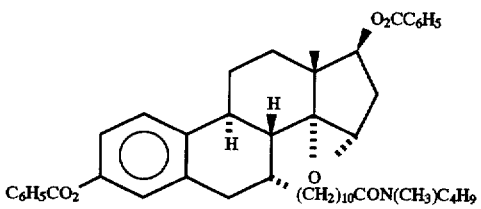

N-n-butyl-N-methyl-11-(3',17'β-dihydroxy-estra-1',3',5'(10')-trien-7'α-yl)undecanamide ("EM 108"):

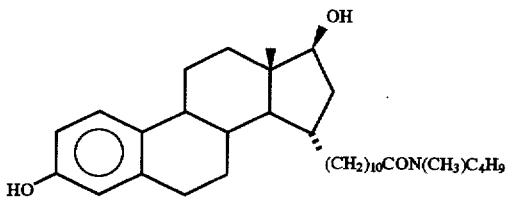

N-n-butyl-N-methyl-13-(3',17'β-dihydroxy-estra-1',3',5'(10')-trien-7'α-yl)12-tridecynamide ("EM 163"):

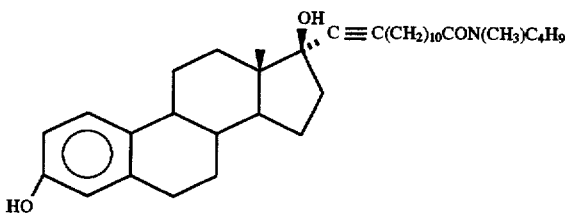

N-n-butyl-N-methyl-14-(3',17'β-dihydroxy-estra-1',3',5'(10')-trien-7'α-yl)13-tetradecynamide ("EM 195"):

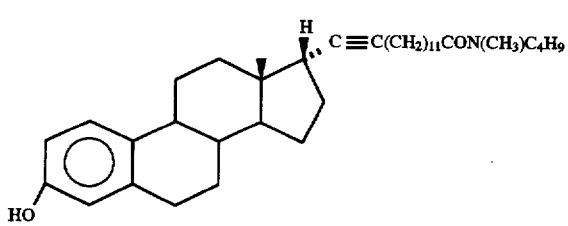

-continued

N-n-butyl-N-methyl-8-(3',17'⊖-dihydroxy-estra-1',3',5'(10')-trien-7'α-yl)7'octynamide ("EM 157"):

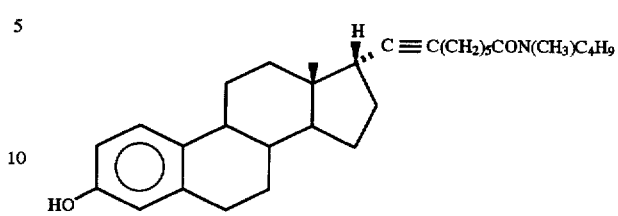

N-n-butyl-N-methyl-11-(6'-hydroxy-2'-(4"-hydroxyphenyl)-3'ethyl-indol-N'-yl) undecanamide (EM 215):

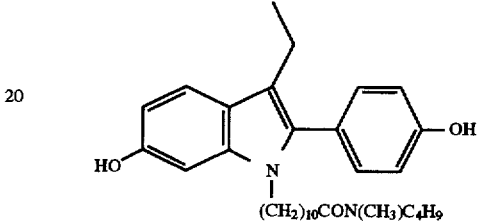

N-n-butyl-N-methyl-11-(6'-hydroxy-2'-(4"-hydroxyphenyl)3',4'-dihydronaphtalene-3'-yl) undecanamide:

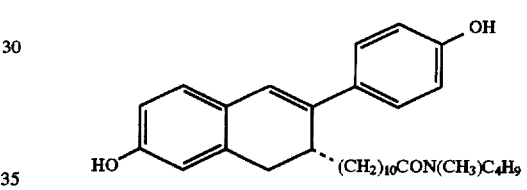

N-n-butyl-N-methyl-11-[4,4'-(1,2-diethyl-1,2-ethanydyl) bis-phenol-3-yl)] undecanamide (EM 406):

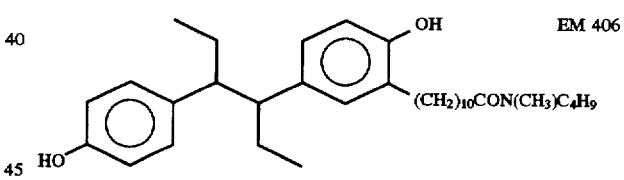

6-hydroxy-2-(4'-hydroxyphenyl)-1-methyl-3-(6"-piperidino)hexyl-3,4-dihydronaphatalene (EM 473)

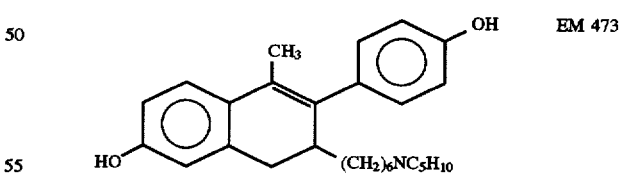

N-n-butyl-N-methyl-11-(6'-hydroxy-2'-(4"-hydroxyphenyl)-1'-menthyl-3',4'-dihydronaphatalene-3'-yl) undecanamide (EM 690)

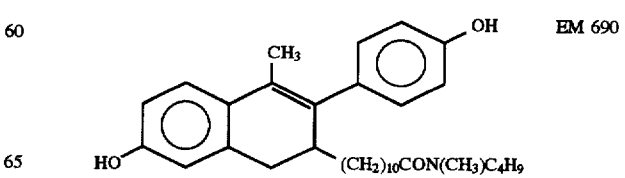

-continued 6-hydroxy-2-(4'-hydroxyphenyl)-1-methyl-3-
pentafluoropentylsulphinylnonyl-3,4-dihydronaphatalene (EM 732)

2-(4'-hydroxyphenyl)-1-methyl-3-[4"-(2"'-piperidinoethoxy)
penhyl]-3,4-dihydronaphatalene (EM 765)

2-(4'-hydroxyphenyl)-1-methyl-3-[4"-(2"-piperidinoethoxy)
benzyl]-3,4-dihydronaphatalene (EM 431)

N-pyrrolidinyl-11-(7'-hydroxy-3'-(4"-hydroxyphenyl)-4'-methyl
-2H-benzothiopyran-2'-yl) undecanamide (EM 941)

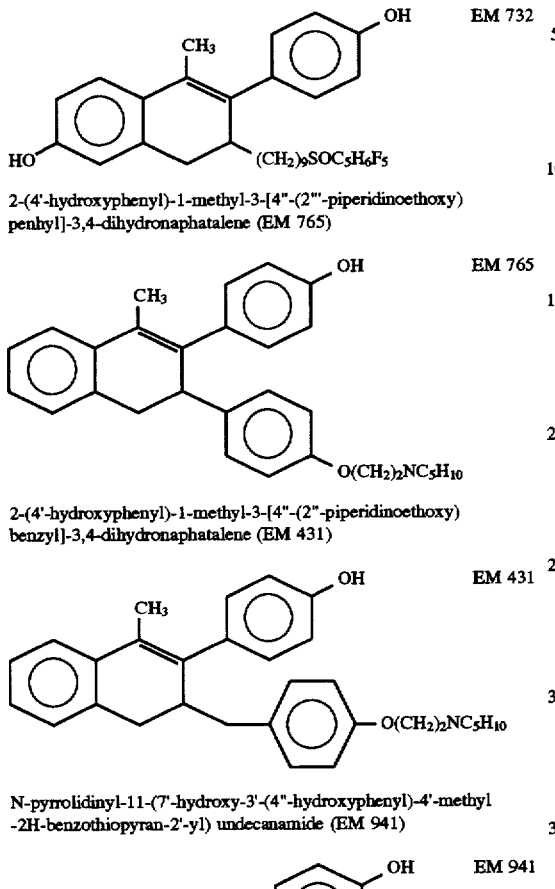

-continued 7-hydroxy-3-(4'-hydroxyphenyl)-4-methyl-2-[3'-(2"-piperidino)
ethoxy]propynyl-2H-benzopyran (EM 555)

N-n-butyl-N-methyl-11-(7'-hydroxy-3'(4"-hydroxyphenyl)-4'-
methyl-2H-benzopyran-2-yl) undecanamide (EM 467)

7-hydroxy-3-(4'-hydroxyphenyl)-4-methyl-2-(6"-piperidino)hexyl-
2H-benzopyran (EM 721)

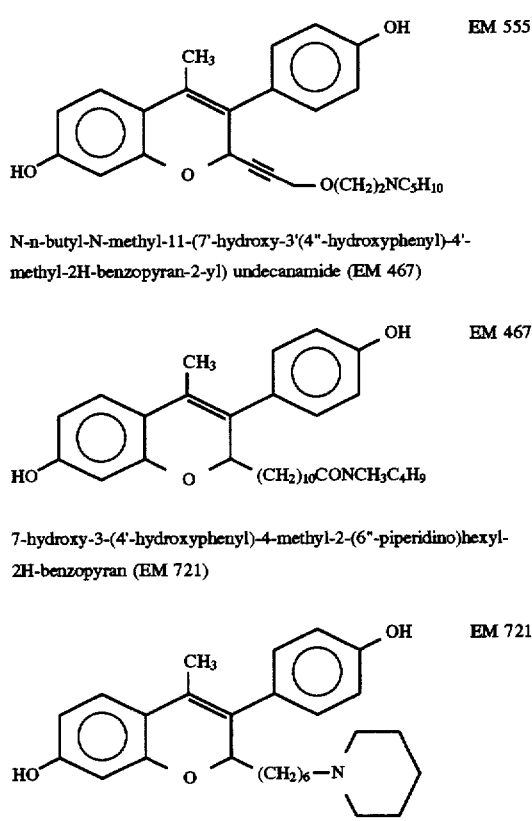

When a sex steroid nucleus is substituted with the side chain $R^1$—B—$R^2$—$]_x$ L—G, it is preferred that the side chain have between about 7 and 30 carbon atoms and that L be separated from the nucleus by at least 3 intervening and preferably 6 atoms. In some embodiments, a polar moiety (G, L or both) is preferably separated from the nucleus by at least 8 intervening atoms.

Additional inhibitors of the formula:

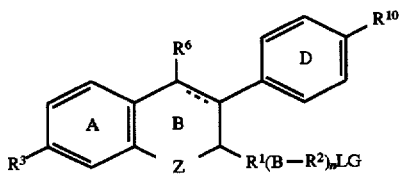

Include but are not limited to those set forth below:

| Inhibitor | $R^1$ | B | $R^2$ | x | L | G | Double bond | Z | $R^6$ | $R^3$ | $R^{10}$ |
|---|---|---|---|---|---|---|---|---|---|---|---|
| EM-732 | —$CH_2$— | Absent | $(CH_2)_4$ | 2 | SO | $C_5H_6F_5$ | Yes | —($CH_2$)— | —$CH_3$ | —OH | —OH |
| EM-473 | Absent | Absent | $(CH_2)_3$ | 2 | | —N⟨piperidine⟩ | Yes | —($CH_2$)— | —$CH_3$ | —OH | —OH |
| EM-734 | -Ø- | O | $(CH_2)_2$ | 1 | $NCH_3$ | $CH_3$ | Yes | —($CH_2$)— | $CH_3$ | H | OH |

Additional inhibitors of the formula:

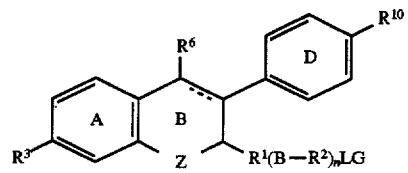

Include but are not limited to those set forth below:

| Inhibitor | $R^1$ | B | $R^2$ | x | L | G | Double bond | Z | $R^6$ | $R^3$ | $R^{10}$ |
|---|---|---|---|---|---|---|---|---|---|---|---|
| EM-349 | -Ø- | O | $-(CH_2)-$ | 1 | $-N\smile O$ (morpholine) | | Yes | O | H | $-OH$ | $-OH$ |
| EM-428 | -Ø- | O | $-(CH_2)_2-$ | 1 | $-N\smile$ (pyrrolidine) | | Yes | O | $-CH_3$ | H | OH |
| EM-384 | -Ø- | O | $-(CH_2)_3-$ | 1 | $-N\smile$ (piperidine) | | Yes | O | $-CH_3$ | H | H |
| EM-350 | -Ø- | O | $CH_2$ | 1 | $-C(=O)-N\smile$ | | Yes | O | H | $-OH$ | $-OH$ |
| EM-357 | -Ø- | O | $CH_2$ | 1 | $-C(=O)-NCH_3$ | $C_4H_9$ | Yes | O | H | $-OH$ | $-OH$ |
| EM-345 | $-CH_2-$ | Absent | $(CH_2)_2$ | 3 | $CONCH_3$ | $C_4H_9$ | Yes | O | H | $-OH$ | $-OH$ |
| EM-371 | $-CH_2-$ | Absent | $(CH_2)_5$ | 2 | $NCH_3$ | $C_4H_9$ | Yes | O | H | $-OH$ | $-OH$ |
| EM-511 | $-CH_2-$ | Absent | $(CH_2)_4$ | 2 | SO | $C_5H_6F_5$ | Yes | O | H | $-OH$ | $-OH$ |
| EM-555 | $-C\equiv C-CH_2-$ | O | $-(CH_2)_2$ | 1 | $-N\smile$ (piperidine) | | Yes | O | $CH_3$ | $-OH$ | $-OH$ |
| EM-547 | -Ø- | O | $-(CH_2)_2$ | 1 | $-NC_2H_5-$ | $C_2H_5$ | Yes | S | H | H | OH |
| EM-762 | $-CH_2-$ | O | $-(CH_2)_2$ | 2 | $CONCH_3-$ | $C_4H_9$ | Yes | S | H | OH | OH |
| EM-821 | -Ø- | O | $-(CH_2)_2$ | 1 | $-N\smile$ (piperidine) | | Yes | $NCH_3$ | H | OH | OH |
| EM-736 | $-CH_2$ | Absent | $-(CH_2)_3-$ | 2 | $-CONCH_3$ | $C_4H_9$ | Yes | $-CH_2)-$ | $-(CH_3$ | $-OH$ | $-OH$ |
| EM-698 | Absent | Absent | $-(CH_2)_4-$ | 2 | $-CONCH_3$ | $C_4H_9$ | Yes | $-(CH_2)-$ | $-CH_3$ | $-OH$ | $-OH$ |
| EM-721 | $-(CH_2)_6$ | Absent | Absent | 0 | $-N\smile$ (piperidine) | | Yes | $-O-$ | $-CH_3$ | $-OH$ | $-OH$ |
| EM-343 | -Ø- | $-O-$ | $-(CH_2)_2-$ | 1 | $-N\smile$ (piperidine) | | Yes | $-O-$ | $-CH_3$ | $-OH$ | $-OH$ |

The following compound of the invention:

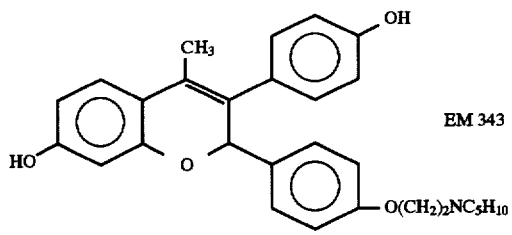

EM 343 was synthesized and tested for its ability to inhibit the growth of ZR-75-1 human breast cancer cell line. The results are reported in FIG. 5 as further discussed below.

The synthesis is described in Scheme A and Scheme 33. The synthesis of the compound 23 is described in Scheme A, and the starting materials and reagents were purchased from Aldrich Chemical Company Inc. (Milwaukee, Wis.). Thus, the acid chloride 1 (20.0 g; 0.1 mol) was added dropwise to methanol (60 ml) at room temperature and with stirring. The solution was refluxed for 1 h. The solvent was removed under reduced pressure and the resulting oil was dissolved in ethyl acetate. The organic solution was washed with saturated sodium bicarbonate aqueous solution. The organic solution was dried ($MgSO_4$) and the solvent was removed under reduced pressure. The residue was purified by chromatography on silica gel (ethyl acetate: hexanes; 1:9) to yield the compound 2 (Scheme A) (18.0 g; 92%).

The above ester 2 (21.2 g; 0.108 mol) and the nitrile 3 (available from Aldrich Chemical Company Inc., Milwaukee, Wis.) (17.5 ml; 0.129 mol) were dissolved in benzene (750 ml). The solution was refluxed and some benzene (100 ml) was removed by means of a Dean Stark apparatus. The solution was left to cool down; then sodium ethoxide (9.2 g; 0.135 mol) was added. The resulting mixture was refluxed for 18 h; it was washed with 1N hydrochloric acid aqueous solution. The organic solution was dried ($MgSO_4$) and the solvent was removed under reduced pressure. The residue was purified by chromatography on silica gel (ethyl acetate: hexanes; 1:4) to yield compound 4 (23 g; 69%). (δ NMR; 300 MHz; solvent: $CDCl_3$; standard: TMS) 3.78 (3H; s; OMe) 3.84 (3H; s; OMe) 3.95 (3H; s; OMe) 5.84 (1H; s; O=C—CH—CN) 6.43 (1H; d; J 2.5 Hz; CH phenyl) 6.54 (1H; dd; J 2.5 Hz and 8.5 Hz; CH phenyl) 6.89 and 7.35 (2H; AB system; J 8.5 Hz; CH phenyl) 7.79 (1H; d; J 8.5 Hz; CH phenyl).

A solution of the ketone 4 (37.8 g; 0.12 mol) in acetic acid (400 ml) and concentrated hydrochloric acid aqueous solution (200 ml) was kept at 90° C. for 3 h. The reaction mixture was neutralized with concentrated sodium hydroxide aqueous solution and it was extracted with ethyl acetate. The organic extract was dried ($MgSO_4$) and the solvent was removed under reduced pressure. The residue was purified by chromatography on silica gel (ethyl acetate: hexanes; 1:9) to yield compounds 5 (17.0 g; 49%) and 6 (6.6 g; 20%).

Triphenol 23

To a mixture of the ketones 5 (17.0 g; 59.4 mmol) and 6 (6.6 g; 24.3 mmol) was added pyridine hydrochloride (90 g). The mixture was heated at 220° C. for 20 min. 1N hydrochloric acid aqueous solution (250 ml) was added and the resulting mixture was extracted several times with ethyl acetate. The organic extract was dried ($MgSO_4$) and the solvent was removed under reduced pressure. The residue was purified by chromatography on silica gel (ethyl acetate: hexanes; 3:7) to yield compound 23 (14.1 g; 69%).

The continuation of the synthesis of EM 343 is described below with reference to Scheme 33 (page 183).

Diether 24

To a mixture of the triphenol 23 (14.1 g; 57.8 mmol) in 3,4-dihydro-2H-pyran (200 ml) at 0° C. and with vigourous stirring was carefully added p-toluenesulfonic acid monohydrate (2.0 g). The reaction mixture was stirred at 0° C. for a further 1 h. Ether (300 ml) was added and the solution was washed with 1N sodium hydroxide aqueous solution. The organic extract was dried ($MgSO_4$) and the solvent was removed under reduced pressure. The residue was purified by chromatography on silica gel (ethyl acetate: hexanes; 1:9) to yield compound 24 (23.4 g; 98%). (δ NMR; 300 MHz; solvent: $CDCl_3$; standard: TMS) 1.5–2.1 (12H; m; O—CH—$CH_2$—$CH_2$—$CH_2$—$CH_2$—O THP) 3.55–3.65 (2H; m; O—CH—$CH_2$—$CH_2$—$CH_2$—$CH_2$—O THP) 3.75–3.95 (2H; m; O—CH—$CH_2$—$CH_2$—$CH_2$—$CH_2$—O THP) 4.16 (2H; s; Ph—$CH_2$—C=O) 5.40 (1H; t; J 3Hz; O—CH—$CH_2$—$CH_2$—$CH_2$—$CH_2$—O THP) 5.49 (1H; t; J 3 Hz; O—CH—$CH_2$—$CH_2$—$CH_2$—$CH_2$—O THP) 6.55 (1H; dd; J 2.5 Hz and 8.5 Hz; CH phenyl) 6.61 (1H; d; J 2.5 Hz; CH phenyl) 7.03 and 7.17 (2H; AB system; J 8.5 Hz; CH phenyl) 7.77 (1H; d; J 8.5 Hz; CH phenyl) 12.60 (1H; s; Ph—OH).

Chroman-4-one 25 (R=H) and Chalcone 26 (R=H)

To a mixture of the diether 24 (24.4 g; 59.2 mmol) and the aldehyde ($OHCC_6H_4OH$) (7.6 g; 62.18 mmol in dry benzene (750 ml) was added piperidine (500 μl). The solution was refluxed for 48 h and water was continuously removed by means of a Dean Stark apparatus. The solvent was removed under reduced pressure and the residue was purified by chromatography on silica gel (ethyl acetate: hexanes; 1:9) to yield compounds 25 (R=H) (14.3 g; 47%) and 26 (R=H) (8.4 g; 27%). This last compound can be converted to compound 25 (R=H) by heating with sodium acetate in methanol.

Chroman-4-one 25 (R=H)

(δ NMR; 300 MHz; solvent: $CDCl_3$; standard: TMS)

1.5–2.1 (12H; m; O—CH—$CH_2$—$CH_2$—$CH_2$—$CH_2$—O THP) 3.45–3.65 (2H; m; O—CH—$CH_2$—$CH_2$—$CH_2$—$CH_2$—O THP) 3.8–3.95 (2H; m; O—CH—$CH_2$—$CH_2$—$CH_2$—$CH_2O$ THP) 4.05–4.1 (1H; m O—CH—CH—C=O) 5.25–5.35 (1H; m O—CH—CH—C=O) 5.35–5.55 (2H; m; O—CH—$CH_2$—$CH_2$—$CH_2$—$CH_2$—O THP) 6.6–7.1 (10H; m; CH phenyl) 7.85–7.95 (1H; m; CH phenyl).

SCHEME A

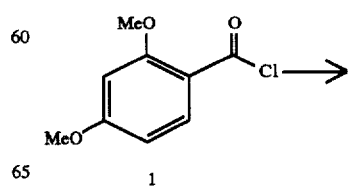

1

-continued
SCHEME A

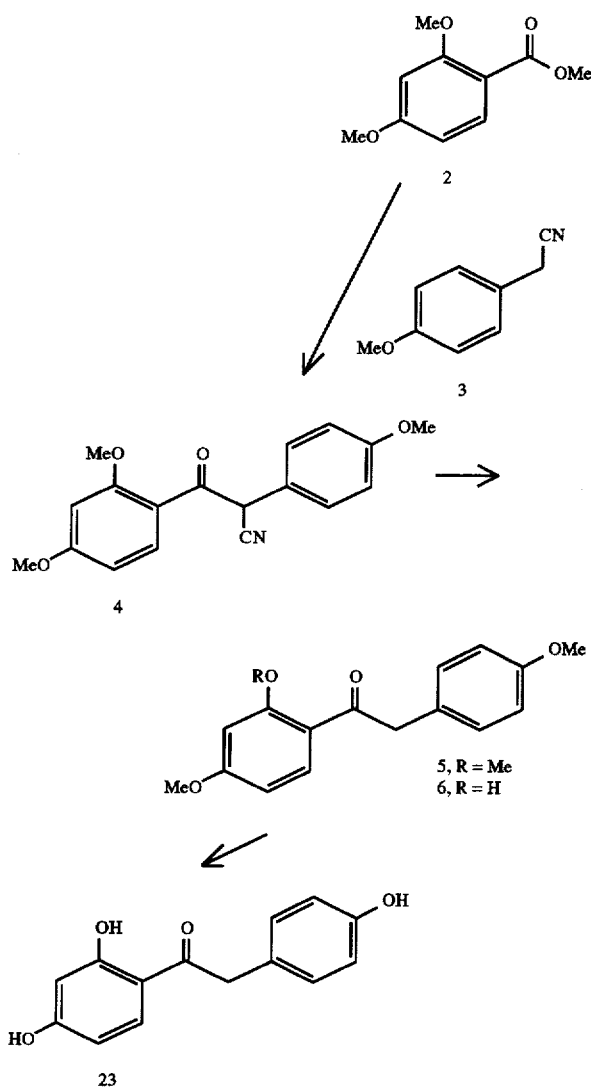

EM 343

A mixture of compound 25 (R=H) (1.90 g; 3.8 mmol), 1-(2-chloroethyl)piperidine hydrochloride Cl(CH$_2$)$_2$NC$_5$H$_{10}$·HCl (1.18 g; 6.5 mmol) and sodium carbonate (0.97 g; 9.1 mmol) in acetone (100 ml) was kept under reflux and with stirring for 48 h. The precipitate was filtered off and washed thoroughly with acetone. The solvent was removed under reduced pressure and the residue was purified by chromatography on silica gel (hexanes:acetone; 7:3+a few drops of triethylamine) to yield compound 25 (R=(CH$_2$)$_2$NC$_5$H$_{10}$) (1.57 g; 66%). To a solution of compound 25 (R=(CH$_2$)$_2$NC$_5$H$_{10}$) (90 mg; 143 μmol) in ether (30 ml) was added methylmagnesium iodide (3.0M solution in ether; 1.2 ml; 3.6 mmol) at 0° C. and with stirring. The mixture was stirred for a further 3 h. at room temperature, then washed with saturated ammonium chloride solution. The organic solution was dried (MgSO$_4$) and the solvent was removed under reduced pressure. The residue was quickly filtered through silica gel (ethyl acetate: acetone; 1:1) to afford compound 27 (R=(CH$_2$)$_2$NC$_5$H$_{10}$, Rc=CH$_3$)(90 mg; 97%) which was used directly in the next reaction.

A solution of compound 27 (R=CH$_2$)$_2$NC$_5$H$_{10}$, Rc=CH$_3$) (90 mg; 139 μmol) in a mixture of acetic acid (60 ml) and water (6 ml) was kept at 100° C. for 10 min. The solvent was removed under reduced pressure and the residue was purified by chromatography on silica gel (ethyl acetate: acetone; 3:2) to yield compound 28 (EM 343, R=(CH$_2$)$_2$NC$_5$H$_{10}$, Rc=CH$_3$)(40 mg; 62%). (δ NMR; 300 MHz; solvent: CD$_3$OD; standard: TMS), 1.46 (2H; m; cyclo—N—CH$_2$—CH$_2$—CH$_2$—CH$_2$—CH$_2$) 1.60 (4H; m; cyclo—N—CH$_2$—CH$_2$—CH$_2$—CH$_2$—CH$_2$—) 2.02 (3H; s; CH$_3$—C=C) 2.56 (4H; m; cyclo—N—CH$_2$—CH$_2$—CH$_2$—CH$_2$—CH$_2$—) 2.76 (2H; t; J 5 Hz, O—CH$_2$—CH$_2$—N) 4.06 (2H; t; J 5 Hz; O—CH$_2$—CH$_2$—N) 5.77 (1H; s; O—CH—Ph) 6.12 (1H; d; J 2.5 Hz; CH Phenyl) 6.35 (1H; dd; J 2.5 Hz, 8 Hz; CH Phenyl) 6.70 (2H; d; J 8.5 Hz; CH Phenyl) 6.77 (2H; d; J 8.5 Hz; CH Phenyl) 6.98 (2H; d; J 8.5 Hz; CH Phenyl) 7.12 (1H; d; J 8 Hz; CH Phenyl) 7.19 (2H; d; J 8.5 Hz; CH Phenyl). Mass Spectroscopy: M+459.

The product, EM 343, was then prepared for efficacy testing using the ZR-75-1 human breast cancer cell line.

Maintenance of Stock Cell Cultures

ZR-75-1 cells (83rd passage) were obtained from the American Type Culture Collection (Rockville, Md.) and routinely cultured in phenol-red free RPMI 1640 supplemented with 1 nM E$_2$, 2 mM L-glutamine, 1 mM sodium pyruvate, 15 mM N-2-hydroxyethyl-piperazine-N'-2-ethanesulfonic acid, 100 IU penicillin/ml, 100 μg streptomycin/ml, and 10% (v/v) fetal bovine serum (Hyclone, Logan, Utah) under a humidified atmosphere of 95% air, 5% CO$_2$, at 37° C. All media and medium supplements were purchased from Sigma. Cells were subcultured weekly by treatment with a pancreatic solution containing 0.02% EDTA (w/v). The cell cultures used for the experiments herein described were between passages 89 and 94.

Measurements of Cell Proliferation

Cells in their logarithmic growth phase were harvested, briefly centrifuged, and resuspended in RPMI 1640. Cells were then plated in triplicate in LIMBRO 24-well plastic culture plates (2 cm$^2$/well). Since plating density influences the effect of hormones on ZR-75-1 cell growth, cells were plated at a density of 1×10$^4$ cells/well. After 72 h, medium was replaced with fresh medium of identical composition containing, in addition, the concentrations of steroids and/or inhibitors (e.g. EM 312 or EM 343) indicated along the X-axis of FIG. 5. Control cultures received the ethanol vehicle only. Cells were then allowed to grow at 37° C. for 10 days with medium changes (of identical composition) every 2 days. In absence of inhibitors, in 0.1 nM estradiol (E$_2$)-containing medium, ZR-75-1 cells have doubling time of about 48 h.

After E$_2$ and/or antiestrogen treatment, cells were harvested by addition of 0.5 ml of a pancreatin solution (Sigma) for 5–10 min at 37° C. before addition of 0.5 ml of RPMI 1640 containing 5% dextran-coated charcoal-fetal bovine serum in order to block enzymatic action. Cell number (0.10-ml aliquot was determined by measurement of DNA content as previously described (Simard et al., Endocrinology 126: 3223–3231, 1990).

Figure 5:
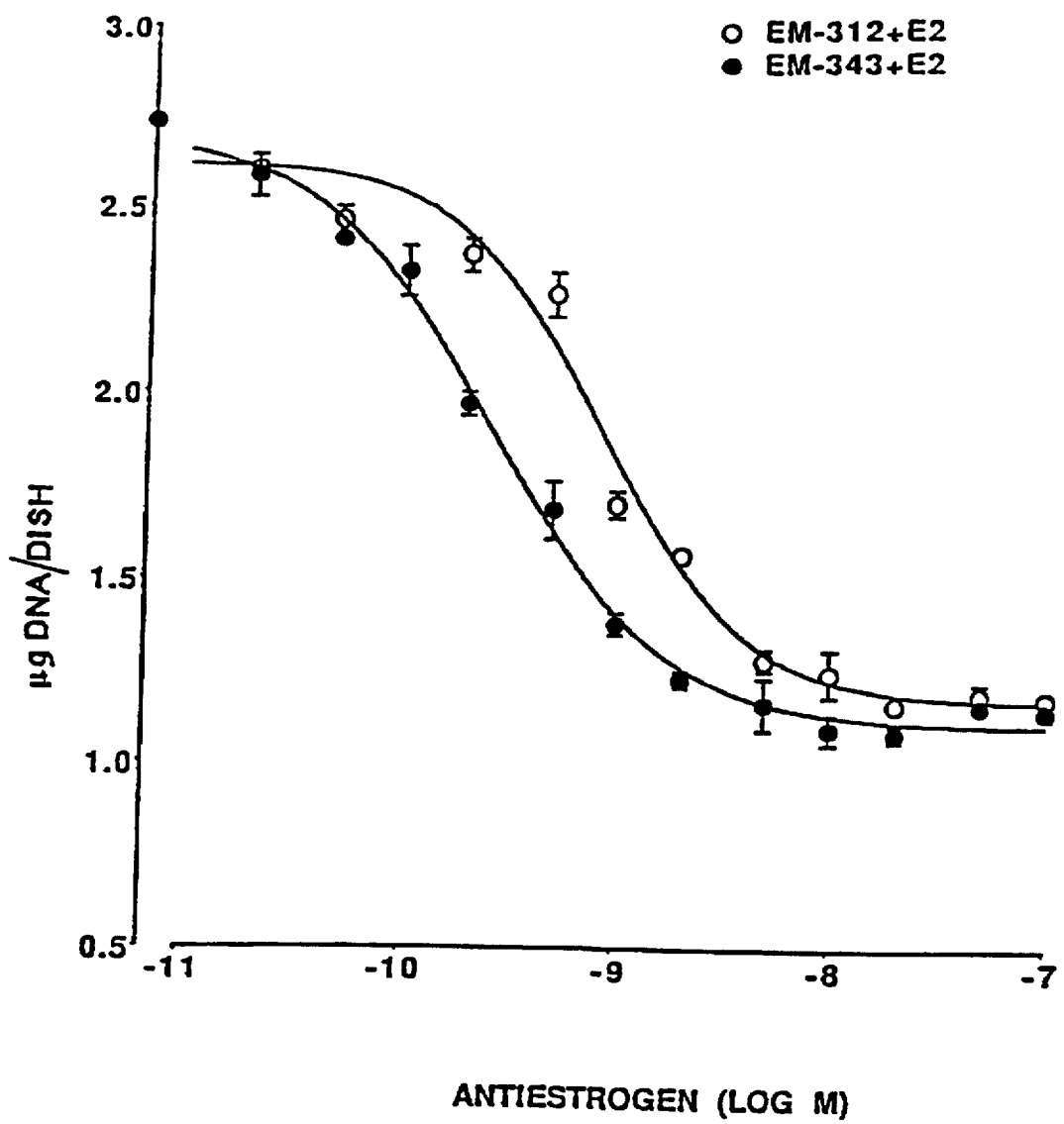
FIG. 5 is a graph illustrating the antiestrogen activity of EM 343 and EM 312.

As may be seen from FIG. 5, EM 343 provided extensive cell growth inhibition at low concentration. Half-maximal effectiveness occurred at a concentration of 2.55×10$^{-10}$M. Without intending to be bound by theory, it is believed that the B-ring alkyl substitution utilized in certain preferred embodiments of the invention (e.g. the methyl substitution of EM 343) enhances effectiveness relative to compounds lacking such a substitution. For example, another species of the invention:

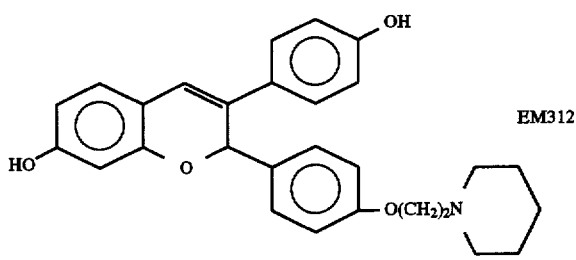

EM312 reported by Saeed et al (J. Med. Chem. 33: 3210–3216, 1990) and Sharma et al (J. Med. Chem. 33: 3216–3222 and 3222–3229, 1990) to have antiestrogenic activity underperformed EM 343 in comparative testing in our laboratory on the growth of human ZR-75-1 breast cancer cells, the IC$_{50}$ value of EM-312 being 3-fold higher at $8.43 \times 10^{-10}$M (FIG. 5).

Set forth below are some flow charts description and illustration of a number of preferred synthesis schemes for certain preferred antiestrogens in accordance with the invention. The steps set forth below are set forth merely by way of example. Those of skill in the art will readily recognize alternative synthetic pathways and variations capable of producing a variety of antiestrogens and other sex steroid activity inhibitors in accordance with the invention.

EXAMPLES OF SYNTHESIS OF PREFERRED INHIBITORS OF SEX STEROID ACTIVITY

Instrumentation

The IR spectra were taken on a Perkin-Elmer 1310 spectrophotometer. Proton NMR spectra were recorded on a Varian EM-160A (60 MHz, when specified) or a Varian XL-200 (MHz) instrument. The following abbreviations have been used: s, singlet; d, doublet; dd, doublet of doublet; t, triplet; q, quadruplet; and m, multiplet. Chemical shifts are reported in δ values in ppm relative to tetramethysilane (TMS) as internal standard. Mass spectra (MS) were obtained on a V. G. Micromass 16F machine. Thin-layer chromatography (TLC) was performed on 0.25 mm Kieselgel 60F254 plates (E. Merck, Darmstadt, FRG). For flash chromatography, Merck-Kieselgel 60 (230–400 mesh A.S.T.M.) was used. All solvents used in chromatography have been distilled. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Anhydrous solvents were prepared in the following way.

| SOLVENT | DISTILLED OVER |
|---|---|
| AMINE, DIMETHYFORMAMIDE | CaH$_2$ |
| HEXANE, DICHLOROMETHANE | P$_2$O$_3$ |
| ACETONE | K$_2$CO$_3$ |
| BENZENE | LiAlH$_4$ |
| TOLUENE | Na |
| ETHER, TETRAHYDROFURAN | LiAlH$_4$, Na benzophenone |

LIST OF ABBREVIATIONS

Bz Benzyl
DMF Dimethylformamide
EDTA Ethylenediaminetretraacetic acid
HMPA Hexamethylphosphoramide
HPLC High pressure liquid chromatography
LDA Lithium diisopropylamine
mCPBA meta-chloroperbenzoic acid
MOM Methyloxymethyl
NAD Nicotinamide Adenine Dinucleotide
NADH Nicotinamide Adenine Dinucleotide reduced form
PTSA Para-toluene sulfonic acid
PTSCl Para-toluene sulfonyl chloride
TBDMS t-butyldimethylsilyl
THF Tetrahydrofuran
THP Tetrahydropyrannyl
TMS Tetramethylsilyl

EXAMPLE I

Instrumentation

IR spectra were obtained in a Perkin-Elmer spectrometer 1310. UV spectra were recorded in methanol on a Beckman DU-6 spectrometer. H-NMR spectra were obtained at 200 MHz on a Varian XL-200 spectrometer. Chemical shifts are reported in ppm units with tetramethylsilane as internal standard. Mass spectra were obtained on Micromass 16F spectrometer.

N-butyl, N-methyl-12,13-Bis (4-hydroxyphenyl)-12-pentadecenoic amide (EM-142, compound 5 with x=10)

The synthesis of this compound is described in the scheme I (infra) where x=10.

12,13-Bis (4-methoxyphenyl)-11-pentadecenol (3)

4'-methoxy-2-ethyl,2-(4-methoxyphenyl) acetophenone (2) (710 mg, 2.5 mmol, prepared from desoxyanisoin, ethyl bromide and LDA by a known method) in THF (10 ml) were added, under argon, to Grignard reagent prepared from 11-bromo-tetrahydropyranyl undecanol (6.6 g, 19.7 mmoles) and magnesium (0.6 g, 24.7 mmoles) and THF (10 ml). The mixture was stirred for 18 hours, then acidified with 1N HCl and extracted three times with ether. The organic phase was washed with water (X3), dried over anhydrous magnesium sulfate, and evaporated under reduced pressure. The residue was chromatographed on Silica-gel (Kieselgel, 60F254, Merck, 0.063–0.200 mm, 100 g). Elution with a mixture of hexane-ethyl acetate (9:1 v/v) gave 12,13-Bis-(4-methoxyphenyl)-tetrahydropyranyl pentadecan-1,12-diol (991 mg, 76%) as a mixture of diastereoisomers; colorless oil, IRv$_{max}$ (neat) 3480, 1600 cm$^{-1}$; $^1$H-NMR (δ CDCl$_3$); 0.62 (3H, t, J=7.3 Hz, CH$_2$CH$_3$), 2.73 (1H, 2d, J=9.7 Hz, —CHCH$_2$CH$_3$), 3.25–4.00 (4H, m, —CH$_2$OCHOCH$_2$—), 3.76 and 3.79 (6H, 2s, —OCH$_3$), 4.57 (1H, t, J=1.1 Hz, —O$_2$—CH—CH$_2$) and 6.71–7.30 (8H, m, H-Ar)ppm. MS m/e=523 (M$^+$—H$_2$O).

The above diastereoisomers (920 mg, 1.8 mmol dissolved in methanol (30 ml) and 5N HCl (5 ml was refluxed for 1 hour, then collected, and extracted three times with ether. The organic layer was washed with water, dried over anhydrous magnesium sulfate, evaporated under reduced pressure to dryness and finally chromatographed on silica gel (Kieselgel, 60F254, 0.063–0.200 mm, Merck, 100 g). Elution was a mixture of hexane-ethyl acetate (7:3 v/v) gave 12,13-Bis(4-methoxyphenyl)-11-pentadecenol (3) (710 mg, 65% from compound 2), colorless oil, IR, v$_{max}$ (neat), 3340, 1600, 1030 cm$^{-1}$; UV γ$_{max}$ (log ε)=231 (4.27) nm; $^1$H—NMR (δ, CDCl$_3$), 0.88 (3H, t, J=7.3 Hz, —CH$_2$CH$_3$), 3.30 (1H, t, J=9.7 Hz, —CH—CH$_2$.CH$_3$), 3.63 (2H, t, J=6.6 Hz, —CH$_2$OH), 3.76 and 3.78 (6H, 2s, —OCH$_3$), 5.51 (1H, t, J=8.8 Hz, 1 —C=CH) and 6.63–7.10 8H, m, H—Ar) ppm; MS m/e=438 (M$^+$).

N-butyl, N-methyl,12,13-Bis (4-methoxyphenyl)-11-pentadecenoic amide (4)

To a cooled solution of alcohol 3 (710 mg, 1.56 mmol) in acetone (17 ml) was added Jones' reagent (8N-chromic acid solution, 0.77 ml). After 30 minutes, isopropanol (5 ml) was added and the mixture was poured in water and extracted three times with ethyl acetate. The organic layer was washed twice with brine, dried over magnesium sulfate and evaporated to dryness. The crude 12,13-Bis (4-methoxyphenyl-11-pantadecenoic acid was used in the next step without purification. To its solution in anhydrous methylene chloride (4 ml) at −10° C. was added, under stirring, triisobutylamine (470 μl, 1.96 mmol) and isobutylchloroformate (280 μl, 2.1 mmol). After 40 minutes, N-methylbutylamine (1.5 ml) was added and the mixture was stirred at room temperature during 1 hour. Methylene chloride (50 ml) was added. The organic solution was washed with 1N HCl, saturated sodium bicarbonate solution and water (3X), dried on magnesium sulfate and evaporated to dryness. The residue was purified by "Flash chromatography" on silica gel (Kieselgel 60, Merck, under 0.063 mm, 50 g). Elution with a mixture of hexane-ethyl acetate (4:1 v/v) gave N-butyl, N-methyl-12,13-Bis( 4-methoxyphenyl)-11-pentadecenoic amide (4), (549 mg, 68%) colorless oil; IR $v_{max}$ (neat), 1640, 1600 cm$^{-1}$; UV $\gamma_{max}$ (log ε)=230, (4.39) nm; $^1$H-NMR (δ, CDCl$_3$), 0.85–0.98 (6H, m, 2—CH$_2$CH$_3$), 2.27 (2H, t, J=7.1 Hz, C H$_2$CON), 2.91 and 2.96 (3H, 2s, —NCH$_3$), 3.25–3.36 (3H, m, —NCH$_2$ and CH$_3$CH$_2$CH—), 3.77 and 3.78 (6H, 2s, OC H$_3$), 5.50 (1H, J=7.1 Hz, —C=CH—) and 6.69–7.01 (8H, m, H—Ar) ppm; MS m/e=521 (M$^+$).

N-butyl, N-methyl-12,13-Bis (4-hydroxyphenyl)-12-pentadecenoic amide (EM-142, compound 5 with x=10).

To the above dimethoxy amide 4, (117 mg, 0.22 mmol) in CH$_2$Cl$_2$ (1 ml) at 0° C. was added, under argon, 1.0M borane tribromide (675 μl). The solution was stirred for 1 hour, then poured into water and extracted with ether (3x). The organic solution was washed with water, dried on magnesium sulfate, and evaporated to dryness. The residue was purified by "Flash chromatography" on silica gel (Kieselgel 60, Merck, under 0.063 mm, 30 g). Elution with mixture of hexane-ethyl acetate (4:1 v/v) gave N-butyl, N-methyl-12, 13-Bis (4-hydroxyphenyl)-12-pentadecenoic amide (EM-142, compound 5 with x=10) (34 mg, 31%), colorless oil, IR $v_{max}$ (neat) 3300, 1600 cm$^{-1}$; UV $_{\gamma max}$ (log ε)=235 (4.25) nm; $^1$H-NMR (δ, CDCl$_3$), 0.76 (3H, t, J=7.3 Hz, —CH$_2$C H$_3$), 0.96 (3H, t, J=7.3 Hz, N (CH$_2$)$_3$CH$_3$), 2.05–2.20 (4H, m, CH$_2$—C=C—CH$_2$—), 2.35 (2H, t, J=7.0 Hz, —CH$_2$CON—), 2.97 and 3.00 (3H, s, —NCH$_3$), 3.29 and 3.41 (2H, 2t, J=7.3 Hz, —N—CH$_2$—), and 6.59–7.09 (8H, m, H—Ar) ppm; MS m/e=493 (M$^+$).

Scheme 1

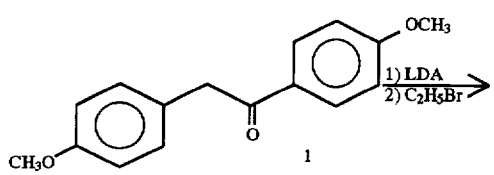

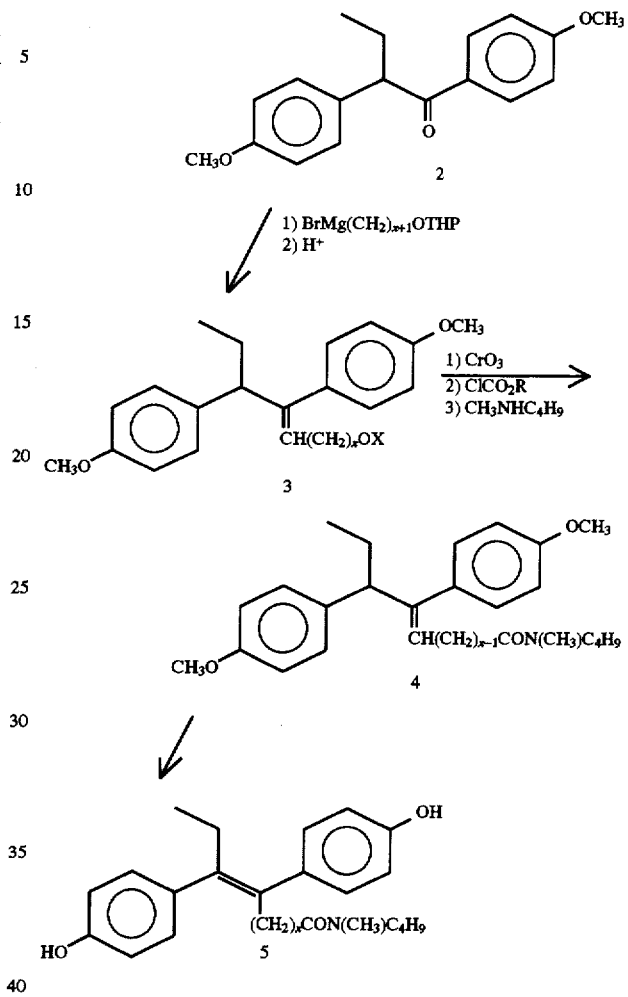

EXAMPLE 2

EFFECTIVENESS OF ANTIESTROGEN SYNTHESIZED IN EXAMPLE 1

EM-142 from example 1 was tested by competition binding on the rat uterine cytosol estrogen receptor with [$^3$H] estradiol according to Asselin et al. (1976) prodecure. FIG. 1 shows the binding affinity of EM-142 compared with estradiol, diethylstilbestrol and ICI 164384 (Wakeling and Bowler, 1987). (incubation was performed at 25° C. for 3 hours). It can be seen that EM-142 is only 3 times less potent than 17β-estradiol itself while being more potent than the antiestrogen ICI 164384.

The antiestrogenic activity of EM-142 was measured in vivo by inhibition of the estradiol-induced stimulation of uterine weight in adult female ovariectomized Balb/c mice (body weight=19–20 g) sacrificed five days after ovariectomy. EM-142, and/or estradiol contained in ethanol were injected subcutaneously in the appropriate groups in a solution of 0.9% (w/v) sodium chloride and 1% (w/v) gelatin at different concentrations in 0.2 ml for EM-142, twice daily, starting on the day of ovariectomy for a total of 9 injections. Estradiol was injected at the dose of 0.01 μg in 0.2 ml, twice daily, starting on the morning after ovariectomy for a total of 8 injections.

Figure 2:
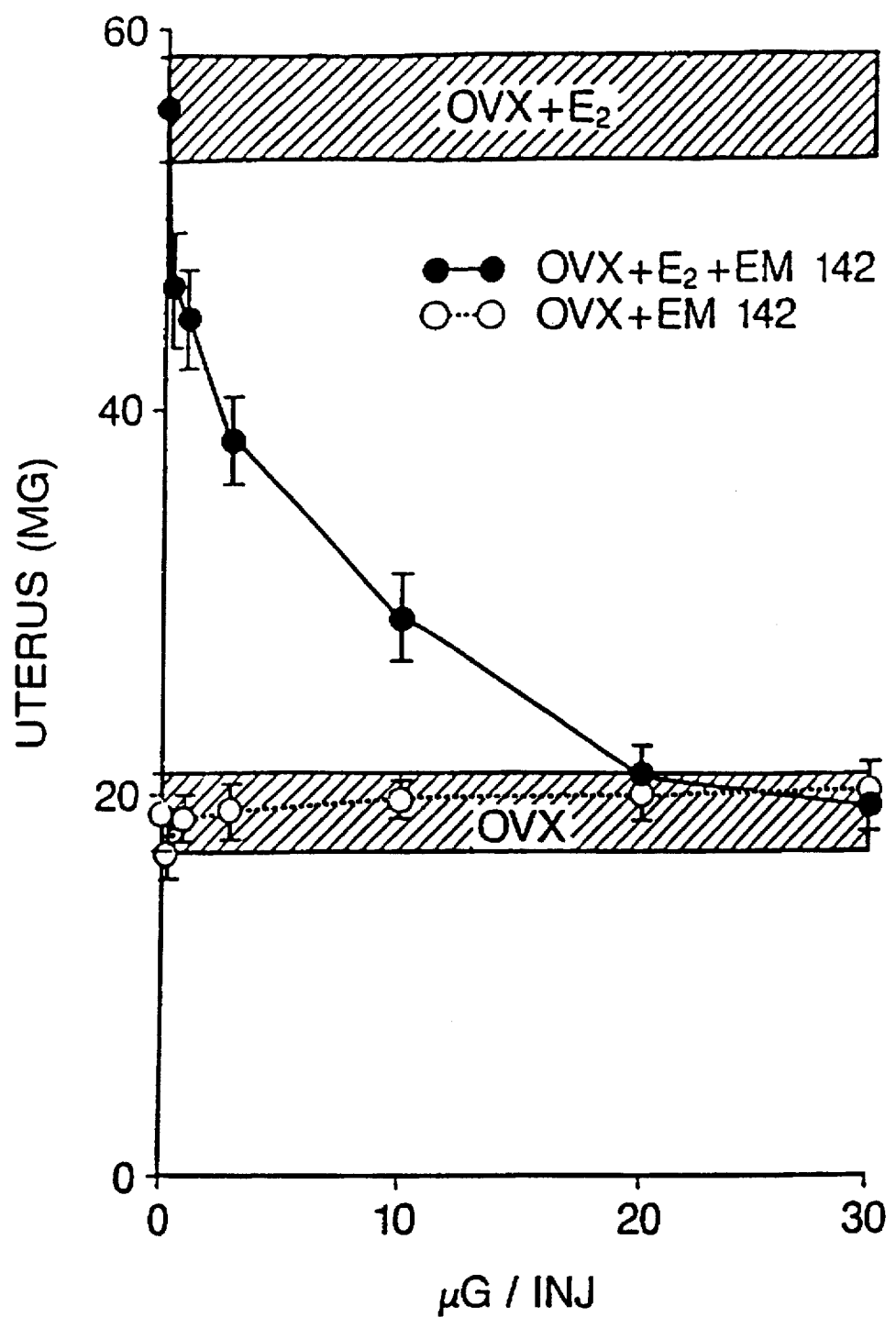
FIG. 2 illustrates the effect of the indicated doses of EM-142 injected twice daily (b.i.d.) on uterine weight (mg) in adult female ovariectomized Balb/C mice treated for 4.5 days in the presence (OVX+E$_2$+EM 142) or absence (OVX+ EM 142) of simultaneous treatment with 17β-estradiol (0.01 ug, b.i.d.).

After sacrifice, the uteri were rapidly removed, freed from fat and connective tissue and weighted. Results shown in FIG. 2 are the means ±SEM of groups of 9–10 mice. It can be seen that the very low dose of 0.3 μg already has a significant inhibitory effect of an E₂-induced uterine growth and that a complete reversal of E₂ effect is obtained at higher doses. A half-maximal inhibitory effect is in fact observed at approximately 3 μg while, at the doses used, 20 μg causes a complete reversal of estrogenic action. Note that EM-142 has no estrogenic effect on uterine weight, thus demonstrating its potent antiestrogenic activity.

EXAMPLE 3

Scheme 2

N-butyl, N-methyl-12,13-Bis-(4-hydroxyphenyl) pentadecanoic amide (6)

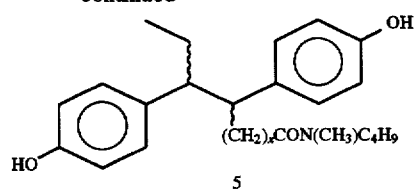

EXAMPLE 4

Scheme 3

N-butyl, N-methyl-5-[4-[(2-[4-hydroxyphenyl] benzothiophen-3-yl) formyl] phenoxy] hexanoic amide (12)

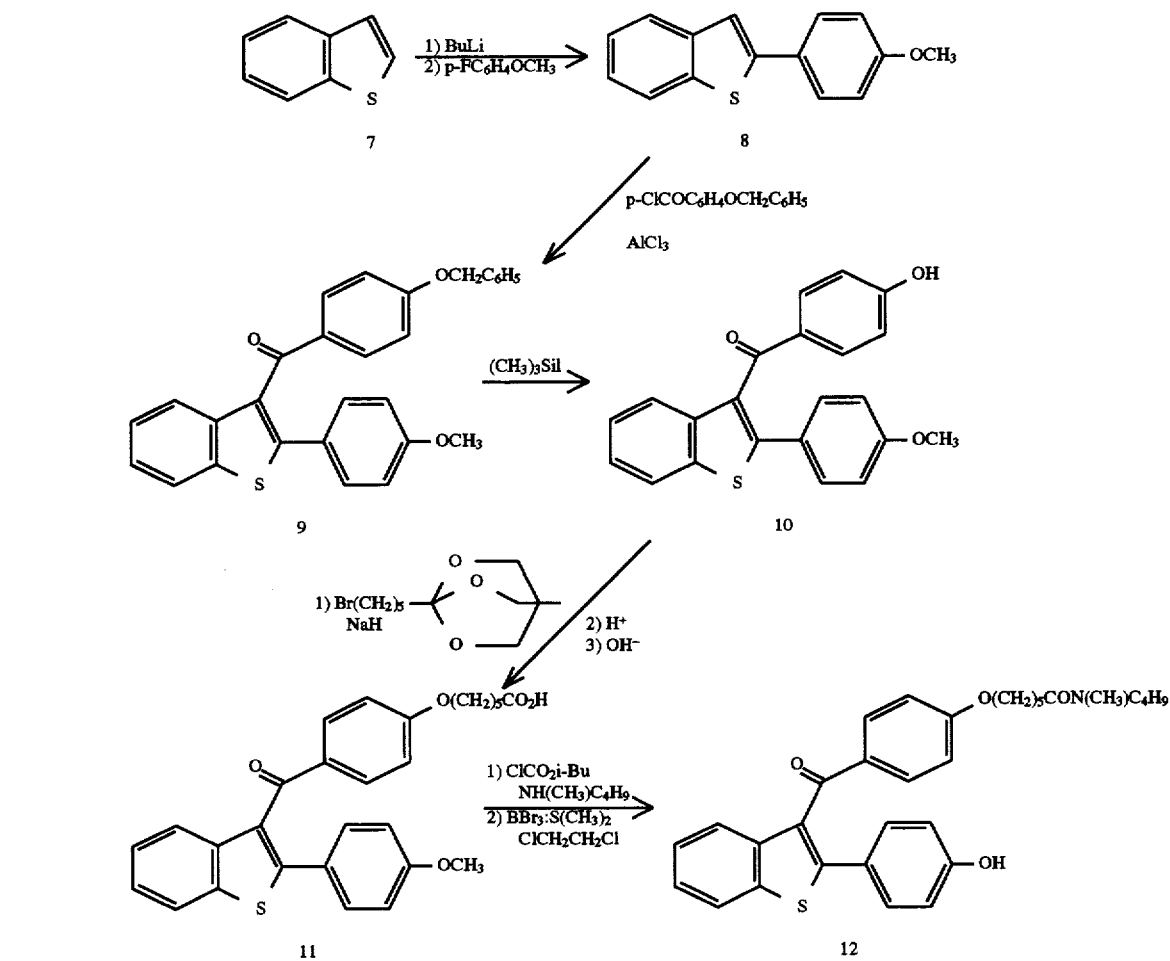

EXAMPLE 5 (Scheme 4)
N-butyl, N-methyl-6-[p-(trans-1',2'-bis (4"-hydroxyphenyl)-1'-butenyl) phenoxyl] heptanoic amide (18)
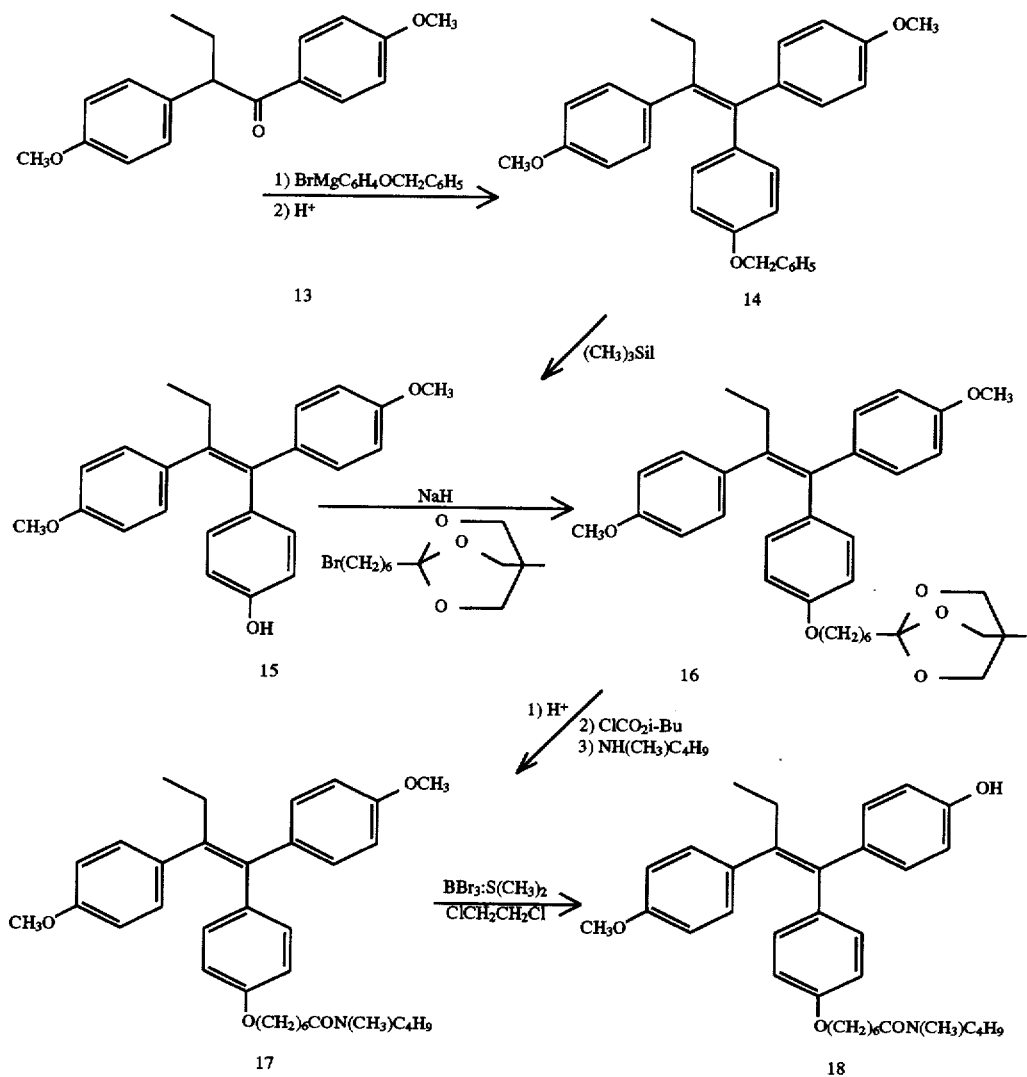
EXAMPLE 6
Scheme 5
N-butyl, N-methyl-(6'-hydroxy, 2'-(4"-hydroxyphenyl)-3'-methyl-indol-N'-yl) undecanoic amide (22)

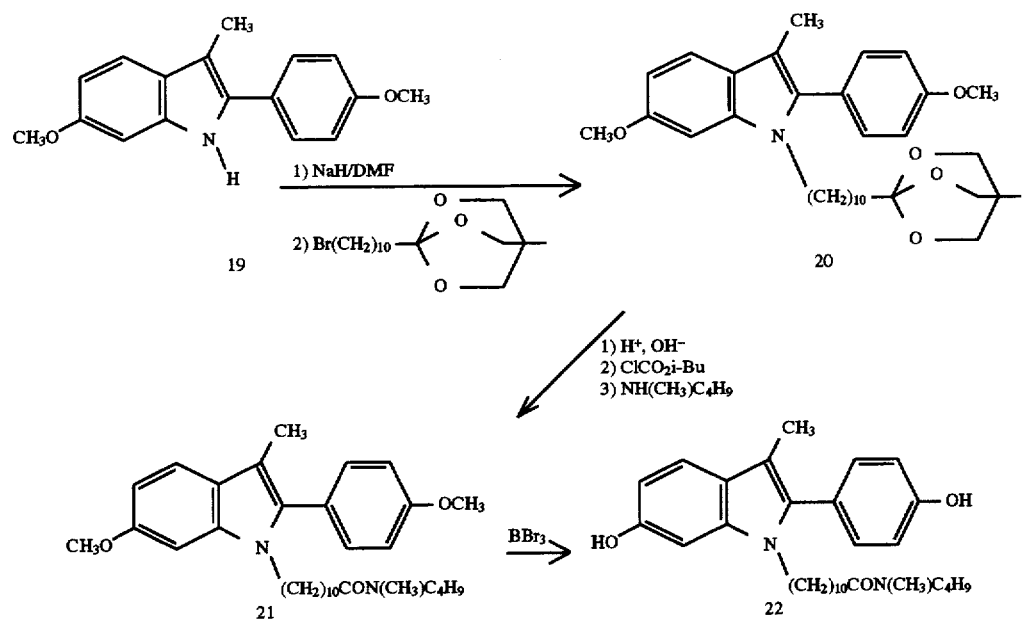
EXAMPLE 7
Scheme 6
N-butyl, N-Methyl-11-[4,4'-(1,2-diethyl-1,2-ethanydiyl) bis-phenol-3-yl] undecanoic amide (28)
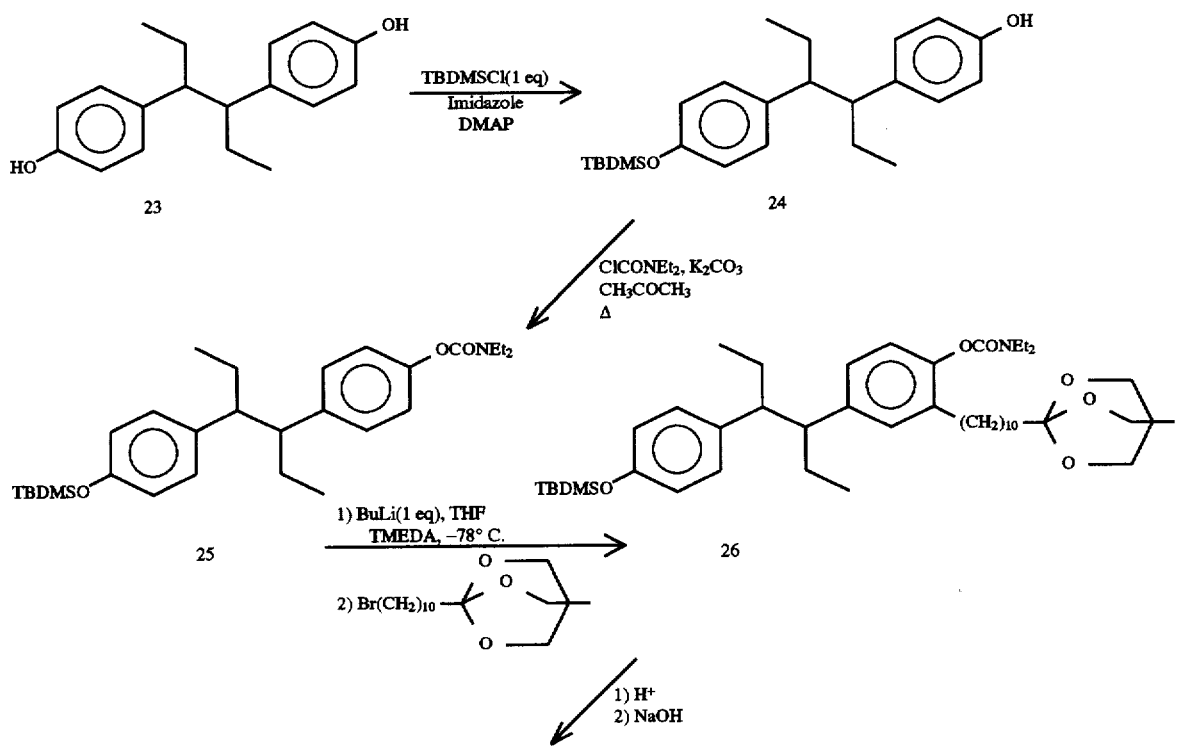

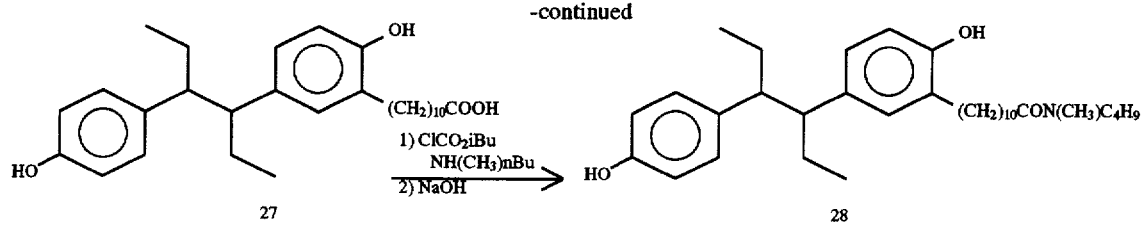
EXAMPLE 8 (Scheme 7)
N-butyl, N-methyl-[6'-hydroxy-2'-(4-hydroxyphenyl)-(1', 2'-dihydronaphta-len-3'-yl) undecanoic amide (34)
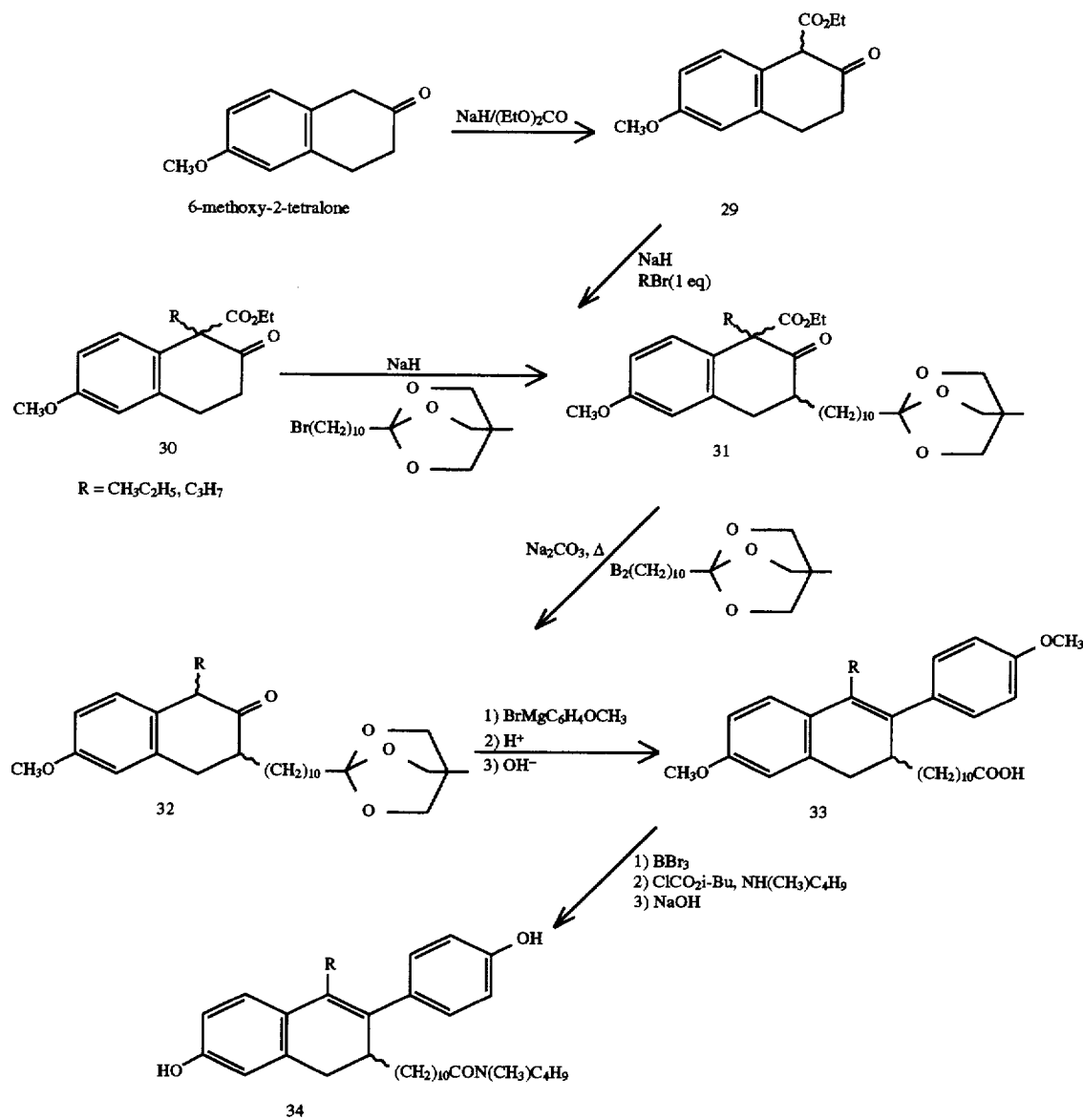

EXAMPLE 9

SYNTHESIS OF A STARTING COMPOUND, N-N-BUTYL, N-METHYL-11-(3'-BENZOYLOXY-17'-OXO-ESTRA-1'3',5'(10')-TRIEN-7'α-YL) UNDECANAMIDE (9) (SCHEME 8, INFRA))

19-nor-testosterone-acetate 3-enolacetate (2)

In an apparatus supplied with a drierite drying tube, a solution of 19-nor-testosterone (10) (100 g; 0.365 mole) in acetic anhydride (200 ml), pyridine (32 ml) and acetylchloride (320 ml) was heated at reflux under magnetic stirring, for 3 h and then concentrated to dryness under vacuum. The dry residue was triturated in absolute ethanol, filtered and washed with little portions of absolute ethanol. After drying, 19-nor-testosterone acetate 3-enolacetate was obtained as a white powder (121.4 g, yield 93%) mp. 176°–177° C. The structure was confirmed by spectroscopic means.

17β-acetoxy-estra-4,6-dien-3-one (3)

To a cooled suspension of enolacetate (121 g; 0.337 mole) in a mixture of DMF (330 ml and water (7.2 ml) at 0° C. was added, under nitrogen, over a period of 1 h, N-bromosuccinimide (63 g). The resulting solution was stirred for an additional 0.5 h at 0° C. Then lithium carbonate (60.8 g) and lithium bromide (30.4 g) were added. The mixture was Mated at 95° C. for 3 h and then poured into 1.7 l of ice-cold water containing 165 ml of glacial acetic acid. After stirring during 15 hours, the crude 17β-acetoxy-estra-4,6-dien-3-one (3) was filtered, washed with water, dried in a desiccating apparatus and recrystallized twice from isopropyl ether (72 g, yield 68%, mp 110° C.). The structure was confirmed by spectroscopic means.

7α-(11'-acetoxy-undecyl) 17β-acetoxy estra-4-en-3-one (4)

A. Preparation of reagents and solvents 11-bromo undecanol tetrahydro pyranyl ether 11-bromo-undecanol (100 g, 398 mmol) was dissolved in dry ether (768 ml) and the solution was cooled to 0° C. using an ice/$H_2O$ bath. To this solution was added HCl gas (2.13 g, 58.4 mmol, 26 ml of HCl/ether).

To this mixture, a solution of 3,4-dihydro-2H-pyran (39.9 g, 43.3 ml) freshly distilled in dry ether (218 ml) was added over a period of 90 min. The solution was then stirred over a period of 16 hours at room temperature. Afterwards, sodium bicarbonate was added to the mixture. The residue was filtered and the solvent was evaporated under vacuum.

The product was then filtered through basic alumina (250 g, Woelm, grade II) using petroleum ether (30–60) as solvent (112 g, 81%).

B. Grignard reagent

In a dry three-neck flask (1000 ml) under dry argon, magnesium (12.0 g, 494 mmol) was placed and activated with iodine. Magnesium was heated with the flame to remove iodine and to dry the apparatus. The system was then cooled to –20° C., and a solution of 11-bromo-undecanol tetrahydropyranyl ether (73.8 g, 211 mmol) in dry THF (420 ml) was added dropwise. The mixture was stirred under dry argon during one day at –20° C.

The mixture was cooled to –35° C. (±2° C.) using a dry ice/$CCl_4$/acetone bath. The anhydrous cuprous chloride (1.18 g, 12 mmol) was added and the mixture was stirred over a period of 0.5 h.

C. Addition of Grignard reagent

After 0.5 h, using the same apparatus mentioned above (Ar, –35° C.), a solution of 17β-acetoxy estra-4,6-diene-3-one (3) (32.0 g, 102 mmol) in dry THF (300 ml) was added dropwise over a period of 6 h to the Grignard reagent (red coloration appeared and disappeared). The mixture was stirred for an additional 1 h and, after removal the cooling bath, acidified (about 0° C.) with acetic acid (40 ml), diluted with water and extracted with ether (3x). The ether solution was washed with a saturated sodium bicarbonate solution and water. The organic layer was dried over anhydrous magnesium sulfate and evaporated under reduced pressure to dryness.

The residue was dissolved in MeOH (660 ml) and 5N HCl (180 ml), refluxed for 1 h and 45 min, then concentrated under reduced pressure and cooled in an ice bath. The mixture was then filtered to remove the white precipitate. After the solution had been diluted with water and extracted with methylene chloride (3x), the organic layer was dried over anhydrous $MgSO_4$ and evaporated under reduced pressure to dryness. Finally, the product (55.9 g, brown old was chromatographed on silica gel (Kieselgel 60F254, Merck, 0.063–0.200 mm, 1500 g). Elution with mixtures of methylene chloride and ethyl acetate (4:1 to 1:2 v/v) and then pure ethyl acetate gave crude 7α-(11'-hydroxy-undecyl)-17β-hydroxy estra-4-en-3-one (34.8 g) which was dissolved in dry pyridine (200 ml) and dry acetic anhydride (200 ml), stirred 17 h at room temperature and then poured in ice-water. The product was extracted with methylene chloride (3X), washed with 1N hydrochloric acid, water, saturated sodium bicarbonate and water (3X), dried on anhydrous magnesium sulfate and filtered. After evaporation of solvent, the mixture (35 g) of 7α- and 7β-diacetoxyenones and degradation products of Grignard reagent were separated by flash chromatography on silica gel (Kieselgel 60, Merck, 230 mesh ASTM, 2.0 kg) developed with a mixture of hexane and diethyl ether (2:3 v/v). The first product eluted was pure amorphous 7α-(11'-acetoxy undecyl) 17β-acetoxy-estra-4-en-3-one (4) (20.8 g, 39.4 mmol, yield from dienone was 39.0%). Further elution gave the 7β-isomer (5) (5.4 g, 10.3 mmol, 10%). All structures were determined by spectroscopic means.

7α-(11'-hydroxy-undecyl) estra-1,3,5(10)-trien-3,17β-diol (6a)

Under dry argon, a solution of 7α-(11'-acetoxy undecyl) 17β-acetoxy-estra-4-en-3-one (4) (17.0 g, 32.4 mmol) in dry acetonitrile (150 ml) was added rapidly to a suspension of cupric bromide (14.8 g, 66.2 mmol) and mmol) and lithium bromide (2.89 g, 33.6 mmol) in warm acetonitrile (75 ml). The mixture was heated to reflux over a period of 30 min and stirred vigorously, and then cooled to room temperature. A saturated aqueous solution of sodium bicarbonate (50 ml) was added, and then the organic compound was extracted with ethyl acetate (3×150 ml). The organic layers were washed with water, dried over anhydrous magnesium sulfate, filtered and evaporated under vacuum to dryness. The residue was chromatographed on silica gel (Kieselgel 60F254 Merck 0.063–0.200 mm; 1000 g). Elution with hexane-ethyl acetate (1:1 v/v) gave the 7α-(11'-acetoxy-undecyl) estra-1',3',5'(10')-trien-3,17β-diol, 17β-acetate (6b) (8.51 g; 50.3%) and the starting product (1.33 g; 15%).

The above diacetate phenol (8.51. g, 16.2 mmol) was dissolved in methanol (90 ml) and sodium hydroxyde 30% (w/v) (9 ml). The mixture was refluxed for 90 min under dry nitrogen. The solution was then concentrated under vacuum and diluted with hydrochloric acid (10%, v/v). The mixture was extracted using ethyl acetate (4×150 ml) and the ethyl acetate extract was washed with water, dried over anhydrous magnesium sulfate, filtered and evaporated under vacuum. The evaporation gave 7α-(11'-hydroxy undecyl) estra-1,3,5 (10)-trien-3,17β-diol (6a) (6.99 g, 98% brut) as a yellow foam, the structure of which was confirmed by spectroscopic means.

3-benzoyloxy 7α-(11'-hydroxy undecyl) estra-1,3,5(10)-trien-17β-ol (7)

The above triol (6.99 g; 15.8 mol) was dissolved in acetone (25 ml) and an aqueous solution of sodium hydroxyde (1N, 19.1 ml). The mixture was cooled to 0° C. using an ice/water bath. Benzoyl chloride (2.22 ml, 19.1 mmol) was then added dropwise. The mixture was stirred for 40 min at 0° C. and then diluted with water. The solution was extracted using ethyl acetate (3X) and the organic layers were washed with a saturated aqueous solution of sodium bicarbonate and finally with water. The ethyl acetate solution was dried over anhydrous magnesium sulfate, filtered and evaporated under vacuum to dryness. Then, the residue was immediately chromatographed on silica gel (Kieselgel, 60F254, 0.063–0.200 mm; 500 g). The chromatography was carried out, first, using methylene chloride as solvent (about 1 liter) and secondly the pure 3-benzoyloxy 7α-(11'-hydroxy undecyl) estra-1,3,5(10)-trien-17β-ol (7), colorless oil (6.50 g, 75%) was eluted with methylene chloride-ethyl acetate (5:1 about 1 liter and 4:1; v/v). The structure was confirmed by spectroscopic means.

11-(3-benzoyloxy-17'-oxo-estra-1',3',5'(10)-trien-7'α-yl) undecanoic acid (8)

To a cooled solution of 3-benzoyloxy-7α-(11'-hydroxy undecyl)estra-1,3,5(10)-trien-17α-ol (7) (4.3 g) in acetone (100 ml) was added dropwise Jone's reagent (8N-chromic acid solution, 6.7 ml). After 30 min, isopropanol (40 ml) was added and the mixture was concentrated under vacuo. Water was added and the mixture was extracted four times with ethyl acetate. The organic layers were washed twice with brine, dried over magnesium sulfate and evaporated to dryness. The crude 11-(3'-benzoyloxy-17'-oxo-estra-1',3',5' (10')-trien-7'α-yl) undecanoic acid (8) (3.94 g) was used in the next step without purification.

Scheme 8

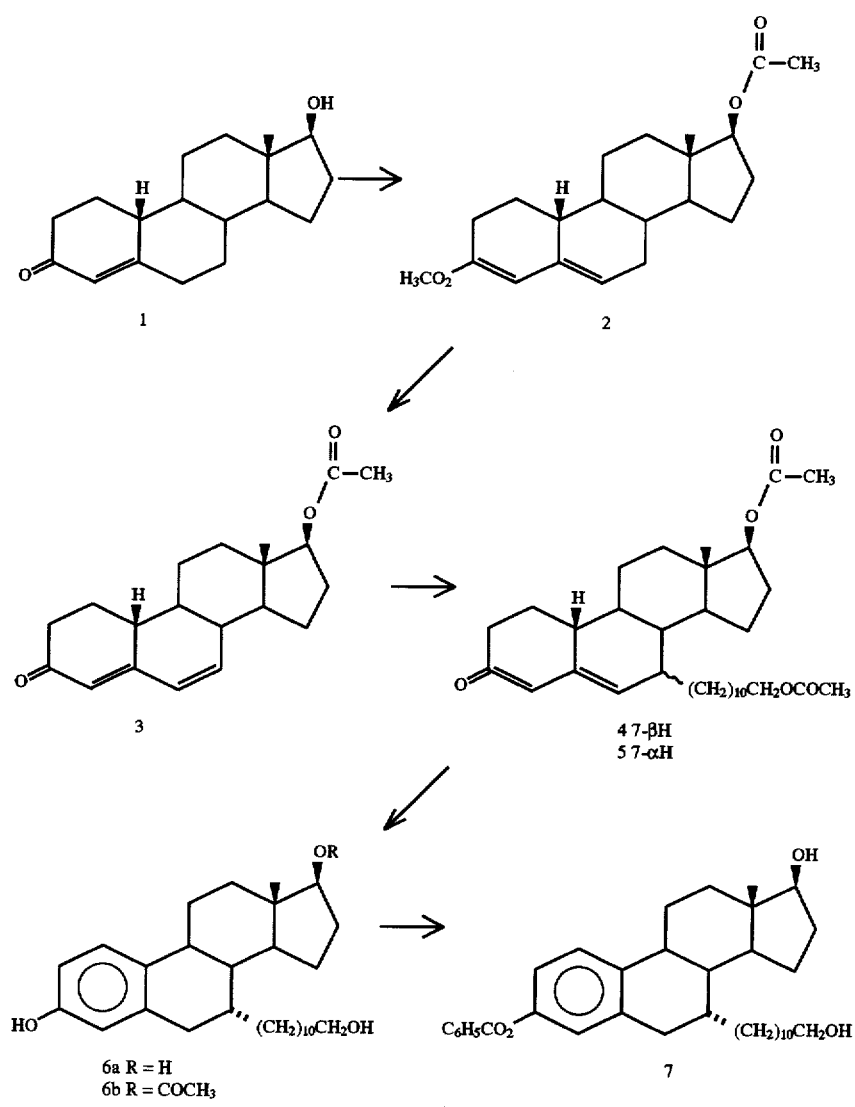

-continued
Scheme 8

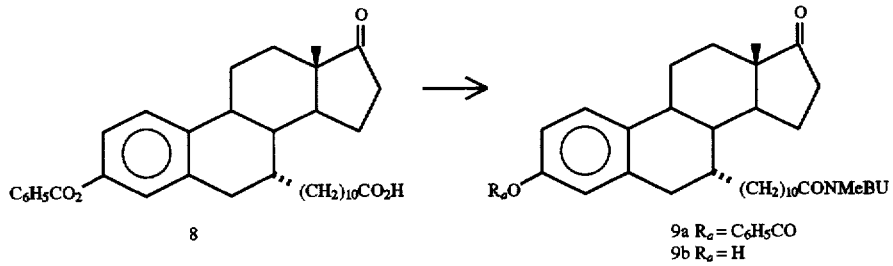

8

9a R_a = C_6H_5CO
9b R_a = H

N-n-butyl,n-methyl-11-(3'-hydroxy-17'-oxo-estra-1',3',5' (10')-trien-7'α-yl) undecanamide (9b)

To 11-(3'-benzoyloxy-17'-oxo-estra-1',3',5'(10')-trien-7'α-yl) undecanoic acid (8) (3.94 g, 7.22 mmol), dissolved in anhydrous $CH_2Cl_2$ (100 ml) and cooled at −10° C. was added tributylamine (2.18 ml, 9.15 mmol) and isobutylchloroformate (1.30 ml, 10.0 mmol). The solution was stirred during 35 min. and N-methylbutylamine (13 ml, 109.7 mmol) was added. The mixture was warmed to room temperature and stirred during 1 h. Afterward, $CH_2Cl_2$ was added and the organic phase was washed with 1N HCl, water, saturated sodium bicarbonate solution and finally with water, dried with anhydrous $MgSO_4$ and the solvent was removed under reduced pressure. The residue was purified by chromatography on silica gel. Elution with mixture of EtOAc/hexane (1.5:8.5 v/v) yielded N-butyl, N-methyl-11-(3'- benzoyloxy-17'-oxo-estra-1',3',5'(10')-trien-7'α-yl) undecanamide (9a) (4.25 g, 96%) as colorless oil; IR v (neat) 1750, 1725 and 1640 $cm^{-1}$. The above described benzoyloxy amide (341 mg, 0.54 mmol) was dissolved in methanol (10 ml) and cooled at 0° C. Following this 2N NaOH (5 ml) was added and the mixture was stirred during 60 min. at 0° C. The solution was neutralized with 1N HCl and extracted with $CH_2Cl_2$. The organic phase was dried with anhydrous $MgSO_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo,estra-1',3',4'(10)-trien-7'α-yl) undecanamide (9b) (284 mg, 97%) as colorless oil; $^1$H-NMR δ ($CDCl_3$) 0.91 (s,3H,18'—$CH_3$), 2.76 app(d,1H,J=16.3 Hz, part of ABX system, 6'—H) 2.96 and 2.98 (2s,3H, N—$CH_3$), 3.27 and 3.38 (2$t_{app}$, 2H,J=7.5 Hz,N—$CH_2$—) 16.63 (broad s, 1H,4'—H), 6.70 (broad d,1H, J=8.5 Hz,2'—H), 7.12 (d,1H, J=8.4 Hz,1'—H); IRv$_{max}$ (neat) 3270, 1730, 1615 $cm^{-1}$; MS m/e 523 ($M^+$, 100%), 508 ($M^+$—$CH_3$, 32%), 142 ($C_2H_4CON(CH_3)C_4H_9^+$, 47%).

16-HALO-ESTRADIOL UNDECANAMIDE (SCHEME 9)

N-n-butyl,N-methyl-11-(3',17'β-diacetoxy-estra-1',3',5' (10'),16'-tetraen-7α-yl) undecanamide (10)

The ketone amide 9b (163 mg, 0.50 mmol) was dissolved in isoprenyl acetate (10 ml). p-toluenesulfonic acid (44 mg) was then added and the solution was distilled to about two-thirds of the original volume in 7 h and was then stirred at reflux for 12 h. Afterwards, the solution was cooled with an ice-water bath and extracted with 50 ml of cooled ether. The ether was washed with a cooled satured sodium bicarbonate and water. The organic phase was dried with anhydrous $MgSO_4$ and the solvent was removed under reduced pressure. The residue was filtered through alumina (15 mm×50 mm alumina Woehlm neutral, activity II) using a mixture of benzene-diethyl ether (3:7 v/v/) as eluant. The solvent was removed under reduced pressure and, the residue was purified by flash chromatography on silica gel. Elution with mixture of EtOAc/hexane (1:4 v/v) yielded the N-butyl, N-methyl-11-(3',17'β-diacetoxy-estra-1',3',5'(10'), 16'-tetraen-7'α-yl) undecanamide (10) (244 mg, 80%) as colorless oil; $^1$H-NMR δ ($CDCl_3$) 0.92 (s,3H,18'—$CH_3$), 0.92 and 0.95 (2t,3H-3',J=7.0 Hz,N($CH_2$)$_3CH_3$), 2.18 (s,3H, 17'—OCOCH$_3$), 2.28 (s,3H'—OCOCH$_3$), 2.76 app (d,1H, J=16.1 Hz, part of ABX system,6'H), 2.90 and 2.96 (2s,3H, N—$CH_3$), 3.26 and 3.35 (2$t_{app}$,2H,J=7.6 Hz,N—$CH_2$—), 5.52 (m, 1H,16'—H), 6.80 (broad s,1H,4'—H), 6.85 (dd,1H, $J_1$=9.1 Hz and $J_2$=3.0 Hz,2'—H), 7.27 (d,1H,J=9.1 Hz,1'—H); IR v$_{max}$(neat) 1750, 1635, 1200 $cm^{-1}$; MS m/e 607 ($M^+$,2%) 5($M^+$—$COCH_2$,100%), 550 ($M^+$—$COCH_2$—$CH_3$, 13%), 523 ($M^+$—$2COCH_2$, 45%), 142 ($C_2H_4CON(CH_3)C_4H_9^+$,55%), 129 ($C_4H_9(CH_3)NCOCH_3^+$,38%), 114 ($C_4H_9(CH_3)NCO^+$, 60%), 86 ($C_4H_9(CH_3)N^+$, 25%), EXACT MASS calcd for $C_{38}H_{57}O_5N$ 607.4239. found 607.4234.

N-butyl, N-methyl-11-(16'α-chloro-3'acetoxy-17'-oxo-estra-1',3',4'(10')-trien-7'α-yl) undecanamide (11, X=Cl)

To diacetate amide 10, dissolved in 5 ml of acetone, was added a solution of sodium acetate (2.6 equivalents) in acetic acid and water (1:11.3 v/v) and then, was treated with tertbutyl hypochlorite (1 eq.) prepared from t-butanol (4 ml) and Javel water (Javex 6.1%, 50 ml). The dear solution was warmed to 55° C. and stirred for 1 h. Afterwards, the solvent was evaporated to dryness. The residue was dissolved in ether (100 ml) and water was added (20 ml). The organic phase was washed with water, dried with anhydrous $MgSO_4$ and evaporated to dryness. The residue was purified by chromatography on silica gel carried out with mixture of EtOAc/hexane (3:7 v/v) to give the N-butyl, N-methyl-11-(16'α-chloro-3'-acetoxy-17'-oxo-estra-1,',3',4'(10')-trien-7'α-yl) undecanamide 11, X=Cl) (115 mg, 89%) as colorless oil; $^1$H-NMR δ ($CDCl_3$) 0.92 and 0.95 (2t,3H,J=7.0 Hz,N($CH_2$)$_3CH_3$), 0.96 (s,3H,18'—$CH_3$), 2.28 (s,3H,3'—OCOCH$_3$), 2.80 app (d,1H,J=16.6 Hz, part of ABX system, 6'—H) 2.90 and 2.96 (2s,3H,N—$CH_3$), 3.24 and 3.35 (2$t_{app}$, 2H,J=7.4 Hz,—N—$CH_2$—), 4.46 (d,1H,J=6.6 Hz,16'β—H), 6.82 (broad s,1H,4'—H), 6.86 (dd, 1H,J=9.1 Hz and $J_2$=,2.6 Hz,2'—H), 7.29 (d,1H,J=9.1 Hz,1'—H); IR v$_{max}$ (neat 1750, 1640, 1205 $cm^{-1}$; MS m/e 601, 599 ($M^+$24%, 68%), 142 ($C_2H_4CON(CH_3)C_4H_9^+$,100%) 114 ($C_4H_9(CH_3)NCO^+$, 93%).

N-butyl,N-methyl-11-(16'α-chloro-3',17'-dihydroxy-estra-1'3',5'(10')-trien-7'α-yl) undecanamide ("EM 139") and ("EM 170")

A stirred solution of haloketone amide (11, X=CL) in anhydrous tetrahydrofuran (THF) (10 ml) under argon was chilled to −70° C. with 2-propanol/dry ice bath. A solution of 1.0M of lithium aluminium hybride (2 eq.) was then added dropwise. After 30 min, the reaction was allowed to return slowly at 0° C. for 5 min, then was quenched by the dropwise addition of a mixture of THF-EtOAc (5 ml) (1:1 v/v) and acidified at pH~4 with (10%) HCl. The mixture was stirring for 5 min at room temperature and then extracted with EtOAc. The organic phase was washed with water, dried on anhydrous $Na_2SO_4$ and evaporated under reduced pressure. The residue was chromatographed on silica gel with a mixture of EtOAc/hexane (4:6 v/v) as eluant:

N-butyl, N-methyl-11-(16'α-chloro-3',17'α-dihydroxy-estra-1',3',5'(10')-trien-7'α-yl) undecanamide ("EM 170")

(15 mg, 29%) as colorless oil; analytical sample was obtained by HPLC purification; $^1$H-NMR δ ($CDCl_3$, 400 MHz) 0.79 (s,3H,18'—$CH_3$), 0.93 and 0.96 (2t, 3H,J=7.3 Hz,N($CH_2)_3CH_3$), 2.80 (2H,$J_{6,6}$=17.1 Hz and $J_{6,7}$=4.5 Hz, Δδ=24.34 (Hz, system ABX, 6'—H), 2.94 and 2.99 (2s, 3H,N—$CH_3$), 3.26 (dd,$J_1$=7.6 Hz and $J_2$=7.4 Hz) and 3.32–3.43 (m)-[2H,—N—$CH_2$—], 3.71 (d,1H,J=4.5 Hz,17'β—H), 4.63 (ddd, 1H, $J_{16,15}$=10.2 Hz, $J_{16,17}$=4.5 Hz and $J_{16,15}$ 3.9 Hz, 16'β—H), 6.50 (d, 1H, J=24 Hz, 3'—OH), 6.60 (d, 1H,J=2.5 Hz, 4'—H), 6.66 (dd,1HJ_1=8.4 Hz and $J_2$=2.5 Hz, 2'H), 7.14 (d,1H,J=8.5 Hz, 1'—H); $IRv_{max}$(neat) 3300, 1615, 1495 $cm^1$; MS m/e 561,559 ($M^+$, 40%, 100%), 523 ($M^+$-HCl, 20%), 142 ($C_2H_4CON(CH_3)C_4H_9^+$, 44%), 114 ($C_4H_9(CH_3)CNO^+$, 37%); Exact mass calculated for $C_{34}H_{54}O_3N^{35}Cl$ 559.3785, found 559.3821.

- and -

-N-butyl, N-methyl-11-(16'α-chloro-3',17'β-dihydroxy-estra-1'3'5'(10')-trien-7'α-yl) undecanamide ("EM 139")

(25 mg, 55%) as a colorless oil; analytical sample was obtained by HPLC purification; 1H-NMR δ ($CDCl_3$, 400 MHz), 0.81 (s,3H, 18'—$CH_3$), 0.93 and 0.96 (2t, 3H,J=7.3 Hz, ($CH_2)_3CH_3$), 2.78 2H, $J_{6,6}$=16.2 Hz and $J_{6,7}$=4.5 Hz, Δδ=24.34 Hz, system ABX, 6'—H), 2.94 and 2.99 (2s, 3H, N=$CH_3$), 3.27 (dd, $J_1$-7.6 Hz and $J_2$-75.5 Hz) and 3.31–3.45 (m, 2H, —N—$CH_2$), 3.86 (dd, 1H, $J_{17,17}$-OH=3.4 Hz and $J_{17,16}$=5.9 Hz, 17'α-H), and 4.11 (ddd, 1H, $J_{16,15}$=10.8 z $J_{16,17}$=5.9 z and $J_{16,15}$=2.5 Hz, 16'β—H), 6.56 (d, 1H, J=19.7 Hz, 3'—OH), 6.61 (d, 1H, J=2.5 Hz, 4'—H), 6.66 (dd, 1H, $J_1$=8.4 Hz and $J_2$=2.6 Hz, 2'—H), 7.13 (d, 1H, J=8.4 Hz, 1'—H); IR $v_{max}$(neat) 3320, 1615, 1490 $cm^1$; MS m/e 561,559 ($M^+$, 38%, 100%), 523 ($M^+$13 HCl, 16%), 142 ($C_2H_2CON(CH_3)C_4H_9^+$, 80%), 114($C_4H_9(CH_3)NCO^+$, 76%), exact mass calculated for $C_{34}H_{54}O_3N^{35}Cl$ 559.3754, found 559.3825.

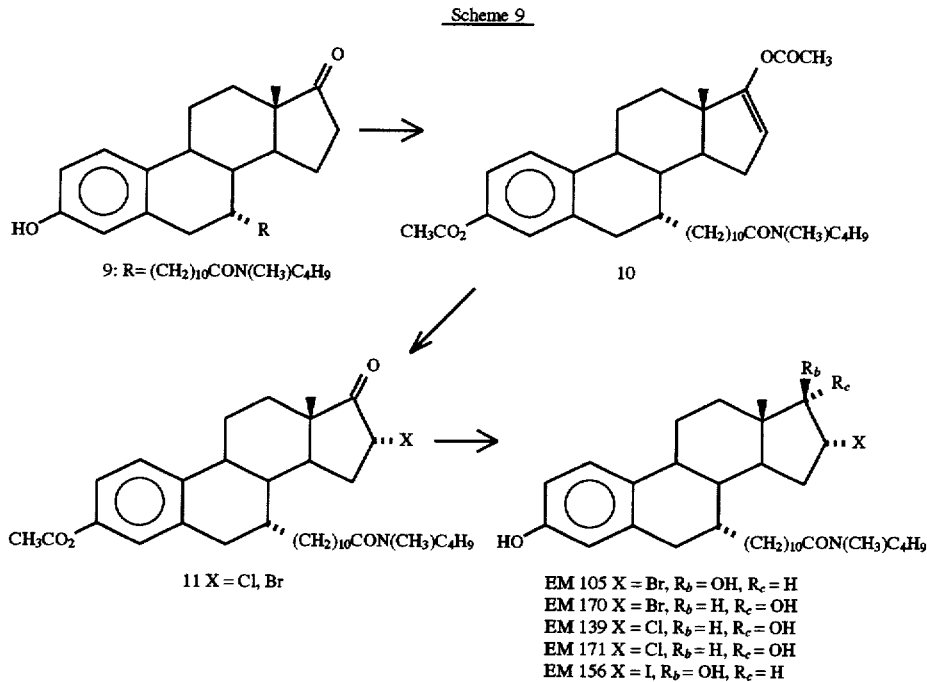

Scheme 9

9: R=(CH_2)_{10}CON(CH_3)C_4H_9

10

11 X = Cl, Br

EM 105 X = Br, $R_b$ = OH, $R_c$ = H
EM 170 X = Br, $R_b$ = H, $R_c$ = OH
EM 139 X = Cl, $R_b$ = H, $R_c$ = OH
EM 171 X = Cl, $R_b$ = OH, $R_c$ = OH
EM 156 X = I, $R_b$ = OH, $R_c$ = H

N-n-butyl, N-methyl-11-(16'α-bromo-3'-acetoxy-17'-oxo-estra-1',3',5'-(10'), trien-7'α-yl) undecanamide (11, X=Br)

To the above diacetate 10 (244 mg, 0.40 mmol) dissolved in 10 ml of acetic add was added dropwise with stirring within 10 minutes and at room temperature, a brominating solution composed of 50 mg (0.6 mmol) of sodium acetate, 1.6 ml of acetic acid, 0.04 ml of water and 63.9 mg (0.02 ml, 0.40 mmol) of bromine. During the course of this reaction, a red coloration appeared and disappeared. To the solution, 50 ml of ether was added and the organic phase was washed with water (4×50 ml) followed by a saturated sodium bicarbonate solution (2×50 ml) and finally with water (3×50 ml. The combined phase was dried over anhydrous magnesium sulfate and the solvent was removed in vacuo. The residue was chromatographed on silica gel (Kieselgel, 60F254, Merck, 0.063–0.200 mm). Elution with a mixture of hexane-ethyl acetate (4:1 v/v) yielded N-butyl, N-methyl-11(16'α-bromo-3'-acetoxy-17'-oxo-estra-1',3',5'(10'), trien-7'-α-yl) undecanamide (11, X=Br) (201 mg, 78%), as colorless oil; $^1$H-NMR δ ($CDCl_3$), 0.94 (s,3H,18'—$CH_3$), 2.28 (s, 3H, 3'-OCOCH_3), 2.82 app (d,1H,J=16.4 Hz, part of ABX system, 6'—H), 2.90 and 2.96 (2s, 3H,H—$CH_3$), 3.24 and 3.35 (2t_{app},2H, J=7.7 Hz, —N—$CH_2$—)d, 4.58 (t,1H, J=3.6 Hz, 16β—H), 6.82 (broad s,1H,4'—H), 6.88 (dd, 1H, J=8.0 Hz and $J_2$=4.0 Hz, 2'—H), 7.29 (d, 1H,J=8 Hz, 1'—H); MS m/e 644 ($M^+$,7%), 565 ($M^+$—Br, 7.77%), 522 ($M^+$—Br—$COCH_2$, 55%), 142 ($C_2H_4CON(CH_3)C_4H_9^+$0.67%), 114 ($C_4H_9(CH_3)NCO^+$,66%), 88 (100%).

N-butyl, N-methyl-11-(16'α-bromo--3',17'-dihydroxy-estra-1',3',4'(10')-trien-7'α-yl) undecanamide ("EM 105") and ("EM 171").

A solution of bromoketone amide 11 (X=Br) (295 mg, 0.46 mmol) in anhydrous tetrahydrofuran (10 ml) under argon was chilled to −70° C. and a solution of 1.0M of lithium aluminium hybride in ether (0.92 ml, 0.92 mmol) was added dropwise with rapid magnetic stirring. After 30 min, the reaction was quenched by the dropwise addition of a mixture of THF-ethyl acetate (1:1 v/v) and acidified by 10% hydrochloric acid. The mixture was stirring for 5 min at room temperature and then extracted with ethyl acetate. The organic phase was washed with water, dried on anhydrous sodium sulfate and evaporated to dryness under reduced pressure. The residue was purified by chromatography on silica gel. Elution with a mixture of hexane-ethyl acetate (7:3 v/v) gave:

N-n-butyl, N-methyl-11-(16'α-bromo-3',17'α-dihydroxy-estra-1',3',5'(10')-trien-7'α-yl) undecanamide ("EM 171")

(63 mg, 21%) as colorless oil; $^1$H-NMR δ ($DCDl_3$, 400 MHz) 0.81 (s, 3H,18'—$CH_3$), 0.93 and 0.96 (2t, 3H,J=7.3 Hz,$N(CH_2)_3CH_3$), 2.79 (2H,$J_{6,6}$=16.6 Hz, $J_{6,7}$=4.7 Hz, =Δδ= 24.34 Hz, system ABX,6'—H), 2.94 and 2.99 (2s,3H,N—$CH_3$), 3.27 (dd,2H,$J_1$=7.7 Hz and $J_2$=7.5 Hz, —N $CH_2$—), 3.31–3.44 (m,2H.—N—$CH_2$—), 3.66 (dd,1H,$J_{17,17}$=1.4 Hz, $J_{17,16}$=4.3 Hz, 17'β—H), 4.68 (dt,1H,$J_{16,17}$=4.3 Hz, m, $J_{16,15}$=9.7 Hz, 16'β—H), 6.60 (d, 1H,J=2.4 Hz, 4'—H), 6.65 (dd, 1H,J=8.5 Hz and $J_2$=2.5 Hz, 2'—H), 7.14 (d,1H,J=8.5 Hz, 1'—H); $IRv_{max}$ (neat) 3300, 1615, 1495 $cm^{-1}$; MS m/e 605,603 ($M^+$, 17%), 523 ($M^+$—HBr, 81%), 142 ($C_2H_4CON(CH_3)C_4H_9^+$, 100%), 114 ($C_4H_9(CH_3)NCO^+$, 97%); Exact mass calculated for $C_{34}H_{54}O_3N^{79}Br$ 603.8289, found 603.3304.

- and -

N-n-butyl, N-methyl-11-(16'α-bromo-3', 17'β-dihydroxy-estra-1',3',-5'(10')-trien-7α-yl) undecanamide ("EM 105").

(170 mg, 50%) as a colorless oil; analytical sample was obtained by HPLC purification; $^1$H-NMR δ ($CDCl_3$, 400 MHz), 0.80 (s, 3H,18,—$CH_3$), 0.93 and 0.96 (2t,3H,J=7.3 Hz, $N(CH_2)_3CH_3$), 2.80 (2H,$J_{6,6}$=16.4,$J_{6,7}$=4.6 Hz, Δδ=24.34 Hz, system ABX, 6'—H), 2.94 and 2.99 (2s,3H, N—$CH_3$), 3.27 (dd,2H,$J_1$=7.7 Hz and $J_2$=7.5 Hz, —N—$CH_2$—), 3.31–3.45 (m,2H,—N—$CH_2$—), 4.02 (dd, 1H,$J_{17,17}$=3.7 Hz, and $J_{17,16}$=6.1 Hz, 17'α—H), 4.15 (ddd, 1H,$J_{16,15}$=10.2 Hz, $J_{16,17}$=6.1 Hz and $J_{16,15}$=2.9 Hz, 16'β—H), 6.61 (d,1H,J=2.5 Hz, 4'—H), 6.66 (dd,1H,J=8.4 Hz and $J_2$ 2.5 Hz, 2'—H), 7.12 (d,1H,J=8.4 Hz, 1'—H); IR $v_{max}$ (neat) 3320, 1610, 1490 $cm^{-1}$; MS m/e 605, 603 ($M^+$, 29%), 523 ($M^+$—HBr, 100%), 142 ($C_2H_4CON(CH_3)C_4H_9^+$,70%), 114 ($C_4H_9(CH_3)NCO^+$, 60%); Exact mass calculated for $C_{34}H_{54}O_3N^{79}Br$ 603.3289 found 603.3289.

N-butyl, N-methyl-11-(16'α-iodo-3',17'β-dihydroxy-estra-1',3',5'(10')-trien-7α-yl) undecanamide ("EM 156").

Under argon atmosphere, a mixture of 16α-bromodiol EM 105 (55 mg, 0.091 mmol) and dry sodium iodide (136 mg, 0.91 mmol) in freshly ethyl methyl ketone (25 ml) was refluxed in darkness during 12 h. Afterwards, the solvent was evaporated, water was added and the product was extracted with ethyl acetate. The organic phase was washed with 5% sodium thiosulfate and with water, dried over anhydrous sodium sulfate and concentrated to dryness under reduced pressure. The residue was purified by chromatography. Elution with a mixture of hexane-ethyl acetate (1:1, v/v) gave a mixture of starting material and iodo compound (52:48) of which HPLC separation afforded N-butyl, N-methyl-11,(16'-α-iodo-3',17'β-dihydroxy-estra-1',3',5' (10')-trien-7'α-yl) undecanamide ("EM 156") (21 mg, 36%) as colorless oil; $^1$H-NMR δ ($CDCl_3$, 400 MHz) 0.78 (s,3H, 18'—$CH_3$), 0.93 and 0.96 (2t,3H,J=7.3 Hz, $N(CH_2)_3CH_3$), 2.79 (2H,$J_{6,6}$=16.5 Hz,$J_{6,7}$=4.4 Hz,Δδ,=24.34 Hz, system ABX, 6'—H), 2.94 and 2,99 (2s,3H,N—$CH_3$), 3.27 (dd,2H, $J_1$-7.6 Hz and $J_2$-7.5 Hz, —N—$CH_2$) 3.32–3.44 (m, 2H N—$CH_2$), 4.09–4.17 (m, 2H, 16'βH and 17α-H), 6.60 (d,1H,J=2.4 Hz, 4'—H), 6.65 (dd,1H,J=8.4 Hz and $J_2$-2.4 Hz, 2'—H), 7.13 (d,1H,J=8.4 Hz, 1'—H); IR v(neat)3310, 1610, 1490 $cm^{-1}$; MS m/e 651 ($M^+$,8%), 523 ($M^+$—HI, 100%), 508 ($M^+$—HI—$CH_3$,38%) 142 ($C_2H_4CON(CH_3)C_4H_9^+$, 54%), 114 ($C_4H_9(CH_3)NCO^+$, 49%); Exact mass calculated for $C_{34}H_{54}O_3HI$—HI 523.4028, found 523.4028.

EFFICACY OF AN ANTIESTROGEN SYNTHESIZED IN ACCORDANCE WITH EXAMPLE 9

Compound "EM 139" shown in Scheme 9 above is an estrogen activity inhibitor. "EM 139" has been tested both for efficacy in acting as an antiestrogen by blocking estrogen receptors without substantially activating those receptors (see FIG. 3), and for efficacy in inhibiting 17β-hydroxysteroid dehydrogenase (see FIG. 4), an enzyme which catalyzes reactions involved in the synthesis of both androgens and estrogen (hereinafter referred to as "17β-HSD")

The antiestrogenic activity of "EM 139" was measured as its ability to inhibit the estradiol-induced stimulation of uterine weight in adult female ovariectomized Balb/c mice (body weight=19–20 g) sacrificed five days after ovariectomy. "EM 139", and/or estradiol dissolved in ethanol were injected subcutaneously in the appropriate groups in a solution of 0.9% (w/v) sodium chloride and 1% (w/v) gelatin at different concentrations of "EM 139" (as noted along the X axis of FIG. 3). A dosage of 0.2 ml of the foregoing preparation, was administered twice daily, starting on the day of ovariectomy for a total of 9 injections. Estradiol was injected at the dose of 0.01 µg in 0.2 ml, twice daily, starting on the morning after ovariectomy for a total of 8 injections.

Figure 3:
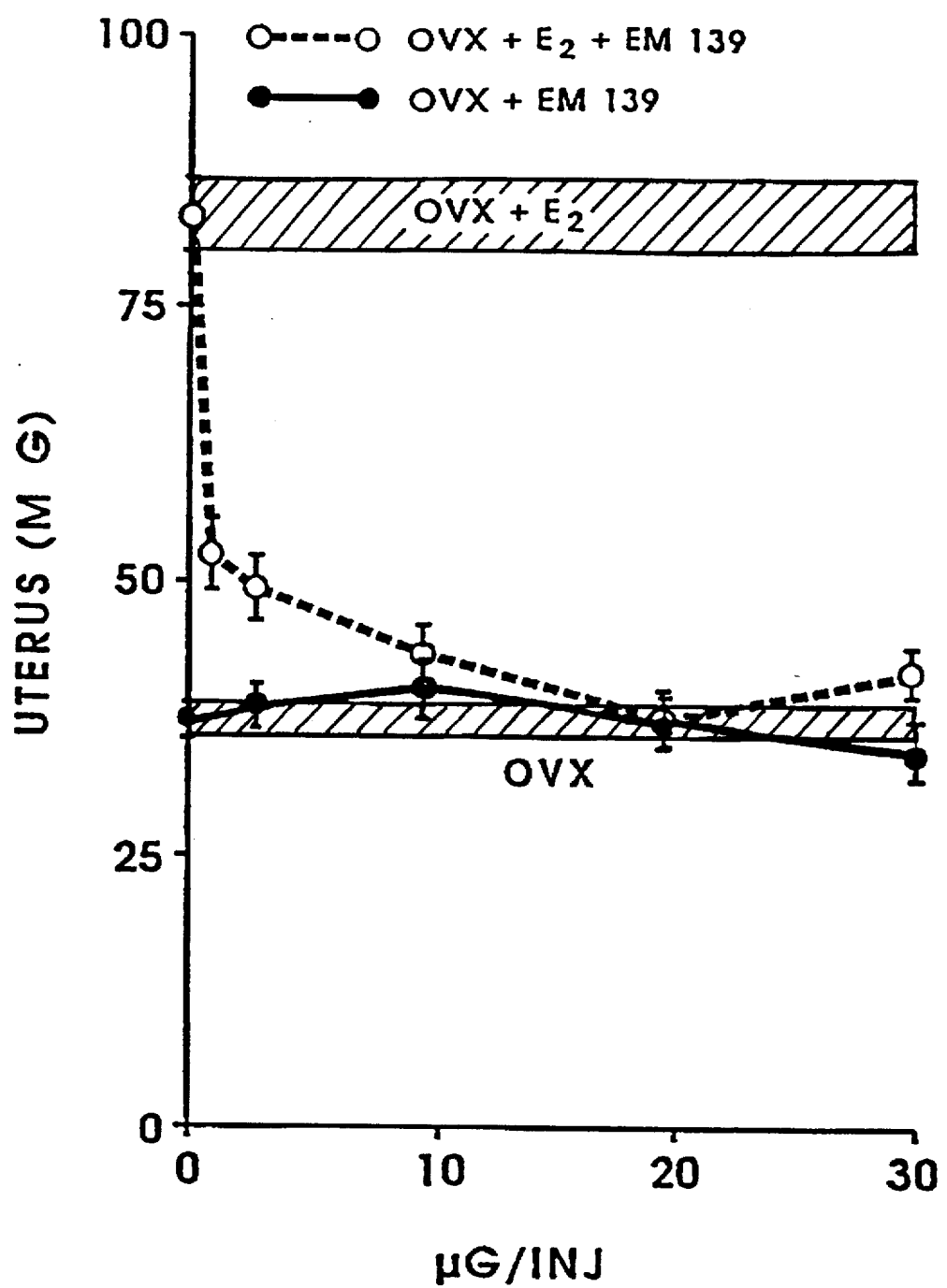
FIG. 3 is a graph illustrating activity of another antiestrogen EM 139. It shows the effect of the administration of EM 139 on uterine weight (mg) in adult ovariectomized mice. The compound was administered twice daily (b.i.d.) at the indicated doses for 4.5 days in the presence or absence of 17β-estradiol (0.01 µg, b.i.d.) via the subcutaneous route.

After sacrifice, the uteri were rapidly removed, freed from fat and connective tissue and weighed. Results shown in FIG. 3 are the means ±SEM of groups of 9–10 mice. As may be seen from FIG. 3, EM 139 was highly effective in reducing estradiol-induced uterine weight gain.

Figure 4:
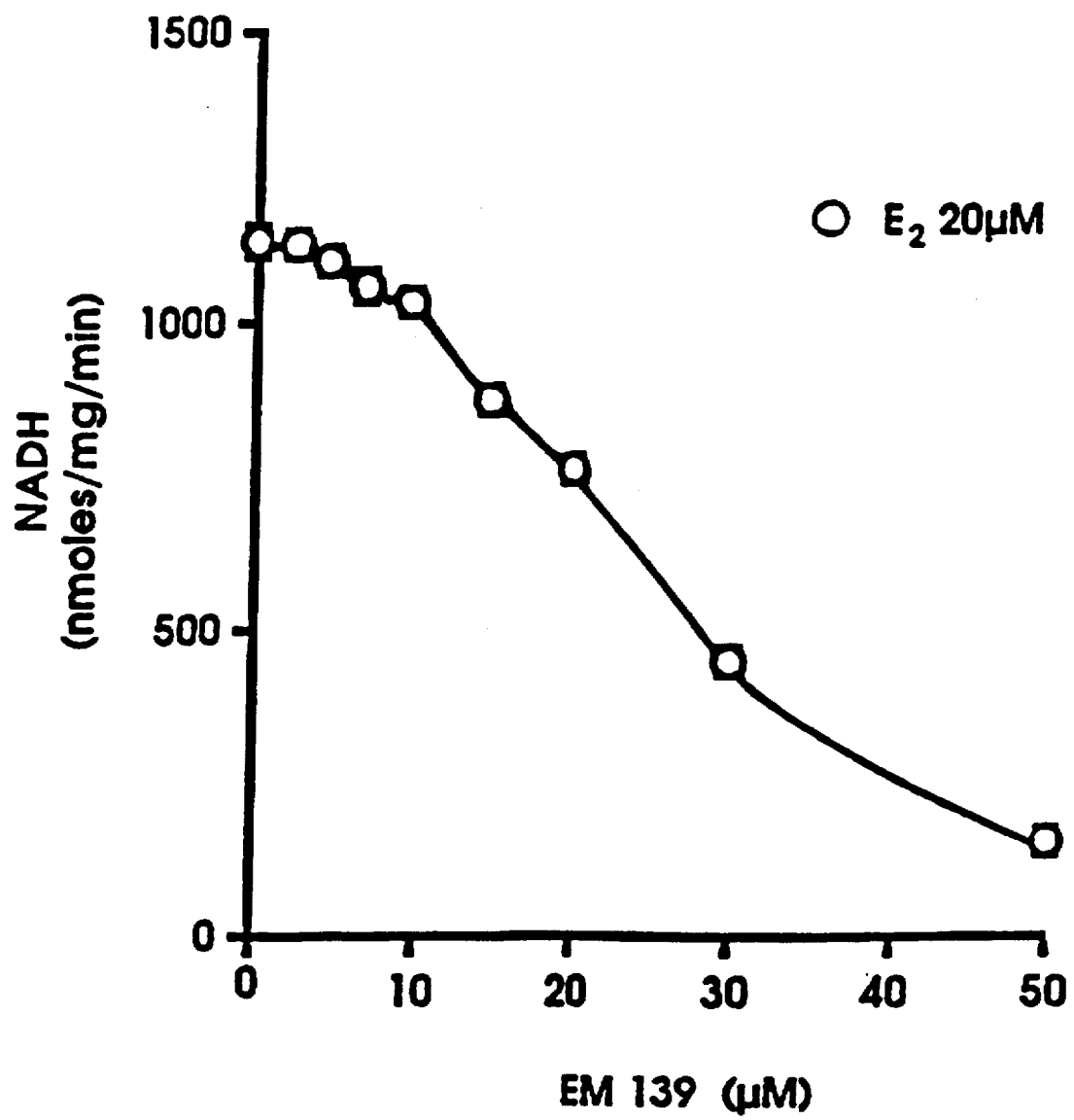
FIG. 4 is a graph illustrating that the antiestrogen which is the subject of FIG. 3 is also a good inhibitor of sex steroid synthesis.

To test the effect of "EM 139" on the inhibition of sex steroid formation, its effect on the 17β-hydroxysteroid dehydrogenase catalyzed conversion of estradiol to estrone was observed. The reaction was followed by monitoring formation of NADH (at 340 nm). The rate of conversion of cofactor NAD to NADH varies directly with the rate of estradiol conversion to estrone. The ability of "EM 139" to inhibit estrone production is indicative of its ability to inhibit the estrogen-forming reverse reaction because both reactions are catalyzed by 17β-hydroxysteroid dehydrogenase (Thomas et al, J. Biol Chem. 258:11500–11504, 1983). 17β-hydroxysteroid dehydrogenase (17β-HSD) was purified to homogeneity from human placenta. A reaction vessel was prepared containing 1 µg 17β-HSD, 5 mM NAD, 20 µM 17β-estradiol, and the concentrations of the test compound "EM 139" which are indicated along the X-axis of FIG. 4 in 1.0 ml of a mixture of Tris-HCl (50 mM), EDTA (2 mM), $NaN_3$ (5 mM). The pH was 7.5. The reaction was allowed to proceed at 25° C. for 15 min. Formation of NADH was measured at 340 nm. As shown by FIG. 4, increasing concentrations of EM 139 significantly inhibited the reaction.

EXAMPLE 10

N-n-BUTYL, N-METHYL-11-(3',17β-DIHYDROXY-17'α-ETHYNYL-ESTRA-(1',3',5'-(10'), 15'-TETRAEN-7'α-YL) UNDECANAMIDE ("EM 123") (SCHEME 10)

N-n-butyl, N-methyl-11-(3'-benzoyloxy-17'α-ethylenedioxy estra-1',3',5'-(10')-trien-7'α-yl) undecanamide (12).

A mixture of N-n-butyl, N-methyl-11-(3'-benzoyloxy-17'-oxo estra-1',3',5'(10')-trien-7'-α-yl) undecanamide (9a) (3.63 g), ethylene glycol (215 ml), p-toluenesulfonic acid (530 mg) and anhydrous benzene (250 ml) was refluxed with a Dean-Stark apparatus during 24 h. After cooling, the mixture was poured in water and extracted three times with ether. The organic layer was washed with a saturated sodium bicarbonate solution, and brine (3x), dried on magnesium sulfate and evaporated to dryness. The residue was purified by flash chromatography on silica-gel (Kieselgel 60, Merck, 230 mesh ASTM, 300 g). Elution with a mixture of hexane-ethyl acetate (6:4 v/v) gave pure N-butyl, N-methyl-11-(3'-benzoyloxy-17'-ethylenedioxy estra-1,3'5'(10'), trien-7'α-yl) undecanamide (3.58 g, 92%) as an oil, the structure of which was confirmed by spectroscopic means.

N-n-butyl, N-methyl-11-(3'-benzoyloxy-16'α-bromo-17'-ethylenedioxy-estra-1' ,3',5'(10') trien-7'α-yl) undecanamide (13)

To the above ethylenedioxy amide 12 (370 mg, 0.55 mmol) in anhydrous tetrahydrofuran (10 ml) cooled at 0° C. was added dropwise under argon, a solution of pyridinium bromide perbromide (406 mg 1.36 mmol) in 7 ml of the same solvent. After stirring during 1.5 h at 0° C., sodium iodide (300 mg) was added and the solution was stirred for 25 min. Afterwards, a solution of sodium thiosulfate (10%, v/v, 10 ml) and pyridine (0.5 ml) was added and the mixture was stirred for an additional 4 h and then poured into water and extracted three times with ether. The organic layers were washed with 1N hydrochloric acid, water, saturated bicarbonate solution and water (3x), dried on magnesium sulfate and evaporated to dryness. The residue was chromatographed on silica-gel (50 g). Elution with a mixture of hexane-ethyl acetate (4:1 v/v) gave pure N-n-butyl, N-methyl-11(3'-benzoyloxy-16'α-bromo-17'-ethylenedioxy-estra-1',3',5'(10'), trien-7'α-yl) undecanamide (13) (313 mg 76%) as colorless oil; IR $v_{max}$ (neat), 1730, 1630, 1595 and 1255 cm$^{-1}$; $^1$H NMR, 0.93 (3H, s, 18'-CH$_3$), 2.28 (2H, td, J=7.5 and 2.6 Hz, —CH$_2$CON—), 2.90 and 295 (3H, 2s, —CH$_3$), 3.24 and 3.35 (2H, 2t, J=7.3 Hz, —N—CH$_2$—), 3.85 and 4.35 (4H, m, —OCH$_2$ CH$_2$O—), 4.56 (1H, m, H—C.16'), 6.91 (1H, d, J=2.2 Hz, H—C.4'), 6.98 (1H, dd, J=8.4 and 2.2 Hz, H—C.2'), 7.32 (1H, d, J=8.4 Hz, H—C.1'), 7.49 (2H, t$_{app}$ J=7.0 Hz H—C.3" and H—C.5"), 7.63 (1H, t$_{app}$, J=7.0 Hz H—C.4" and 8.17 (2H, d, J=7.0 Hz, H—C.2" and H—C.6"), MS m/e, 671 (M+-Br, 11%), 114 (C$_4$H$_9$(CH$_3$) NCO$^+$, 13%), 105 (C$_6$H$_5$$^+$CO+, 100%), 86 (C$_4$H$_9$ (CH$_3$) N$^+$, 10%), 77 (C$_6$H$_5$$^+$, 25%).

N-n-butyl, N-methyl-11-(3'-hydroxy-17'-oxo-estra-1',3',5'(10'), 15'-tetraen-7'α-yl) undecanamide "(EM 112)"

To a solution of the bromoketal (13) (517 mg 0.69 mmol) in anhydrous dimethyl sulfoxide warmed at 73° C., under argon, was added potassium-t-butoxide (1.55 g, 13.8 mmol. The mixture was stirred for 5 h at this temperature and then cooled, poured in ice-water, acidified with 1N hydro-chloric acid and extracted three times with ethyl acetate- The organic layers were washed with water (3x), dried on magnesium sulfate and evaporated to dryness. The residue was dissolved in acetone (30 ml), water (7 ml) and p-toluenesulfonic acid (60 mg) was added. The resulting solution was stirred for 5 h at room temperature and then poured into water. The organic compound was extracted three times with ether, washed with a saturated sodium bicarbonate solution and water (3x), dried on magnesium sulfate and evaporated to dryness. The residue was purified by "flash chromatography" (100 g). Elution with a mixture of hexane-ethyl acetate (1:1 vv) gave the pure N-butyl, N-methyl-11-(3'-hydroxy-17-oxo-estra-1',3',5' (10') ,15'-tetraen-7'α-yl) undecanamide "EM 112" (178 mg 49%) as colorless oil; IR vmax (neat), 3290, 695, 1620 and 1600 cm$^{-1}$; $^1$H NMR, 0.92 and 0.95 (3H, 2t, J=7.3 and 7.0 Hz, —N—(CH$_2$)$_3$ CH$_3$), 1.11 (3H, s, 18'—CH$_3$), 2.32 (2H, td, 1=2.5 and 7.0 Hz, H—C.2), 2.94 and 2.99 (3H, 2s, N—CH$_3$), 3.27 and 3.38 (2H, 2t, J=7.7 and 7.3 Hz,—N—CH$_2$—), 6.11 (1H, dd, J=6.2 and 3.3 Hz, H—C.15'), 6.66 (1H, d, J=2.6 Hz, H—C.4'), 6.71 (1H, dd, J =8.4 and 2.6 Hz, H—C.2'), 7.13 (1H, d, J=8.4 Hz, H—C.1'), 7.60 (1H, dd, J=6.2 and 1.5 Hz, H—C.16') and 7.70 (1H, broad s, w$_{1/2}$=16 Hz, OH), MS m/e, 521 (M$^+$, 53%), 507 (M$^+$—CH$_2$,9%), 506 (M$^+$—CH$_3$,7%), 142 (C$_2$H$_4$ CON (CH$_3$) C$_4$H$_9$$^+$, 25%), 114 (C$_4$H$_9$(CH$_3$)NCO$^+$, 60%) and 86 (C$_4$H$_9$(CH$_3$)N$^+$, 22%, 44 (100%).

N-n-butyl, N-methyl-11-(3',17'β-dihydroxy-17'-α-ethynyl-estra-1'3',5'-(10'),15'-tetraen-7'α-yl) undecanamide ("EM-123")

To hexanes (1 ml) cooled at 0° C., were added trimethylsilylacetylene (0.112 ml), n-butyllithium 1.6M in hexanes (0.25 ml), few drops of anhydrous THF and finally, a slowly addition of a solution of enone amide EM 112 (57 mg) in anhydrous THF (1.2 ml). The mixture was stirred for 30 min at 0° C. After addition of a saturated ammonium chloride solution, the mixture was extracted with ethyl acetate (3x). The organic layers were washed with water and brine, dried over magnesium sulfate and filtered. The solvent was removed under reduced pressure. To the residue (61 mg) dissolved in methanol, a 5N potassium hydroxide solution (0.177 ml) was added and the mixture refluxed for 50 min. After cooling and addition of a saturated ammonium chloride solution, the mixture was extracted three times with ethyl acetate. The organic layers were washed with brine, dried over magnesium sulfate and filtered. The organic solvent was removed under reduce pressure. The residue was chromatographed on silica-gel (5 g). Elution with a mixture of hexanes: ethyl acetate (7:3 v/v) gave N-butyl, N-methyl-11-(3',17'β-dihydroxy-17'α-ethynyl-estra-1'3',5'-(10'),15'-tetraen-7'α-yl)undecanamide ("EM-123") (34 mg, 63%); IR v$_{max}$ (neat), 3290, 2150, 1620 and 1600 cm$^{-1}$; $^1$H NMR, 0.92 and 0.95 (3H, 2t, J=7.3 and 7.0 Hz, N—(CH$_2$)$_3$CH$_3$), 0.95 (3H, s, 18'—CH$_3$), 2.32 (2H, td, J=7.0 and 2. Hz, —CH2CON—), 2.66 (1H, s, —CH), 2.93 and 2.98 (3H, 25, N—CH$_3$), 3.27 and 3.38 (2H, t, J=7.0 Hz, —N—CH$_2$—), 5.78 (1H, dd, J=5.9 and 3.3 Hz, H—C.15'), 6.05 (1H, dd, J=5.9 and 1.5 Hz, H—C.16'), 6.62 (1H, d, J=2.5 Hz, H—C.4'), 6.67 (1H, dd, J=8.4 and 2.6 Hz, H—C.2') and 7.13 (1H, d, J=8.4 Hz, H—C.1') ppm; MS m/e 547 (M$^+$, 12%), 142 (C$_2$H$_4$CON(CH$_3$)C$_4$H$_9$ $^+$, 21%) 114 (C$_4$H$_9$(CH$_3$)NCO$^+$50%), 88 (100%) and 86 (C$_4$H$_9$(CH$_3$)N$^+$, 34%).

EXAMPLE 11

16β-CYCLOPROPYL DERIVATIVES (Scheme 11)

N-n-butyl, N-methyl-11-(17'-oxo-3'-hydroxy-15'β, 16'βmethylene-estra 1',3',5'(10')-trien-7'α-yl) undecanamide (14)

A solution of the phenol-enone EM-112 (101 mg; 0.19 mmol dissolved in anhydrous pyridine (15 ml) and acetic anhydride (10 ml was stirred at room temperature for 20 h. The mixture was into ice-water, then extracted three times with ether. The organic layers were washed with 1N hydrochloric add, water and a saturated sodium bicarbonate solution and water, dried on magnesium sulfate and evaporated to dryness. The residue was purified by "flash chromatography" on silica-gel (20 g). Elution with a mixture of hexane-ethyl acetate (7:3 v/v) gave the N-butyl, N-methyl-11-(17'-oxo-3'-acetoxy-estra-1',3',5'(10'),15'-tetraen-7'α-yl) undecanamide.

To this and palladium (II) acetate (11 mg) in ether (25 ml) an ethereal diazomethane solution (prepared from 1 g of diazaid) was added dropwise at 0° C. with continuous stirring during 10 min. After evaporation, the residue was dissolved in methanol (50 ml) and cooled to 0° C. 2N sodium hydroxide solution (1 ml) was added and after 75 min. of stirring the mixture was neutralized with 1N hydrochloric add, extracted three times with ether. The organic layers were washed with brine, dried on magnesium sulfate and evaporated to dryness. The residue was purified by HPLC to give N-butyl, N-methyl-11-(17'-oxo-3'-hydroxy-15'β, 16'β-methylene-estra-1',3',5'(10')-trien-7'α-yl) undecanamide (14) (79 mg 76%) as a colorless oil. IR $v_{max}$ (neat) 3260, 1705, 1610 and 1570 cm$^{-1}$; $^1$H NMR (400 MHz) 0.93 and 0.96 (3H, 2t, J=7.3 Hz, N(CH$_2$)$_3$CH$_3$), 0.99 (3H, s, 18'-CH$_3$), 1.98 (1H, td, J=8.3 and 3.96 Hz, H-C.161'), 2.80 (1H, d, J=16.6 Hz, Hβ-C.6'), 2.94 and 2.98 (3H, 2s, N—CH$_3$), 3.27 (1H, dd, J=7.58 and 6.66 Hz) and 3.38 (1H, m) (both are —N—CH$_2$—), 6.64 (1H, d, J=2.6 Hz, H—C.4'), 6.66 (1H, dd, J=8.2 and 2.6 Hz, H-C.3') and 210 (1H, d, J=8.2 Hz, H—C.1') ppm; MS m/e 535 (M$^+$, 74%), 522 (M$^+$—CH$_2$, 49%), 129 (C$_4$H$_9$(CH$_3$)NCOCH$_3^+$, 37%), 114 (C$_4$H$_9$(CH$_3$)NCO$^+$, 67% and 88 (100%).

N-n-butyl, N-methyl-11-(3', 17'β-dihydroxy-15'β, 16'β-methylene-estra-1',3',5'(10')-trien-7'α-yl) undecanamide (EM-136)

To the cyclopropylketone 14 (10 mg 18.7 μmol) dissolved in methanol (8 ml) was added sodium borohydride (1.5 mg). The mixture was stirred at room temperature for 18 h. After addition of water, the mixture was concentrated under reduced pressure. The residue was diluted with water and extracted three times with ethylacetate. The organic layers were washed with brine, dried over magnesium sulfate and filtered. The organic solvent was removed under reduced pressure and the residue was purified by "flash chromatography" on silica-gel (5 g). Elution with a mixture of hexanes: ethyl acetate (5:5 v/v) gave N-butyl,N-methyl-11-(3',17'β-dihydroxy-15'β,16'β-cyclopropyl-estra-1',3',5'(10')-trien-7'α-yl) undecanamide ("EM-136"), as a colorless oil, IR $v_{max}$(neat) 300, 1615, 1580 and 1450 cm$^{-1}$, $^1$H NMR (400 MHz), 0.31 (1H, dd, J=14.0 and 7.8 Hz, H—C.1") 0.83 (3H, s, 18'—CH$_3$), 0.93 and 0.96 (3H, 2t, J=7.3 Hz, N(CH$_2$)$_3$CH$_3$), 2.77 (1H, d, J=17.1 Hz, Hβ—C—6'), 2.94 and 2.98 (3H, 2s, N—CH$_3$), 3.27 (1H, dd, J=7.7 and 7.5 Hz) and 3.39 (1H, m) (both are —N—CH$_2$—), 4.09 (1H, broad s, w=10 Hz, H—C.17), 6.64 (21-t, m, H—C.4' and H—C.2') and 7.11 (1H, d, J=8.3 Hz, H-C.1') ppm MS m/e 537 (M$^+$, 18%), 519 (M$^+$—H$_2$O, 56%), 504 (M$^+$—H$_2$O—CH$_3$, 100%), 142 (C$_2$H$_4$CON(CH$_3$)C$_4$H$_9^+$, 70%), 114 (C$_4$H$_9$(CH$_3$)NCO$^+$, 50%) and 86 (C$_4$H$_9$(CH$_3$)N$^+$, 33%).

N-n-butyl, N-methyl-11-(3',17'β-dihydroxy-17'α-ethynyl-15'β,16'β-methylene-estra-1',3',5'(10')-trien-7'α-yl) undecanamide ("EM-138")

To hexanes (500 μl) cooled at 0° C., were added trimethylsilylacetylene (54.6 μl), 1.6M n-butyl lithium in hexanes (120.4 μl), few drops of anhydrous THF and finally, a slowly addition of a solution of the cyclopropyl ketone 14 (25.8 mg) in anhydrous THF (350 μl). The mixture was stirred for 75 min at 0° C. After addition of a saturated ammonium chloride solution (1 ml), the mixture was extracted three times with ethyl acetate. The organic layers were washed and brine, dried over magnesium sulfate and filtered. The solvent was removed under reduced pressure. To the residue dissolved in methanol (900 μl), a 5N potassium hydroxide solution (70 μl) was added and the mixture refluxed for 30 min. After cooling and addition of a saturated ammonium chloride solution (1 ml), the mixture was extracted three times with ethyl acetate. The organic layers were with washed with brine, dried over magnesium sulfate and filtered. The organic solvent was removed under reduced pressure. The residue was purified by "flash chromatography" on silica-gel (5 g). Elution with a mixture of hexanes: ethyl acetate (5:5 v/v) gave N-butyl, N-methyl-11-(3'17'β-dihydroxy-17'α-ethynyl-15'β,16'β-cyclopropyl-estra-1',3',5' (10')-trien-7'α-yl) undecanamide ("EM 138") (12 mg 44%) as a colorless oil; IR $v_{max}$ (neat) 3590, 3300, 1620, 1600 and 1450 cm$^{-1}$; $^1$H NMR (400 MMz), 0.39 (1H, ddd, J=14.6 and 7.9 Hz, H—C.1'), 0.93 and 0.96 (3H, 2t, J=7.4 and 7.3 Hz, -N(CH$_2$)$_3$—CH$_3$), 0.96 (3H, s, 18'-CH$_3$), 2.70 (1H, s, —C CH), 2.77 (1H, d, J=16.5 Hz, Hβ-C.6'), 2.94 and 2.98 (3H, s, N—CH$_3$), 3.27 (1H, dd, J=7.7 and 7.6 Hz) and 338 (1H, m) (both are N—CH$_2$—), 6.42 (1H, m, OH), 6.65 (2H, m, H—C.4' and H—C.2') and 712 (1H, d, J=8.3 Hz, H—C.1') ppm; MS m/e 561 (M$^+$, 15%), 142 (C$_2$H$_4$CON(CH$_3$)C$_4$H$_9^+$, 66%), 114 (C$_4$H$_9$(CH$_3$)CO$^+$, 53%), 88 (100%) and 86 (C$_4$H$_9$(CH$_3$)N$^+$, 35%).

Scheme 11
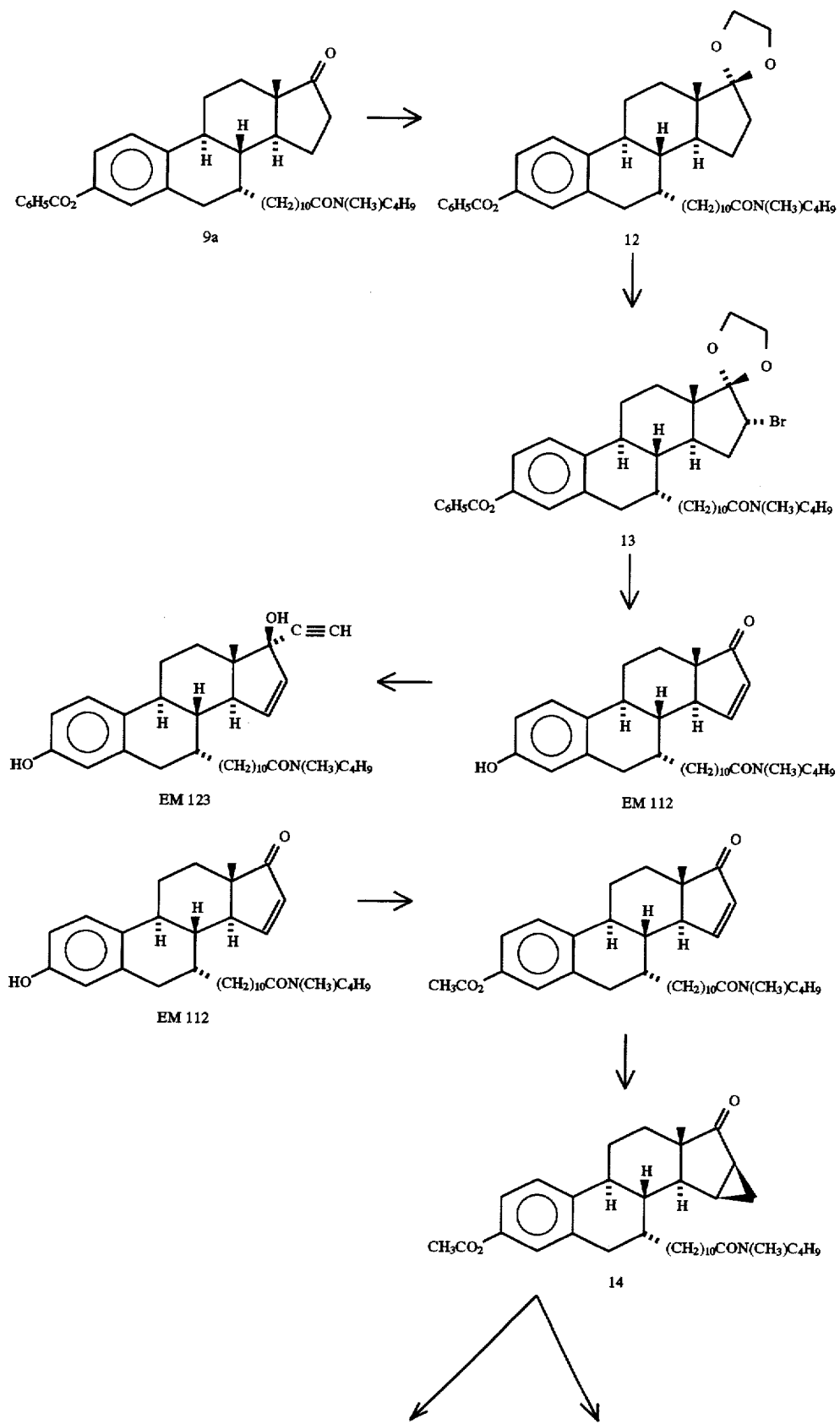

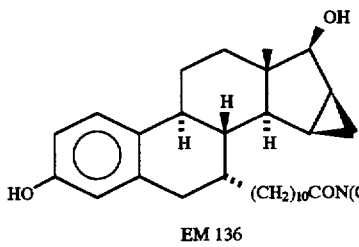
EM 136

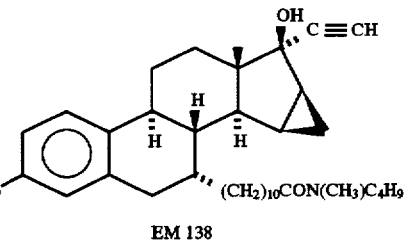
EM 138

EXAMPLE 12

17α-ALKYNYLAMIDE ESTRADIOLS GENERAL PROCEDURE FOR ESTER FORMATION (SCHEMA 12)

In anhydrous conditions under argon atmosphere, bromo acid (17 mmol was dissolved in dry $CH_2Cl_2$ (30 ml), oxalyl chloride (12 ml) was added and the reaction was stirred 2 h at room temperature. Then, dry benzene was added to mixture and solvent was evaporated under reduced pressure (2x) and dried under vaccum. This crude product was dissolved in dry $CH_2Cl_2$ (10 ml and added at 0° C. to a solution of 3-methyl 3-oxetanemethanol (17 mmol), $CH_2Cl_2$, (7 ml and pyridine (1.4 ml). The reaction was kept at this temperature for 4–8 h. Thereafter, mixture was diluted with $CH_2Cl_2$, washed with $NaHCO_3$ (10%, v/w) and organic phase was dried over $MgSO_4$. After removal of solvent, residue was purified by chromatography (hexane-ethyl acetate-triethylamine/80:20:1, v/v/v) to afford bromo ester.

6-bromo hexanoate ester of 3-methyl-3-hydroxymethyloxetane (15).

Light yellow liquid (91% yield); IR v (neat) 2930, 2860, 1725 1450, 1370, 1160 cm⁻; NMR-60 δ ($CDCl_3$) 1.31 (s, 3H), 1.1–2.1 (m, 6H), 2.36 (t, J=6.0 Hz, 2H), 3.36 (t, J=6 Hz, 2H), 4.13 (s, 2H), 4.41 (AB system Δv-=8.3, J=6 Hz, 4H).

9-bromo nonanoate ester of 3-methyl-3-hydroxymethyl oxetane (16).

Colorless liquid (86% yield); IR v (neat) 2920, 2840, 1725, 1450, 1370, 1150 cm⁻¹; NMR-60 δ($CDCl_3$) 1.31 (s, 11H), 1.2–2.2 (m, 4H), 2.40 (t, J=6.0 Hz, 2H), 3.45 (t,J=6.0 Hz, 2H), 4.20 (s, 2H), 4.20 (s, 2H), 4.48 (AB system Δv=8.2, J=6.0 Hz, 4H).

11-bromo undecanoate ester of 3-methyl-3-hydroxymethyl oxetane (17).

Colorless liquid (85% yield); NMR-60 δ($CDCl_3$) 1.33 (s, 15H), 1.0–2.0 (m, 4H), 2.30 (t, J=6.0 Hz, 2H), 3.35 (t, J=6.0 Hz, 2H), 4.12 (s, 2H), 4.40 (AB system Δv–8.2, J=6.0 Hz, 4H).

12-bromo dodecanoate ester of 3-methyl-3-hydroxymethyl oxetane (18).

Colorless liquid (86% yield); IR v (neat) 2910, 2840, 1720, 1450, 1370, 1155 cm⁻¹; NMR-60 δ($CDCl_3$) 1.30 (s, 17H), 1.1–2.0 (m, 4H), 2.30 (t, J=6.0 Hz, 2H), 3.33 (t,J–6.0 Hz, 2H), 4.11 (s, 2H), 4.40 (AB system Δv=8.0, J–6.0 Hz, 4H)

GENERAL PROCEDURE FOR ORTHO ESTER FORMATION (SCHEME 12)

To a solution of bromo ester (3.4–14.2 mmol) in dry $CH_2Cl_2$ (10–40 ml) at 0° C. was added with stirring distilled boron trifluoride etherate (0.85–3.55 mmol). After 4 h at 0° C., reaction mixture was quenched by the addition of triethylamine (3.4–14.2 mol), diluted with diethylether and filtered to remove the amine-$BF_3$ complex. The filtrate was evaporated and residue was purified by chromatography (hexane-ethylacetate-triethylamine/80:20:1, v/v/v) to give bromo ortho ester.

1-(5'-bromo pentanyl)-4-methyl-2,6,7-trioxabicydo [2.2.2] octane (19)

Colorless oil (68% yield); IR v (neat) 2940, 2915, 2855, 1450, 1390, 1050, 980 cm⁻¹; NMR-60 δ ($CDCl_3$) 0.79 (s, 3H), 1.2–2.0 (m, 8H), 3.35 (t, J=6.0 Hz, 2H), 3.87 (s, 6H); MS m/e (rel. intensity) 280 (M⁺, 0.2), 278 (M⁺, 0.2), 250 (8.1), 248 (8.5), 197 (7.2), 195 (7.7), 179 (58), 177 (61), 72 (54), 69 (100).

1-(8'-bromo octanyl)-4-methyl-2,6,7-trioxabicyclo [2.2.2] octane (20)

Amorphous white solid (69% yield); IR v (KBr) 2940, 2900, 2840, 1450, 1390, 1045, 985, 950 cm⁻¹; NMR-60 δ ($CDCl_3$) 0.80 (s, 3H), 1.33 (s, 8H), 1.0–2.1 (m, 6H), 3.40 (t, J=6.0 Hz, 2H), 3.93 (s, 6H); MS m/e (rel. intensity) 323 (M⁺, 2.1), 321 (M⁺2.0), 292 (4.4), 290 (5.1), 239 (8.6), 237 (7.1), 221 (43), 219 (33), 69 (71), 55 (100).

1-(10'-bromo decanyl)-4-methyl-2,6,7-trioxabicyclo [2.2.2] octane (21)

White solid (74% yield); m.p. 51°–53° C.; IR v (KBr) 2940, 2900, 2850, 2830, 1455, 1390, 1055, 985, 955 cm⁻¹; NMR-60 δ ($CDCl_3$) 0.80 (s, 3H), 1.27 (s, 12H) 1.1–2.1 (m, 6H), 3.39 (tJ=6.0 Hz, 2H), 3.87 (s, 6H); MS m/e (rel. intensity) 350 (M⁺, 1.2 , 348 (M⁺, 1.1), 321 (3.0), 319 (7.6), 269 (7.5), 248 (97), 144 (37) 55 (100).

1-(11'bromo undecananyl)-4-methyl-2,6,7, trioxabicydo [2,2,2] octane (22).

White solid (76%, yield); m.p. 47.5°, 48.50° C.; IR v (KBr) 2900, 2835, 1460, 1045, 975 cm⁻¹; NMR-60 δ ($CDCl_3$) 0.79 (s, 3H), 1.25 (s, 14H), 1.1–2.1 (m, 6H), 3.37 (t, J=6.0 Hz, 2H), 3.85 (s, 6H); MS m/e (rel. intensity) 364 CM⁺, 3.5), 362 (M⁺, 3.4), 334 (13), 332 (13), 283 (15), 263 (85), 261 (97), 144 (51), 55 (100).

4. Preparation of 17β-alkynylamide estradiols (scheme 13)

GENERAL PROCEDURE FOR COUPLING REACTION (Scheme 13)

In a flame-dried flask under argon atmosphere, 3,17β-bis tetrahydropyranyl ethynylestradiol 23 (1.5 mmol) synthesized from commercial ethynyl estradiol and dihydropyran was dissolved in dry THF (40 ml) and HMPA (6.0 mmol). The solution was cooled at −78° C. and n-BuLi (3.0 mmol) was added. After 2 h, appropriate bromo ortho ester 19–22 (6.0 mmol in dry THF (10 ml was added at −78° C. The mixture was allowed to return slowly at room temperature and kept at this temperature overnight. Then, brine was added and the reaction mixture was extracted with ethylacetate. The organic phase was dried over $MgSO_4$ and the solvent was removed under reduced pressure. The crude product was purified by chromatography (hexane-ethylacetate-triethylamine/96:4:1 to 50:50:1, v/v/v) to give coupling product 24–27, unreacted steroid 23 (61, 62, 57%) and small quantity of undeterminated product.

1-{3',17'β-bis [(tetrahydro-2"H-pyran-2"yl)oxy} estra-1'3',5'(10')-trien-17'a-yl}-7-(4'-methyl-2',6',7'-trioxabicyclo [2'.2'.2'] octan-1'-yl)-1-heptyne (24).

Colorless oil (15% yield); IR ν (neat) 2920, 2855, 2230, w, 1600, 1485 $cm^{-1}$; NMR-60 δ ($CDCl_3$) 0.75 (s, 3H), 0.88 (s, 3H), 2.80 (n, 2H), 3.2–4.1 (m, 4H), 3.80 (s, 6H), 3.80 (s, 6H), 4.9–5.3 (m, 1H), 5.34 (s, 1H), 6.75 (m, 2H), 7.19 (d, J=8.0 Hz, 1H); MS m/E (rel. intensity) 579 ($M^+$-DHP, 4.0), 564 (1.1), 494 (12), 477 (12), 374 (13), 85 (1000.

1-{3',17β-bis [(tetrahydro-2"H-pyran-2"yl)oxy] estra-1'3',5',(10')-trien-17'α-yl}-10-(4'-methyl-2'.6', 7'-trioxabicyclo [2'.2'.2'] octan-1'-yl)-1-dodecyne (25).

Colorless oil (15% yield); IR ν (neat) 2915, 2850, 2210 w, 1600, 1485 $cm^{-1}$; NMR-200 δ ($CDCl_3$) 0.79 (s, 3H), 0.90 (s, 3H), 2.24 (t, J=6.6 Hz, 2H), 2.83 (m, 2H), 3.55 (m, 2H), 3.89 (s, 6H), 3.95 (m, 2H), 4.98 and 5.19 (2s, 1H), 5.39 (s, 1H), 6.78 (d, J=2.6 Hz, 1H), 6.84 (dd, $J_1$=2.6 Hz and $J_2$=8.4 Hz, 1H), 7.22 (d, J=8.4 Hz, 1H); MS m/e (rel. intensity) 620 ($M^+$-DHP, 4.8), 535 (13), 518 (8.9), 85 (100).

1-{3',17β-bis [(tetrahydro-2"H-pyran-2"yl)oxy] estra-1', 3',5',(10')-trien-17'α-yl}-12-(4'-methyl-2'.6', 7'-trioxabicydo [2'.2'.2'] octan-1'-yl)-1-dodecyne (26).

Colorless visquous oil (42% yield); IR ν (neat) 2920, 2850, 2210 vw, 1600, 1485 $cm^1$; NMR-200 δ ($CDCl_3$) 0.79 (s, 3H), 0.90 (s, 3H), 2.25 (t, J=6.6 Hz, 2H), 2.83 (m, 2H), 3.55 (m, 2H), 3.89 (s, 6H), 3.95 (m, 2H), 5.0 and 5.2 (2s, 1H), 5.39 (s, 1H), 6.78 (d, J=2.6 Hz, 1H), 6.84 (dd, $J_1$=2.6 and $J_2$=8.4 Hz, 1H), 7.21 (d, J=8.4 Hz, 1H); MS m/e (rel. intensity) 649 ($M^+$-DHP, 6.1), 634 (0.7), 564 (22), 547 (16), 85 (100).

1-{3',17'-β-bis[(tetrahydro-2"H-pyran-2"yl)oxy] estra-1'3'5' (10')-trien-1-17'α-yl}-13-(4'methyl-2'.6', 7-trioxabicydo[2'.2'.2']octan-1'-yl)-1-tride cyne (27)

Colorless visquous oil (35% yield); IR ν (neat) 2915, 2850, 2290 vw, 1600, 1490 $cm^{-1}$; NMR-200 δ($CDCl_3$) 0.80 (s, 3H), 0.90 (0.3H), 2.25 (t, J=6.6 Hz, 2H), 2.83 (m, 2H), 3.53 (m, 2H), 3.89 (s, 6H), 3.95 (m, 2H), 5.0 and 5.2 (2s, 1H), 5.39 (s, 1H), 6.78 (d, J=2.2 Hz, 1H), 6.84 (dd, $J_1$=2.6 and $J_2$=8.4 Hz, 1H), 7.21 (d, J=8.4 Hz, 1H).

GENERAL PROCEDURE FOR ORTHO ESTER AND DI-THP HYDROLYSIS

The product with ortho ester and di-THP group (0.22–0.63 mmol was dissolved in MeOH (80–120 ml) and p-toluenesulfonic acid (0.17–0.23 mmol was added. The solution was stirred at room temperature for 2–3 h. Then, water was added, MeOH was removed under reduced pressure and residue was extracted with ethylacetate. After evaporation of solvent, the crude product was purified by column chromatography (hexane-ethylacetate/5;5, v/v) to give ester compound with free hydroxyl group.

8-(3',17'β-dihydroxy estra-1',3',5'(10')-trien-17'α-yl)-7-octynoate ester of 2',2'-dihydroxymethyl propanol (28).

Colorless visquous oil (70% yield); IR ν (film) 3340, 2910, 2850, 1710, 1600, 1485 $cm^{-1}$; NMR-200 δ ($CDCl_3$) 0.83 (s, 3H), 0.86 (s, 3H), 2.27 (t, J=6.4 Hz, 2H), 2.38 (t, J=7.1 Hz, 2H), 2.81 (m, 2H), 3.54 (s broad, 4H), 4.17 (s, 2H), 4.87 (s, 1H, 6.56 (d, J=2.6 Hz, 1H), 6.63 (dd, $J_1$=2.6 Hz and $J_2$=8.4 Hz, 1H), 7.17 (d, J=8.4 Hz, 1H); MS m/e (rel. intensity) 512 ($M^+$, 14), 494 (97), 479 (17), 466 (11), 270 (48), 159 (100).

11-(3',17'β-dihydroxy estra-1',3',5'(10')-trien-17'α-yl)-10-undecynoate ester of 2',2'-dihydroxymethyl propanol (29).

Colorless visquous oil (61% yield); IR ν (neat) 3360, 2910, 2840, 2210 vw, 1710, 1600, 1485 $cm^{-1}$; NMR-200 ($CDCl_3$) a 0.84 (s, 3H), 0.86 (s, 3H), 2.24 (t, J=7.0 Hz, 4H), 2.79 (m, 2H), 3.34 (s broad, 2H), 3.56 (s broad, 4H), 4.13 (s, 2H), 6.57 ($s_{app}$, 1H), 6.63 (dd, $J_1$=2.6 Hz and $J_2$=8.4 Hz, 1H), 7.14 (d, J=8.4 Hz, 1H) MS m/e (rel. intensity) 554 ($M^+$, 5.0), 536 (57), 520 (10), 507 (7.6), 435 (14), 419 (20), 270 (39), 160 (85), 133 (100).

13-(3',17'β-dihydroxy estra-1',3',5'(10')-trien-17'α-yl)-12-tridecynoate ester of 2',2'-dihydroxymethyl propanol (30).

Colorless visquous oil (78% yield); IR ν (film) 3360, 2915, 2840, 1710, 1600, 1490 $cm^{-1}$; NMR-200 δ ($CDCl_3$) 0.83 (s, 6H), 2.25 (m, 4H), 2.78 (m, 2H), 3.53 (s broad, 4H), 4.09 (s, 2H), 6.6 (m, 2H), 7.10 (d, J=8.0 Hz, 1H); MS m/e (rel. intensity) 582 ($M^+$, 1.0), 563 (38), 548 (5.7), 535 (3.5), 463 (5.7), 446 (13), 270 (44), 160 (57), 133 (58), 55 (100).

14-(3',17'β-dihydroxy estra-1',3',5'(10')-trien-17'α-yl)-13-tetradecynoate ester of 2',2'-dihydroxymethyl propanol (31).

Colorless visquous oil (83%, yield); IR ν (film) 3360, 2910, 2840, 2220 vw, 1710, 1605, 1490 $cm^{-1}$NMR-200 δ ($CDCl_3$) 0.85 (s, 3H), 0.87 (s, 3H), 2.25 (t, J=6.6 Hz, 2H), 2.33 (t, J=7.1 Hz, 2H), 2.80 (m, 2H), 2.9 (m, 2H), 3.58 (s broad, 4H), 4.20 (s, 2H), 5.72 (s, 1H), 6.56 (d, J=2.6 Hz, 1H), 6.62 (dd, $J_1$=2.6 Hz and $J_2$=8.4 Hz, 1H), 7.15 (d, J=8.8 Hz, 1H).

GENERAL PROCEDURE FOR HYDROLYSIS OF ESTER FOLLOWING BY AMIDE FORMATION

At a solution of ester (0.14–0.49 mmol) in MeOH (12–50 ml) was added aqueous solution of KOH 10% w/v (6–25 ml) and mixture was refluxed under argon atmosphere for 24 h. Thereafter, water was added and MeOH was evaporated under reduced pressure. The resulting solution was acidified with HCl and extracted with ethylacetate. Organic phase was washed with water, brine and dried over $MgSO_4$. Without purification, the crude carboxylic acid (IR acid band at 1700 and 2400–3600 $cm^{-1}$) was dissolved in dry $CH_2Cl_2$ (20–70 ml) and tributylamine (0.58–2.04 mmol). The mixture was cooled at −10° C., isobutyl chloroformate (0.68–2.41 mmol) was added and allowed to react 30 min. At this time, N-methylbutylamine in excess (4.2–16.0 mmol) was added and the cooling bath was removed. After 2 h, $CH_2Cl_2$ was added and organic phase was washed with HCl (1N) and dried over $MgSO_4$. The solvent was removed and crude amide purified by column chromatography (hexane-ethylacetate/7:3, v/v).

N-butyl, N-methyl-8-[3'-(i-butyloxy carbonyloxy)-17'β-hydroxy estra-1',3',5'(10')-trien-17'α-yl]-7-octynamide (32).

Colorless oil (79% yield); IR v (neat) 3380, 2920, 2850, 1745, 1620 cm$^{-1}$; NMR-200 δ (CDCl$_3$) 0.87 (s, 3H), 0.91 and 0.94 (2t, J=7.3 Hz, 3H), 1.00 (d, J=6.6 Hz, 6H), 2.85 (2H), 6.88 (d, J=2.6 Hz, 1H), 6.93 (dd, J$_1$=2.6 Hz and J$_2$=8.4 Hz, 1H), 7.29 (d, J=8.4 Hz, 1H); MS m/e (rel. intensity) 579 (M$^+$, 12), 561 (26), 546 (11), 461 (6.7), 447 (3.7), 270 (84), 57 (100). EMS M$^+$ calculated for $C_{36}H_{53}O_5N$: 579.3923; found: 579.3970.

N-butyl, N-methyl-11-[3'-(i-butyloxy carbonyloxy)-17'β-hydroxy estra-1',3',5'(10')-trien-17'α-yl]-10-undecynamide (33)

Colorless oil (67% yield); IR v (neat) 3370, 2910, 2840, 1745, 1620 cm$^{-1}$; NMR-200 δ (CDCl$_3$) 0.87 (s, 3H), 0.92 and 0.95 (2t, J=6.6 Hz, 3H), 1.00 (d, J=7.0 Hz, 6H), 2.86 (m, 2H), 2.90 and 2.94 (2s, 3H), 3.24 and 3.35 (2t, J=23 Hz, 2H), 4.03 (d,J=6.6 Hz, 2H), 6.88 (d, J=2.6 Hz, 1H), 6.93 (dd, J$_1$=2.6 Hz and J$_2$=8.8 Hz, 1H), 7.30 (d, J=8.1 Hz, 1H); MS m/e (rel. intensity) 621 (M$^+$, 2.1), 606 (2.4), 602 (6.2), 212 (43), 159 (69), 142 (68), 114 (100).

N-butyl, N-methyl-13-[3'(i-butyloxy carbonyloxy)-17'β-hydroxy estra-1'3',5'(10')-trien-17'α-yl]-12-tridecynamide (34).

Colorless oil (89% yield); IR v (neat) 3370, 2920, 2840, 1745, 1620 cm$^{-1}$; NKR-200 δ (CDCl$_3$) 0.87 (s, 3H), 0.92 and 0.95 (2t, J=7.0 Hz, 3H), 1.00 (d, J=7.0 Hz, 6H), 2.86 (m, 2H), 2.90 and 2.96 (25, 3H), 3.25 and 3.35 (2t, J=7.4 Hz, 2H), 4.02 (d, J=6.6 Hz, 2H), 6.88 (d, J=2.2 Hz, 1H), 6.93 (dd, J$_1$=2.6 Hz and J$_2$=8.4 Hz, 1H), 7.30 (d, J=8.8 Hz, 1H); MS m/e (rel. intensity) 649 (M$^+$, 20), 633 (15), 631 (18), 616 (8.2), 531 (15), 516 (5.6), 270 (85), 57 (100); EMS M$^+$ calculated for $C_{41}H_{63}O_5N$: 649.4706; found 649.4643.

N-butyl, N-methyl-14-[3'(i-butyloxy carbonyloxy)-17'β-hydroxy estra-1',3',5'(10')-trien-17'α-yl]-13-tetradecynamide (35).

Colorless oil (83% yield); IR v (neat) 3380, 2910, 2840, 1750, 1625 cm$^{-1}$; NMR-200 δ (CDCl$_3$) 0.87 (s, 3H), 0.92 and 0.95 (2t, J=7.0 Hz, 3H), 1.00 (d, J=6.6 Hz, 6H), 2.85 (m, 2H), 2.91 and 2.96 (2s, 3H), 3.25 and 3.36 (2t, J=7.4 Hz, 2H), 4.03 (d, J=6.6 Hz, 2H), 6.88 (d, J=2.6 Hz, 1H), 6.93 (dd, J$_1$=2.9 Hz and J$_2$=8.4 Hz, 1H), 7.30 (d, J=8.8 Hz, 1H).

HYDROLYSIS OF CARBONATE

Hydrolysis of carbonate compounds 32–35 was performed as follows: carbonate derivatives were dissolved in methanol (10 ml). $K_2CO_3$ (1%; p/v) in aqueous methanol (25:75, v/v) (10 ml was added and the resulting solution was stirred at room temperature for 3 h. Reaction mixture was acidified with HCl (1N) and MeOH was evaporated under vacuum. The residue was extracted with ethyl acetate and organic phase was dried, evaporated and purified by column chromatography (hexane-ethyl acetate 6.5:3.5, v/v).

N-butyl, N-methyl-8-[3',17'β-dihydroxy estra-1'3',5' (10')-trien-17'α-yl]-7-octynamide ("EM 157").

Purified by column chromatography (hexane-ethyl acetate/4:6, v/v). Amorphous white solid (88% yield); IR v (film) 3280, 2910, 2840, 1610 cm$^{-1}$; NMR-200 δ (CDCl$_3$) 0.87 (s, 3H), 0.91 and 0.94 (2t, J=7.0 Hz, 3H), 2.80 (m, 2H), 2.90 and 2.92 (2s, 3H), 3.22 and 3.34 (2t, J=7.3 Hz, 3H), 5.22 (s, 1H, 6.57 (d, J=2.9 Hz, 1H), 6.64 (dd, J$_1$=2.6 Hz and J$_2$=8.4 Hz, , 7.16 (d, J=8.4 Hz, 1H); MS m/e (rel. intensity) 479 (M$^+$, 11), 462 (18), 460 (38), 446 (18), 270 (30), 114 (56), 88 (67), 44 (100); EMS M$^+$ calculated for $C_{31}H_{45}O_3N$: 479.3399; found 479.3369.

N-butyl, N-methyl-11-[3',17'β-dihydroxy estra-1'3', 5'(10')-trien-17'α-yl)-10-undecynamide ("EM 183").

Purified by column chromatography (hexane-ethylacetate/4:6, v/v). Amorphous white solid (83% yield); IR v (KBr) 3300, 2910, 2840, 1610 cm$^{-1}$; NMR-200δ (CDCl$_3$) 0.87 (s, 3H), 0.93 and 0.95 (2t, J=7.0 Hz, 3H), 2.80 (m, 2H), 2.91 and 2.94 (2s, 3H), 3.23 and 3.35 (2t, J=7.3 Hz, 2H), 5.30 (s, 1H), 6.57 (d, J=2.6 Hz, 1H, 6.64 (dd, J$_1$=2.6 Hz and J$_2$=8.4 Hz, 1H), 7.16 (d, J=8.1 Hz, 1H); MS m/e (rel intensity) 521 (M$^+$, 4.4), 505 (10), 502 (26), 489 (7.7), 487 (8.7), 270 (20), 114 (55), 88 (42), 44 (100).

N-butyl, N-methyl-13-[3',17'β-dihydroxy estra-1'3', 5'(10')-trien-17'α-yl]-12-tridecynamide ("EM 163").

Purified by column chromatography (hexane-ethylacetate/7:3, v/v). Amorphous white solid (98% yield); IR v (film) 3300, 2910, 2840, 1610 cm$^{-1}$; NMR-200 δ (CDCl$_3$) 0.88 (s, 3H), 0.93 and 0.95 (2t, J=7.0 Hz, 3H), 2.80 (m, 2H), 2.93 and 2.97 (2s, 3H), 3.25 and 3.38 (2t, J=7.5 Hz, 2H), 6.61 (d, J=2.6 Hz, 1H), 6.69 (dd, J$_1$=2.6 Hz and J$_2$=8.6 Hz, 1H), 6.87 (s, 1H), 7.14 (d, J=8.1 Hz, 1H); MS m/e (rel. intensity) 549 (M$^+$, 8.7), 532 (17), 530 (23), 516 (12), 270 (30), 114 (35), 88 (45), 44 (100); EMS M$^+$ calculated for $C_{36}H_{55}O_3N$: 549.4182, found: 549.4271.

N-butyl, N-methyl-14-[3',17'β-dihydroxy estra-1'3', 5'(10')-trien-17'α-yl]-13-tetradecynamide ("EM 196").

Purified by column chromatography (hexane-ethyl acetate/6:4, v/v). Amorphous white solid (93% yield); IR v (film) 3280, 2915, 2840, 1615 cm$^{-1}$; NMR-200 δ (CDCl$_3$) 0.88 (s, 3H), 0.94 and 0.95 (2t, J=7.0 Hz, 3H), 2.80 (m, 2H), 2.95 and 2.98 (2s, 3H), 3.26 and 3.39 (2t, J=7.3 Hz, 2H), 6.61 (d, J=2.2 Hz, 1H), 6.70 (dd, J$_1$=2.6 Hz and J$_2$=8.4 Hz, 1H, 7.13 (m, 2H: aromatic and phenolic hydrogen).

Scheme 12

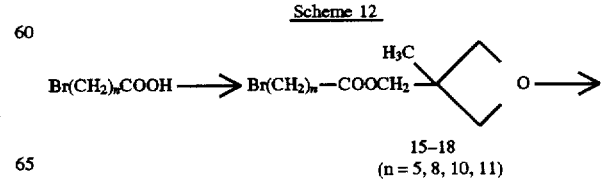

15–18
(n = 5, 8, 10, 11)

Scheme 12
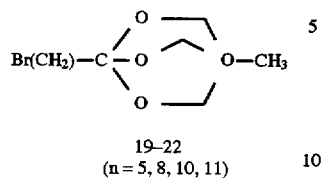
Scheme 13
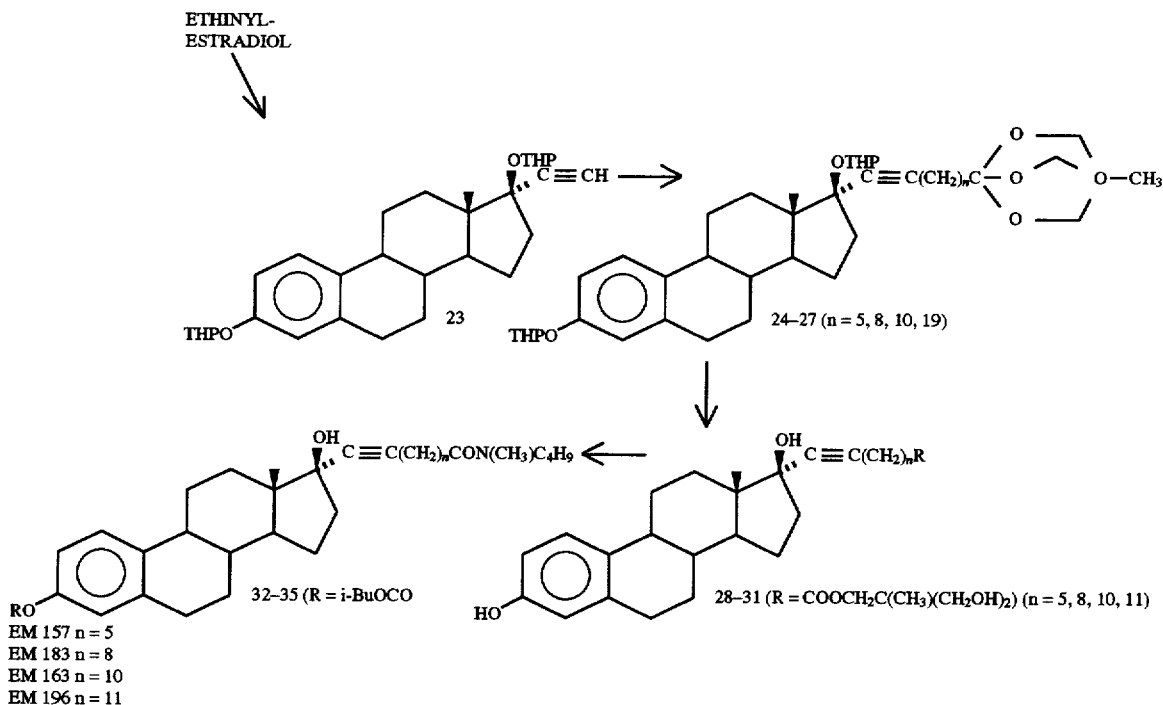
EM 157 n = 5
EM 183 n = 8
EM 163 n = 10
EM 196 n = 11
EXAMPLE 13
Scheme 14
N-n butyl, N-methyl-3(3'-17'β-dihydroxy-11'β-methoxy estra 1',3',5'(10')-trien 7'α-yl) undecanamide ("EM 111") and its 17α-ethynyl derivatives ("EM 121").
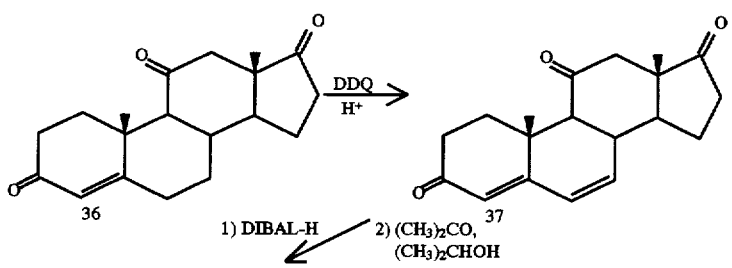

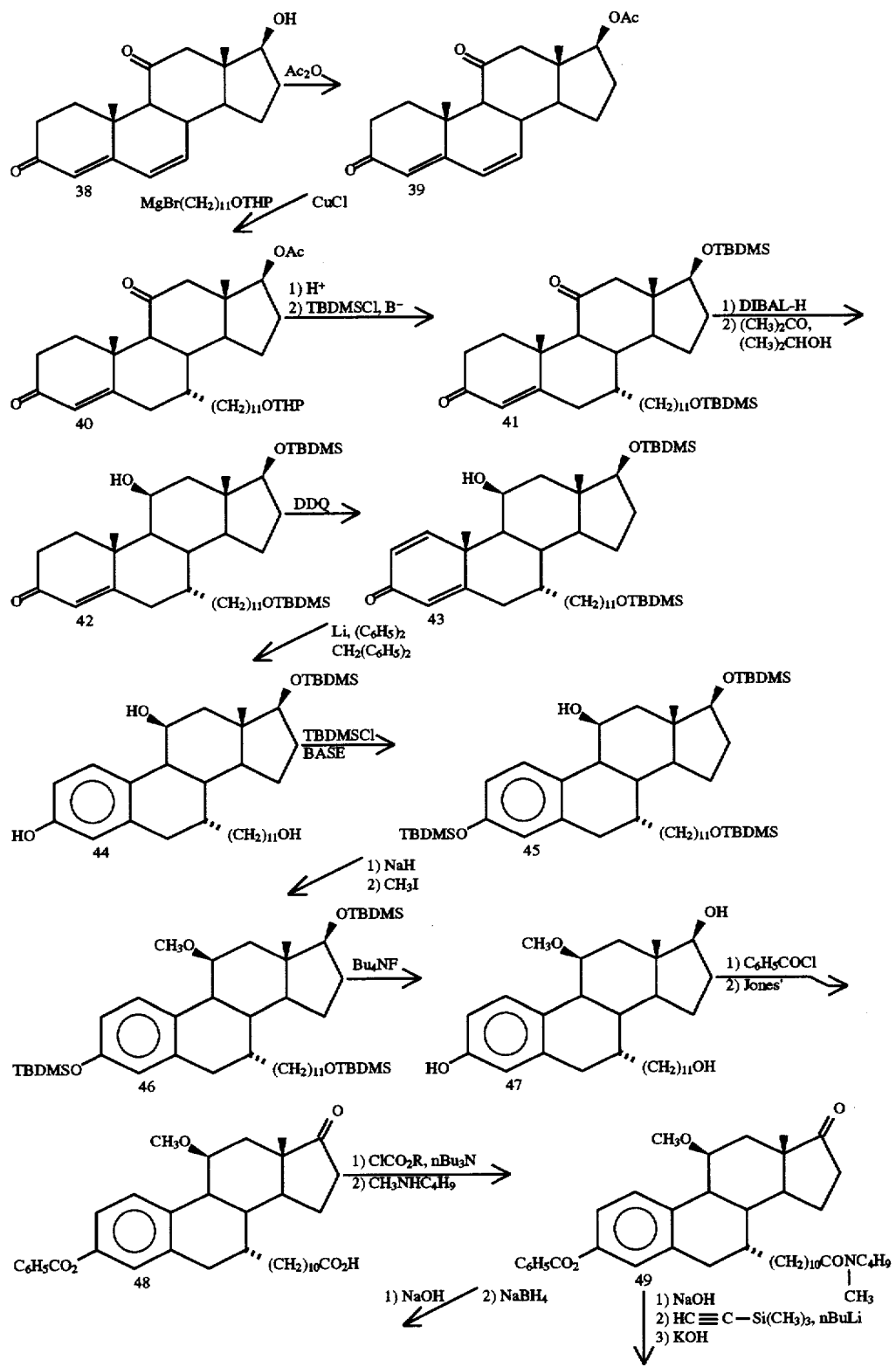

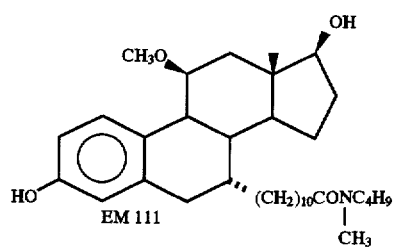
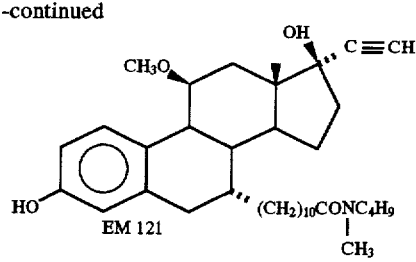
EXAMPLE 14
Scheme 15
11β-chloromethyl derivatives
N-n-butyl, N-methyl, (11β-chloromethyl-3',17'β-dihydroxy-estra-1',3',5'(10')-trien-7'α-yl undecanamide (56) and its 17α-ethynyl derivative (58)
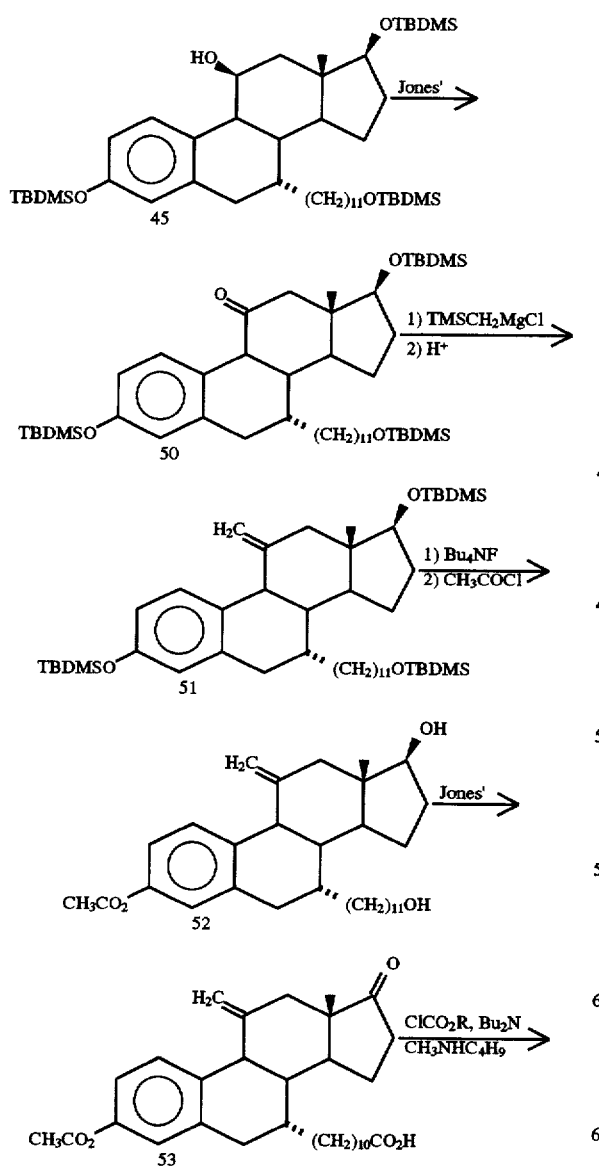
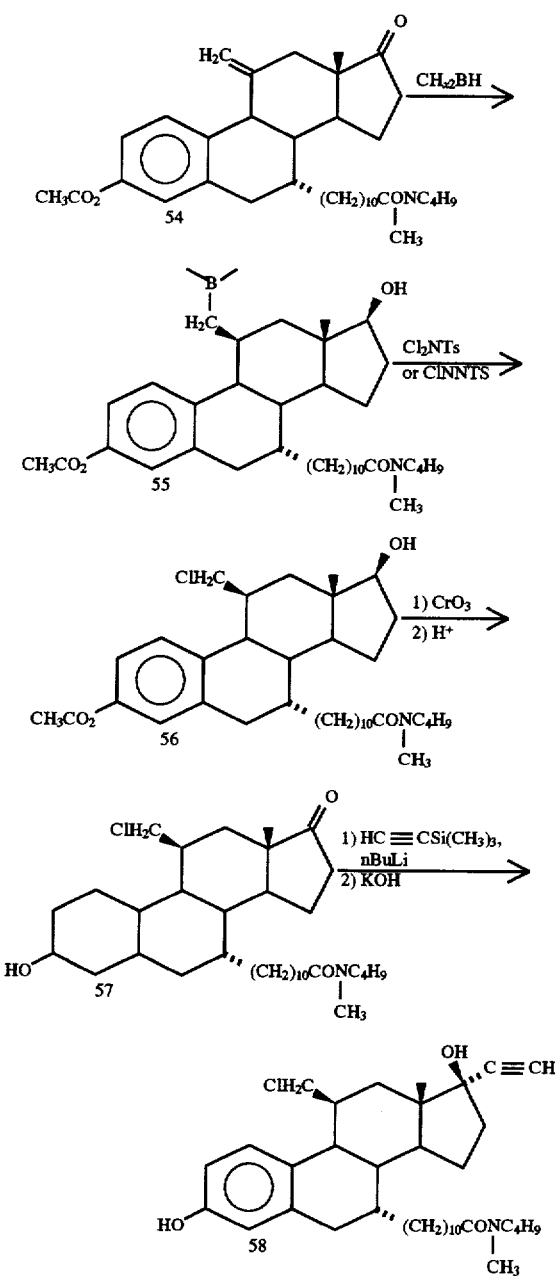

EXAMPLE 15
Scheme 16
Compounds with aliphatic side-chain in 17β-position
N-n-butyl, n-methyl, 11-(17'β-hydroxy-3'-methoxy estra-1',3',5'(10')-trien-17α'α-yl) undecanamide ("EM 103").
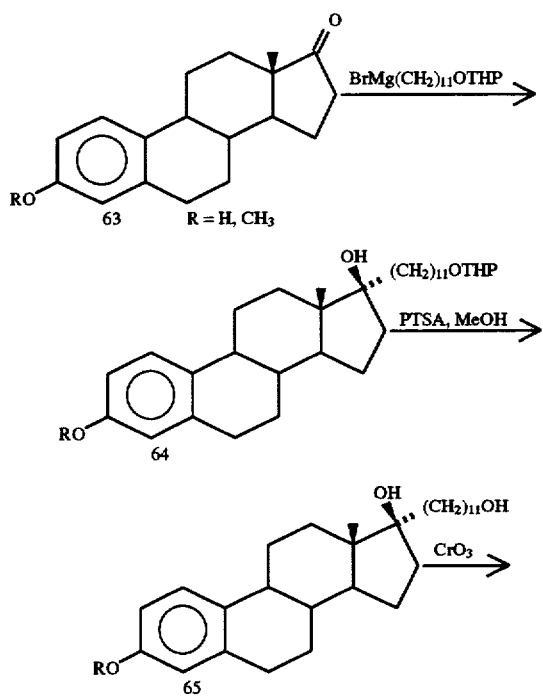
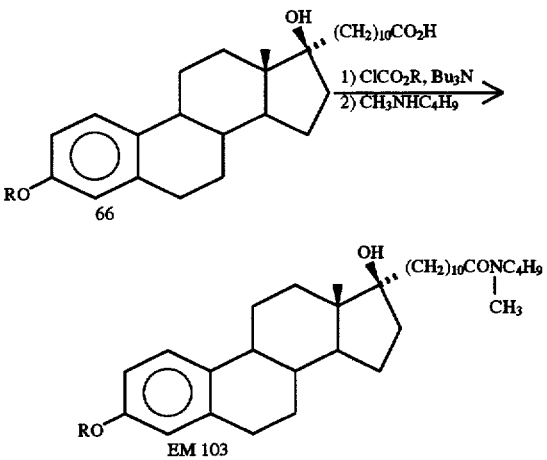
EXAMPLE 16
Scheme 17
17α-cyclopropyl derivatives
N-n-butyl, N-methyl-(17'α-cyclopropyl-3',17β-dihydroxy estra-1',3',5'(10')-trien-7'α-yl) undecanamide (68) and its 17'α-chlorocyclopropyl and 17'α-fluorocyclopropyl derivative (69)
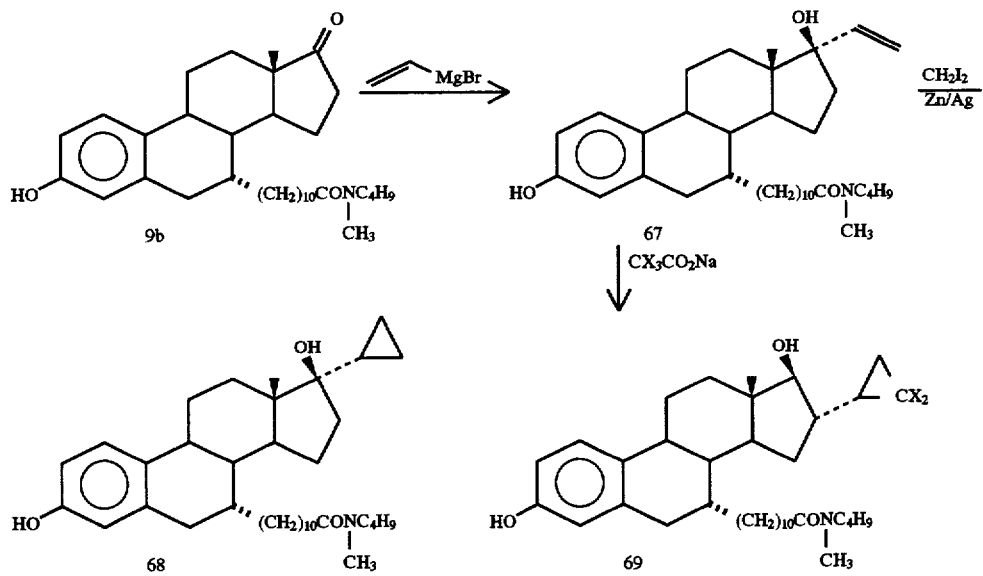
X = F, Cl

73

EXAMPLE 17

N-n-butyl, N-methyl-(17'α-cyclopropyl-3',17β-dihydroxy 11'β-methoxy estra 1',3',5'(10')-trien-7'α-yl undecanamide (70X = H) and its 17'α-chlorocylopropyl and 17α-fluorocyclopropyl derivative (70, X=F, Cl)

Same example as Example 16 with compound 49 as starting material.

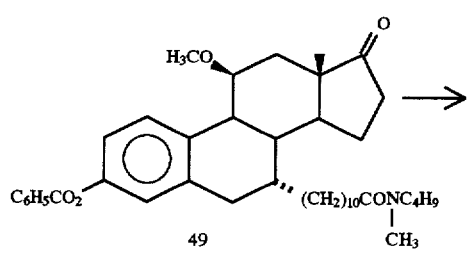

74

-continued

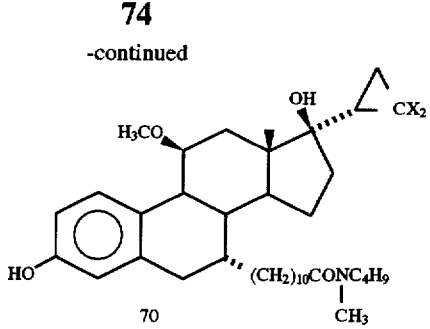

X = H, F, Cl

EXAMPLE 18

Scheme 18

17α-cyanovinyl derivatives

N-n-butyl, N-methyl-11-(17'α-cyclopropyl-3',17β-dihydroxy 11'β-methoxy estra 1',3',5'(10')-trien-7'α-yl) undecanamide (73)

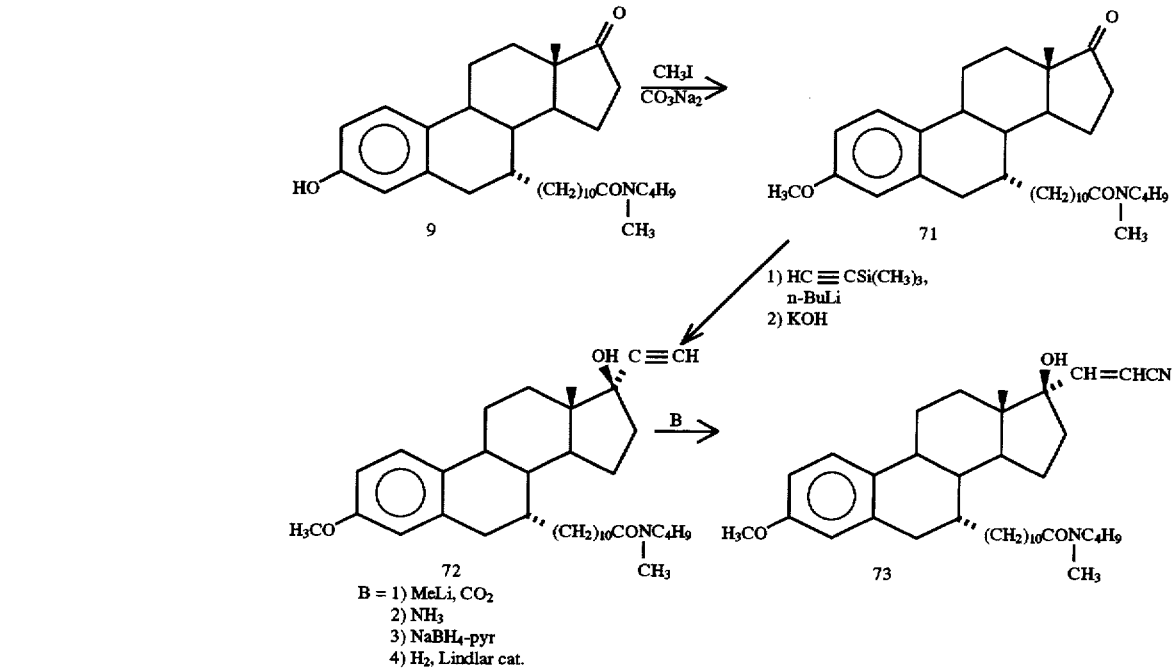

EXAMPLE 19
Scheme 19
Compounds with aliphatic side chain in 15α-position
N-n-butyl, N-methyl-11-(3',17β-dihydroxy 17'α-ethynyl estra 1',3',5',(10)-trien-15'α-yl) undecanamide ("EM 108")
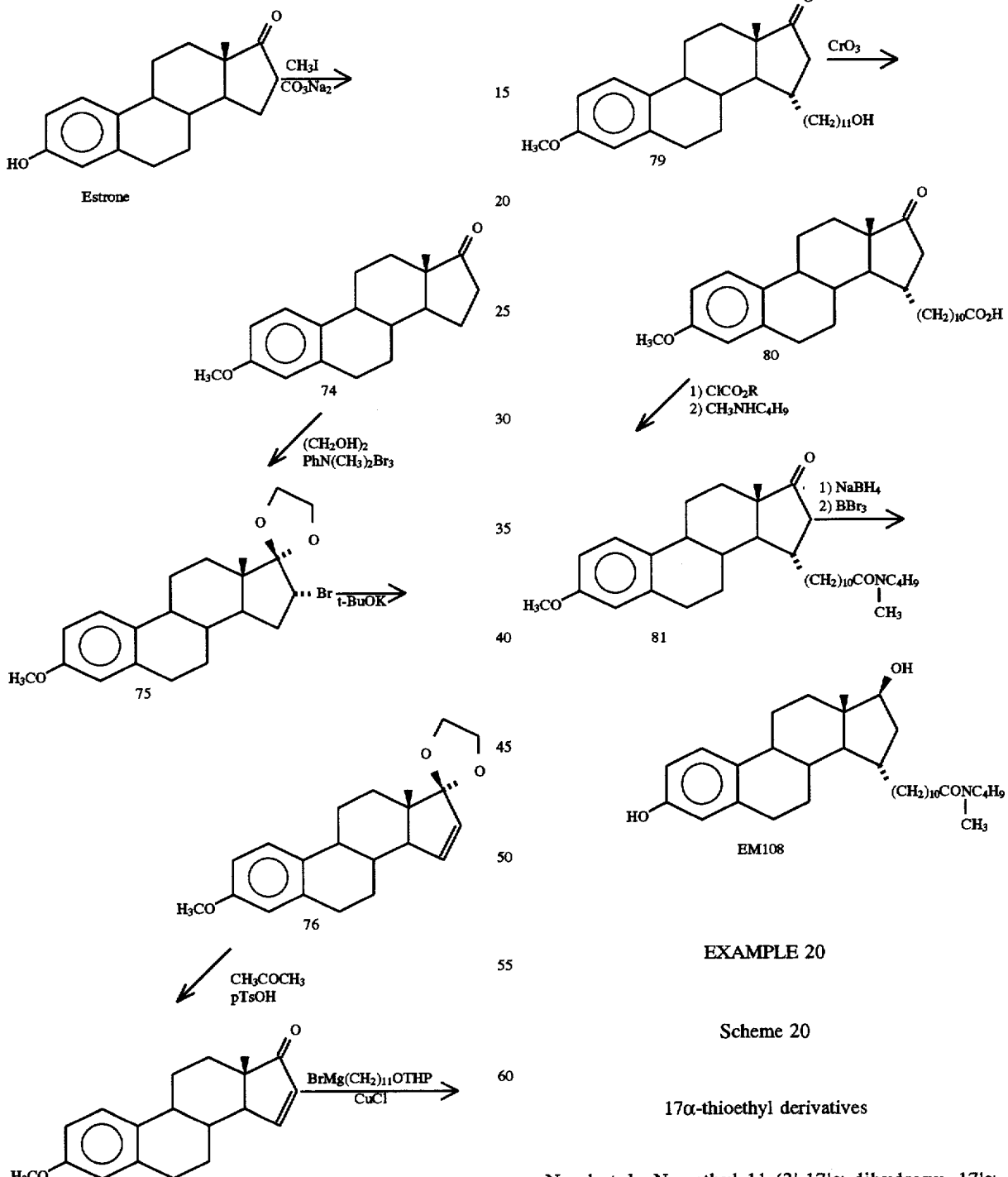
EXAMPLE 20
Scheme 20
17α-thioethyl derivatives
N-n-butyl, N-methyl-11-(3',17'α-dihydroxy 17'α-thioethyl estra 1',3',5',(10)-trien-'α-yl) undecanamide (82) and its ethyl disulfite derivative (83)

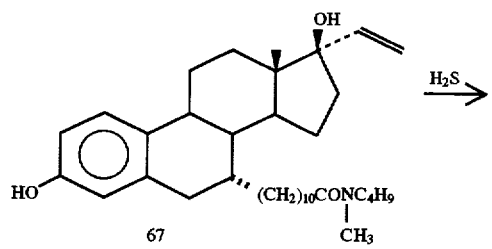
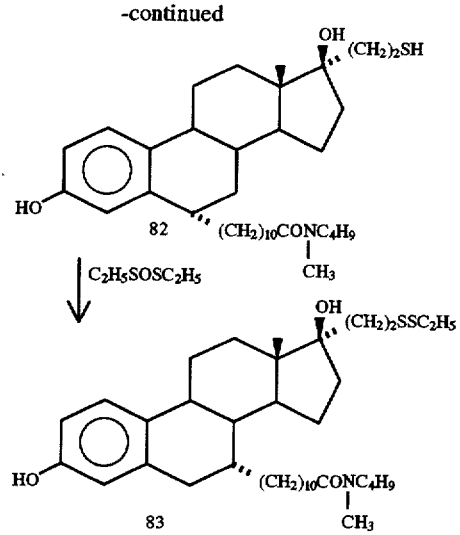
EXAMPLE 21
Scheme 21
17α-thiopropyl derivatives
N-n-butyl, N-methyl-11-(3',17'β-dihydroxy 17'α-thiopropyl estra-1',3',5'(10')-trien-7'-α-yl) undecanamide (84) and its ethyl disulfite derivative (86)
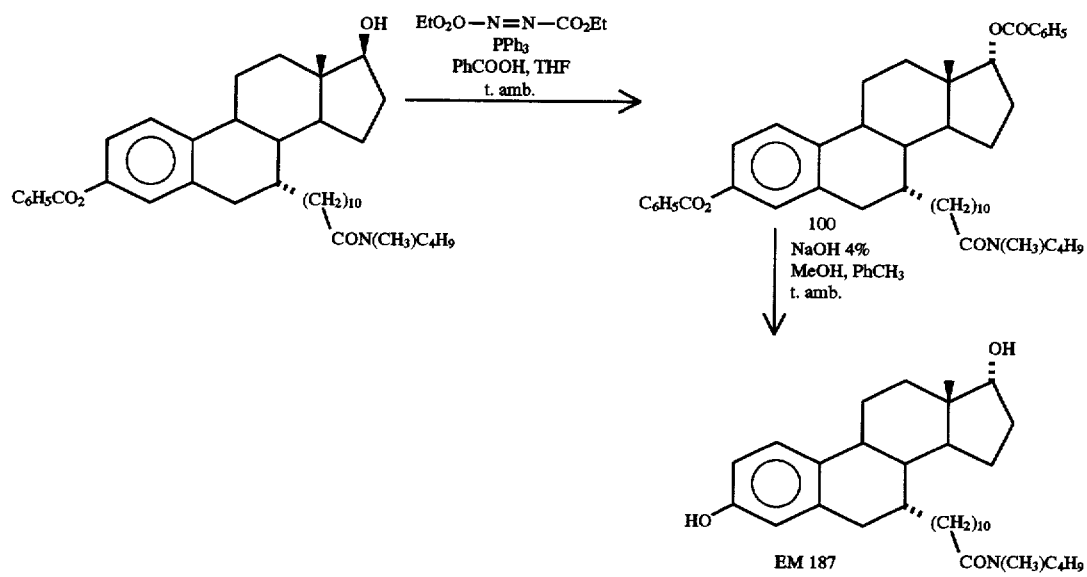

EXAMPLE 22
Scheme 22
11β-ethyl derivatives
N-n-butyl, N-methyl-11-(3',17'β-dihydroxy 17'α-ethynyl-11β-ethyl estra 1',3',5'(10')trien-7'α-yl) undecanamide (97)
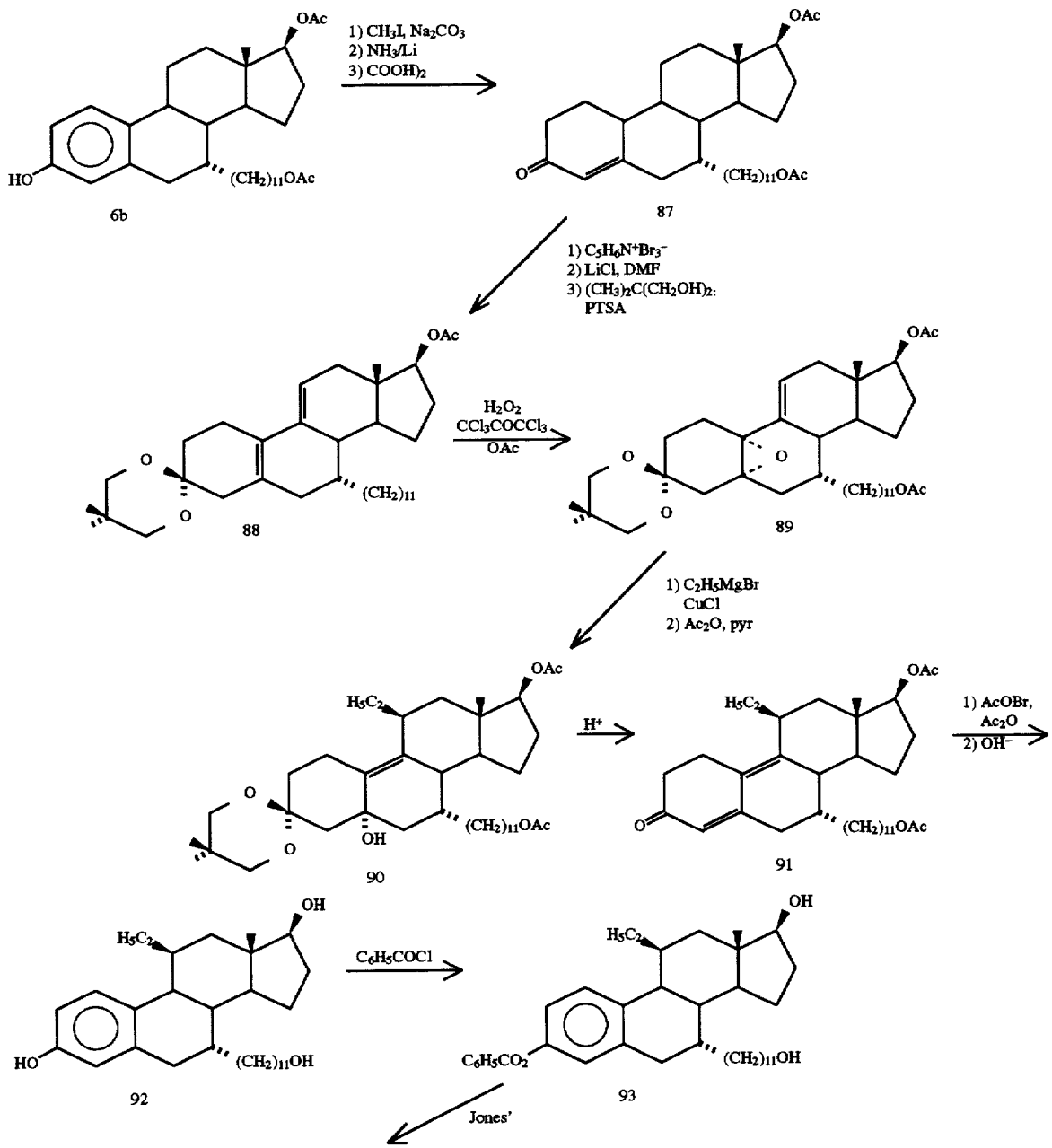

81
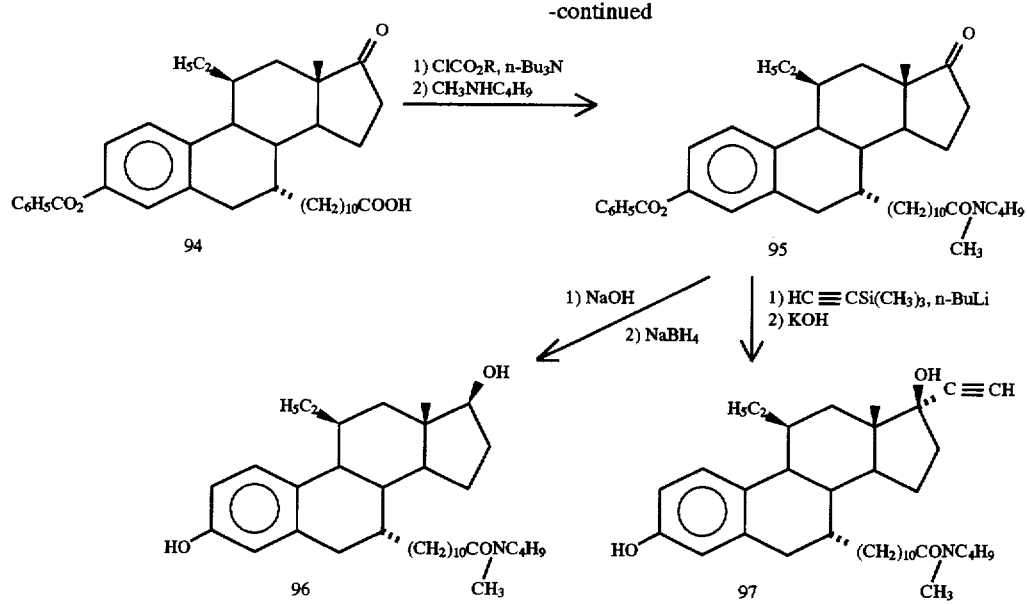
EXAMPLE 23
Scheme 23
14,15 epoxide derivatives
N-n-butyl, N-methyl-11-(3',17'-dibenzoyl-14',15'-epoxy-estra 1',3',5'(10')trien-7'α-yl) undecanamide ("EM 180") and ("EM 181")
82
-continued
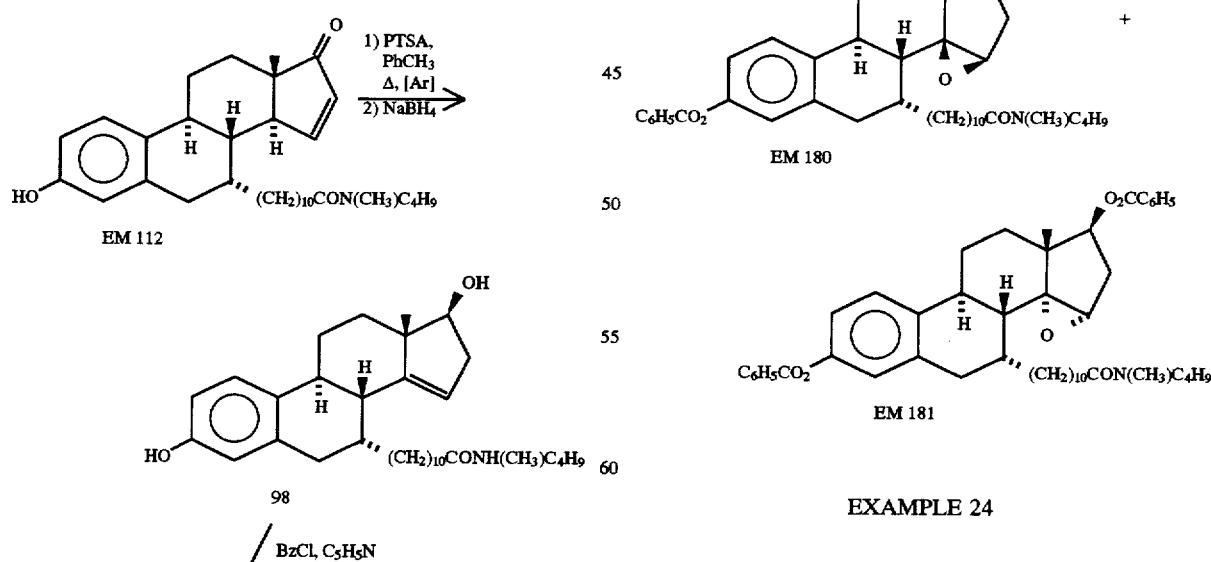
EXAMPLE 24
Scheme 24
N-n-butyl, N-methyl-11-(3',17'α-dihydroxy estra-1',3',5'(10') trien-7'α-yl) undecanamide ("EM 187")

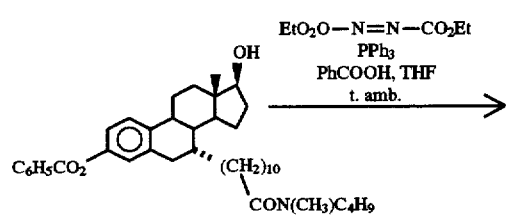
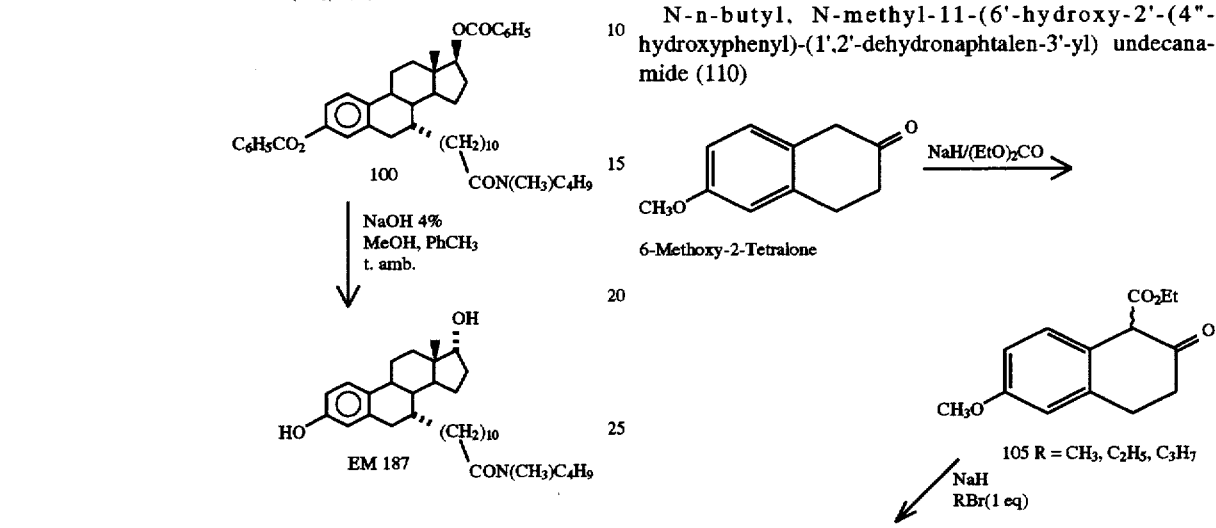
EXAMPLE 25
Scheme 25
N-n-butyl, N-metyl-11-(6'-hydroxy-2'-(4"-hydroxyphenyl)-3'-ethyl-indol-N,-yl) undecanamide (104)
The starting material 101 has been synthesized as described by Von Angered et al., J. Med. Chem. 27: 1439–1447, 1984.
EXAMPLE 26
(Scheme 26)
N-n-butyl, N-methyl-11-(6'-hydroxy-2'-(4"-hydroxyphenyl)-(1',2'-dehydronaphtalen-3'-yl) undecanamide (110)
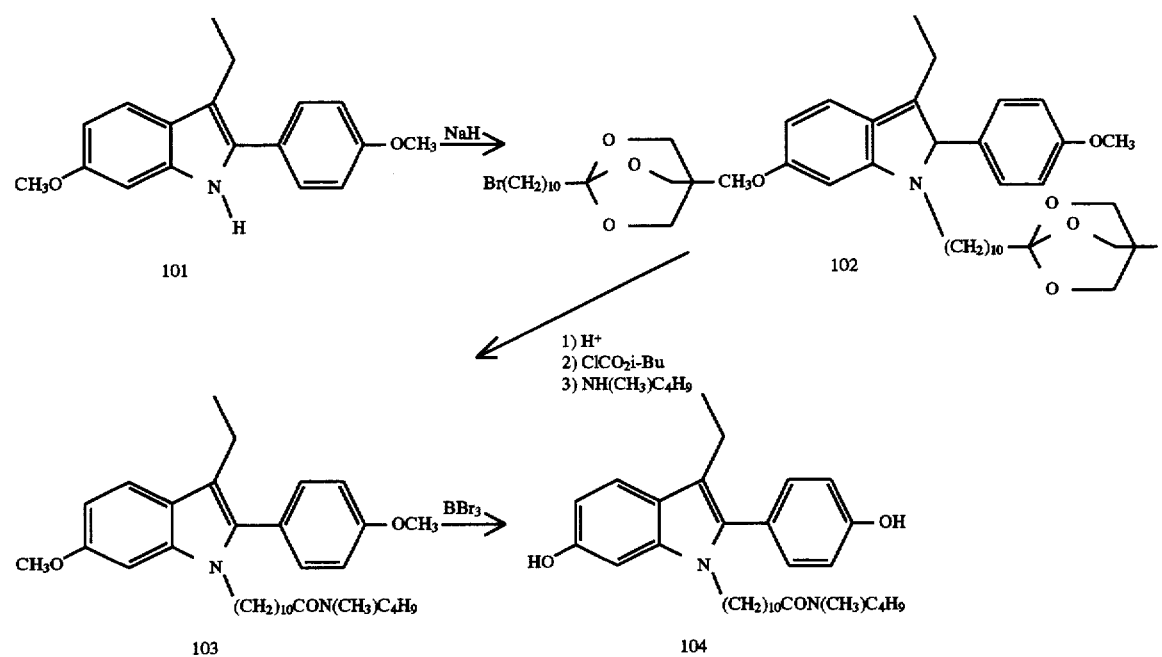

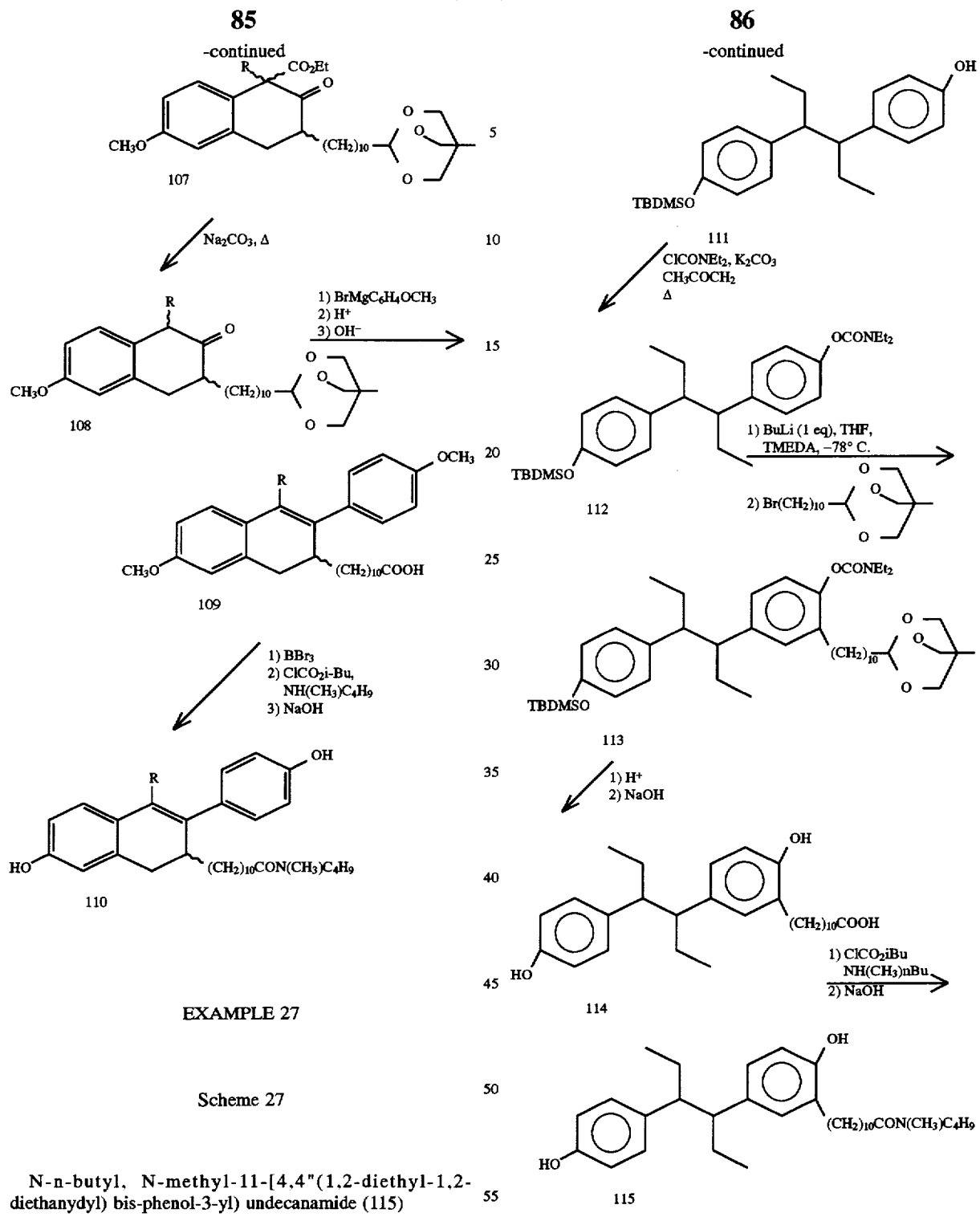

EXAMPLE 27

Scheme 27

N-n-butyl, N-methyl-11-[4,4"(1,2-diethyl-1,2-diethanydyl) bis-phenol-3-yl) undecanamide (115)

Other sex steroid activity inhibitors in accordance with the invention may be synthesized by methods known in the art, by methods analogous to those set forth herein and modifying the syntheses set forth herein in a manner known in the art.

Without intending to be bound by theory, it is believed that diphenyl ethylene and diphenyl ethenylene nuclei discussed herein contribute an enhanced affinity for the estrogen receptor. The ethenylene version with the optional double bond present is preferred, as is a closed third ring which includes, in its sides the ethenyl double bond and one side of one of the phenyl groups. The closed third ring is exemplified by the "B" ring, for example, of formulas XX and XXI below:

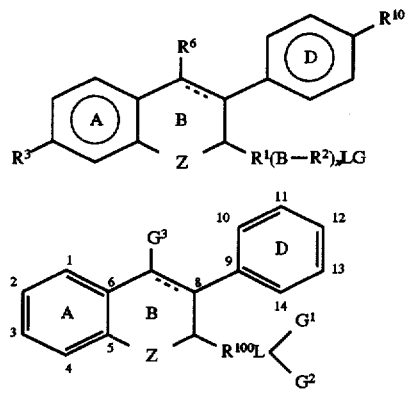

Preferred side chains, which are believed to help provide antagonistic or inhibitory characteristics, include the $R^1[B-R^2-]L-G$ and $A'[Y-A'']_wXR_{21}$ side chains discussed and defined above. Preferred additional substituents to the nucleus are those whose presence facilitates synthesis or enhances stability of the compound, or its metabolic half-life without significantly retarding affinity for the receptor. Smaller substituents such as $C_1-C_2$ alkyl or alkylene groups or halogens may be used.

The $R^6$ substituent of formula XX (the $G^3$ substituent of formula XXI) is preferably either hydrogen or a $C_1-C_3$ hydrocarbon such as methyl, ethyl or propyl. Generally, this substitution location (e.g. the atom receiving $R^6$ of formula XX or $G^3$ of formula XXI) is the atom which is both (A) one atom away from the A-ring and (B) one of the two atoms which receives the optional double bond when it is present. In contrast, the preferred side chain (e.g. $R^1(B—R^2)LG$ of formula XX and $R^{100}LG^1G^2$ of formula XXI) is preferably substituted, as shown in formulas XX and XXI, at the atom which is both (A) one atom away from the optional pi bond and (B) one atom away from Z. It is believed that a lower hydrocarbon substitution at the $R^6$ position of formula XX (the corresponding $G^3$ of formula XXI or the $R^6$ position of formula I) substantially enhances the effectiveness of an inhibitor.

While both the A and D rings may be unsubstituted, certain embodiments include hydroxy substitution on one or both of the A and D rings (especially at the 3 and/or 12 positions of formula XXI or the 3 and/or 10 positions of formula XX). Other preferred substituents to the A and D rings include a substituent which would be converted to hydroxy in vivo after the pharmaceutical is administered to a patient. Such substituents include, for example, methoxy, ethoxy or esters.

Set forth below are several preferred compounds for use in the pharmaceutical composition of the invention corresponding to the structure:

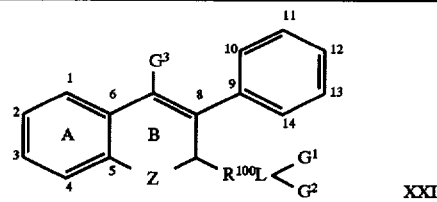

| EM | Z | $R^{100}$ | L | $G_1$ | $G_2$ | $G_3$ | A or D ring hydroxylated (at 3 or 12) |
|---|---|---|---|---|---|---|---|
| EM 738 | $CH_2$ | $(CH_2)_5$ | | $CONC_4H_8$ | | $CH_3$ | A + D |
| EM 681 | $CH_2$ | $(CH_2)_6$ | | $CONC_5H_{10}$ | | $CH_3$ | A + D |
| EM 736 | $CH_2$ | $(CH_2)_7$ | —CON< | $CH_3$ | $C_4H_9$ | $CH_3$ | A + D |
| EM 698 | $CH_2$ | $(CH_2)_8$ | —CON< | $CH_3$ | $C_4H_9$ | $CH_3$ | A + D |
| EM 819 | $CH_2$ | $(CH_2)_9$ | —CON< | $CH_3$ | $C_4H_2F_7$ | $C_2H_5$ | A + D |
| EM 690 | $CH_2$ | $(CH_2)_{10}$ | —CON< | $CH_3$ | $C_4H_9$ | $CH_3$ | A + D |
| EM 661 | $CH_2$ | $(CH_2)_5$ | —SO— | $C_4H_2F_7$ | — | $C_2H_5$ | A + D |
| EM 663 | $CH_2$ | $(CH_2)_6$ | —SO— | $C_4H_9$ | — | $CH_3$ | A + D |
| EM 654 | $CH_2$ | $(CH_2)_7$ | —SO— | $C_5H_{11}$ | — | $CH_3$ | A + D |
| EM 732 | $CH_2$ | $(CH_2)_9$ | —SO— | $C_5H_6F_5$ | — | $CH_3$ | A + D |
| EM 656 | $CH_2$ | $(CH_2)_{10}$ | —SO— | $C_4H_9$ | — | $C_2H_5$ | A + D |
| EM 360 | $CH_2$ | $CH_2C_6H_4O(CH_2)_2$ | —N< | $CH_3$ | $CH_3$ | $CH_3$ | D only |
| EM 431 | $CH_2$ | $CH_2C_6H_4O(CH_2)_2$ | | $NC_5H_{10}$ | | $CH_3$ | D only |
| EM 363 | $CH_2$ | $CH_2C_6H_4O(CH_2)_2$ | | $NC_4H_8$ | | $C_2H_5$ | D only |
| EM 471 | $CH_2$ | $(CH_2)_5$ | —N< | $CH_3$ | $CH_3$ | $CH_3$ | A + D |
| EM 473 | $CH_2$ | $(CH_2)_6$ | | $NC_5H_{10}$ | | $CH_3$ | A + D |
| EM 465 | $CH_2$ | $(CH_2)_7$ | | $NC_4H_8$ | | $C_2H_5$ | A + D |
| EM 777 | $CH_2$ | $C_6H_4O(CH_2)_2$ | —N< | $CH_3$ | $CH_3$ | $CH_3$ | D only |
| EM 773 | $CH_2$ | $C_6H_4O(CH_2)_2$ | —N< | $C_2H_5$ | $C_2H_5$ | $C_2H_5$ | D only |
| EM 765 | $CH_2$ | $C_6H_4O(CH_2)_2$ | | $NC_5H_{10}$ | | $CH_3$ | D only |
| EM 778 | $CH_2$ | $C_6H_4O(CH_2)_2$ | | $NC_4H_8$ | | $C_2H_5$ | D only |
| EM 734 | $CH_2$ | $C_6H_4O(CH_2)_2$ | —N< | $CH_3$ | $CH_3$ | $CH_3$ | D only |
| EM 699 | $CH_2$ | $C_6H_4O(CH_2)_2$ | —N< | $C_2H_5$ | $C_2H_5$ | $CH_3$ | D only |
| EM 735 | $CH_2$ | $C_6H_4O(CH_2)_2$ | | $NC_5H_{10}$ | | $CH_3$ | D only |
| EM 725 | $CH_2$ | $C_6H_4O(CH_2)_2$ | | $NC_4H_8$ | | $CH_3$ | D only |
| EM 779 | $CH_2$ | $C_6H_4O(CH_2)_2$ | —N< | $C_4H_2F_7$ | $CH_3$ | H | D only |
| EM 542 | O | $C_6H_4O(CH_2)_2$ | —N< | $CH_3$ | $CH_3$ | $CH_3$ | A + D |
| EM 543 | O | $C_6H_4O(CH_2)_2$ | | $NC_4H_8$ | | $CH_3$ | A + D |
| EM 562 | O | $C_6H_4O(CH_2)_2$ | | $NC_5H_{10}$ | | $CH_3$ | A + D |
| EM 756 | O | $C_6H_4O(CH_2)_2$ | | $NC_5H_{10}$ | | $C_2H_5$ | A + D |

-continued

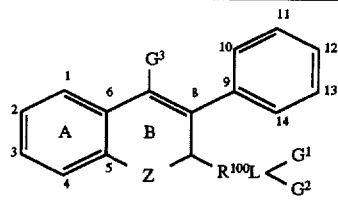

XXI

| EM | Z | $R^{100}$ | L | $G_1$ | $G_2$ | $G_3$ | A or D ring hydroxylated (at 3 or 12) |
|---|---|---|---|---|---|---|---|
| EM 623 | O | $C_6H_4O(CH_2)_3$ | —N< | $C_2H_5$ | $C_2H_5$ | $CH_3$ | A + D |
| EM 321 | O | $C_6H_4O(CH_2)_3$ | | $NC_4H_8$ | | $CH_3$ | A + D |
| EM 872 | O | $C_6H_4O(CH_2)_3$ | | $NC_5H_{10}$ | | $C_2H_5$ | A + D |
| EM 691 | O | $C_6H_4O(CH_2)_3$ | —N< | $CH_3$ | $CH_3$ | $CH_3$ | A + D |
| EM 423 | O | $C_6H_4O(CH_2)_2$ | | $NC_5H_{10}$ | | $C_2H_5$ | D only |
| EM 428 | O | $C_6H_4O(CH_2)_2$ | | $NC_4H_8$ | | $CH_3$ | D only |
| EM 432 | O | $C_6H_4O(CH_2)_2$ | —N< | $CH_3$ | $CH_3$ | $CH_3$ | D only |
| EM 472 | O | $C_6H_4O(CH_2)_3$ | | $NC_5H_{10}$ | | $CH_3$ | D only |
| EM 492 | O | $C_6H_4O(CH_2)_3$ | | $NC_4H_8$ | | $C_2H_5$ | D only |
| EM 384 | O | $C_6H_4O(CH_2)_3$ | | $NC_5H_{10}$ | | H | Neither |
| EM 386 | O | $C_6H_4O(CH_2)_2$ | —N< | $CH_3$ | $CH_3$ | $CH_3$ | Neither |
| EM 382 | O | $C_6H_4O(CH_2)_3$ | —N< | $CH_3$ | $CH_3$ | $C_2H_5$ | Neither |
| EM 345 | O | $(CH_2)_7$ | —CON< | $CH_3$ | $C_4H_9$ | H | A + D |
| EM 453 | O | $(CH_2)_8$ | —CON< | $CH_3$ | $C_4H_2F_7$ | $CH_3$ | A + D |
| EM 358 | O | $(CH_2)_9$ | —CON< | $CH_3$ | $C_4H_9$ | H | A + D |
| EM 467 | O | $(CH_2)_{10}$ | —CON< | $CH_3$ | $C_4H_9$ | $C_2H_5$ | A + D |
| EM 532 | O | $(CH_2)_{10}$ | | $CONC_4H_8$ | | $C_2H_5$ | A + D |
| EM 631 | O | $(CH_2)_5$ | | $NC_4H_8$ | | $CH_3$ | A + D |
| EM 721 | O | $(CH_2)_6$ | | $NC_5H_{10}$ | | $CH_3$ | A + D |
| EM 612 | O | $(CH_2)_7$ | —N< | $C_2H_5$ | $C_2H_5$ | $C_2H_5$ | A + D |
| EM 511 | O | $(CH_2)_9$ | —SO— | $C_5H_6F_5$ | — | H | A + D |
| EM 513 | O | $(CH_2)_{10}$ | —SO— | $C_4H_{10}$ | — | $CH_3$ | A + D |
| EM 512 | O | $C_3H_2$ | | $NC_4H_8$ | | H | A + D |
| EM 555 | O | $C_3H_2$ | | $NC_5H_{10}$ | | $CH_3$ | A + D |
| EM 560 | S | $C_6H_4O(CH_2)_2$ | | $NC_5H_{10}$ | | H | D only |
| EM 635 | S | $C_6H_4O(CH_2)_2$ | | $NC_4H_8$ | | $CH_3$ | D only |
| EM 547 | S | $C_6H_4O(CH_2)_2$ | —N< | $C_2H_5$ | $C_2H_5$ | H | D only |
| EM 541 | S | $(CH_2)_5$ | —CON< | $CH_3$ | $C_4H_9$ | H | A + D |
| EM 634 | S | $(CH_2)_7$ | —CON< | $CH_3$ | $C_4H_9$ | $CH_3$ | A + D |
| EM 563 | S | $(CH_2)_8$ | —CON< | $CH_3$ | $C_4H_9$ | H | A + D |
| EM 762 | S | $(CH_2)_9$ | —CON< | $CH_3$ | $C_4H_9$ | H | A + D |
| EM 941 | S | $(CH_2)_{10}$ | | $CONC_4H_8$ | | $CH_3$ | A + D |
| EM 821 | $NCH_3$ | $C_6H_4O(CH_2)_2$ | | $NC_5H_{10}$ | | H | A + D |
| EM 753 | $NCH_3$ | $C_6H_4O(CH_2)_2$ | —N< | $C_2H_5$ | $C_2H_5$ | $CH_3$ | A + D |
| EM 637 | $NCH_3$ | $C_6H_4O(CH_2)_3$ | | $NC_4H_8$ | | $CH_3$ | A + D |
| EM 343 | O | $C_6H_4O(CH_2)_2$ | | $NC_5H_{10}$ | | $CH_3$ | A + D |

Non-limiting examples of synthesis of representative inhibitors are set forth below.

EXAMPLE 28 scheme 28

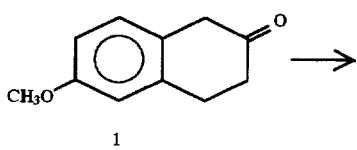

1

-continued
scheme 28

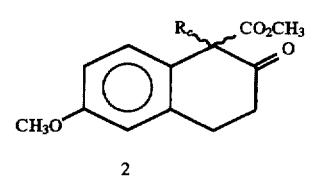

2

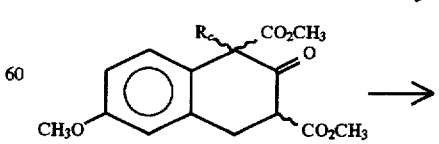

3

-continued
scheme 28

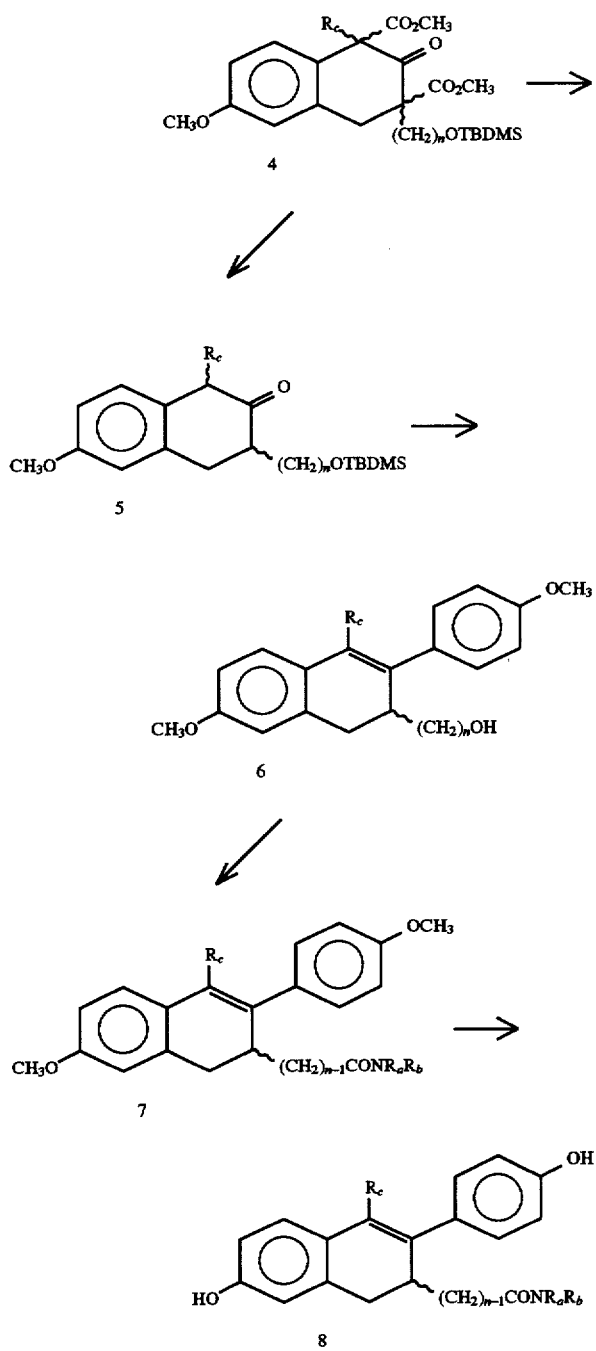

β-methoxytetralone 1 (0.254 g, 1.4 mmol in 5 ml of THF) was added to a refluxed mixture of (MeO)$_2$CO (2.8 mmol) and sodium hydride (38 mg) in THF (20 ml). The mixture was heated at reflux during the night, cooled, water (25 ml) was added and neutralized with 5% HCL and extracted with ether. The ether was washed with a cooled satured sodium bicarbonate and water. The organic phase was dried with anhydrous MgSO$_4$ and the solvent was removed under reduced pressure. The residue in THF (5 ml) was added to a mixture of sodium hydride (21 mg 0.85 mmol and R$_c$I (CH$_3$I, 8.5 mmol) in THF (15 ml) and HMPA (1.7 mmol). The mixture was stirred during the night, water (25 ml) was added and neutralized with 5% HCL and extracted with ether. The ether was washed with a cooled satured sodium bicarbonate and water. The organic phase was dried with anhydrous MgSO$_4$ and the solvent was removed under reduced pressure and the compound 2 (R$_c$=CH$_3$) was obtained in the yield of 80%. The action of MeOCOCN (0.1 ml, 10 min at −78° C.) on the compound 2 (R$_c$=CH$_3$) (200 mg in 5 ml THF) in presence of LDA (lithium diisopropyl amine prepared from 0.13 ml diisopropyl amine and 1.6M butyl lithium ( 0.6 ml at −25° C., 30 min ) and HMPA (0.15 ml) yield in 83% the compound 3 (R$_c$=CH$_3$). To this compound (290 mg) in THF (20 ml) was added 35% potassium hydride (119 mg, 0.72 mmol) 18-crown-6 (24 mg 0.06 mmol and the mixture stirred 8 h at 25° C. and then I(CH$_2$)$_8$OTBDMS (657 mg, 1.9 mmol) was added and the mixture heated at reflux 6 h. The extraction with ethyl acetate yield the compound 4 (n=8, R$_c$=CH$_3$)(98%). The decarboalkoxylation with lithium bromide in pyridine yield the compound 5 (n=8, R$_c$=CH$_3$ ) which was treated by the Grignard's reagent of 3-bromo-anisole followed by acidic treatment. The resulting compound 6 (n=8, R$_c$=CH$_3$) was converted into amide 7 (n=8, R$_a$=CH$_3$, R$_b$=C$_4$H$_9$, R$_c$=CH$_3$) Thus a cooled solution compound 6 (n=8, R$_c$=CH$_3$) (700 mg) in acetone (17 ml) was added Jones' reagent (8N-chromic acid solution, 0.77 ml). After 30 minutes, isopropanol (5 ml) was added and the mixture was poured in water and extracted three times with ethyl acetate. The organic layer was washed twice with brine, dried over magnesium sulfate and evaporated to dryness. The crude acid was used in the next step without purification. To its solution in anhydrous methylene chloride (4 ml) at −10° C. was added, under stirring, triisobutylamine (470 μl, 1.96 mmol and isobutylchloroformate (280 μl, 2.1 mmol). After 40 minutes, N-methylbutylamine (1.5 ml) was added and the mixture was stirred at room temperature during 1 hour. Methylene chloride (50 ml) was added. The organic solution was washed with 1N HCl, saturated sodium bicarbonate solution and water (3X), dried on magnesium sulfate and evaporated to dryness. The residue was purified by "Flash chromatography" on silica gel (Kieselgel 60, Merck, under 0.063 mm, 50 g). Elution with a mixture of hexane-ethyl acetate gave the amide 7 (n=8, R$_a$=CH$_3$, R$_b$=C$_4$H$_9$, R$_c$=CH$_3$) (63%) The removal of the protection into compound 8 (EM 736, n=7, R$_a$=CH$_3$, R$_b$=C$_4$H$_9$, R$_c$=CH$_3$) is performed with pyridine-HCl.

TABLE 1

| EM | n | R$_a$ | R$_b$ | R$_c$ |
|---|---|---|---|---|
| EM 738 | 5 | | —C$_4$H$_8$— | CH$_3$ |
| EM 681 | 6 | | —C$_5$H$_{10}$— | CH$_3$ |
| EM 736 | 7 | CH$_3$ | C$_4$H$_9$ | CH$_3$ |
| EM 698 | 8 | CH$_3$ | C$_4$H$_9$ | CH$_3$ |
| EM 819 | 9 | CH$_3$ | C$_4$H$_2$F$_7$ | C$_2$H$_5$ |
| EM 690 | 10 | CH$_3$ | C$_4$H$_9$ | CH$_3$ |

EXAMPLE 29

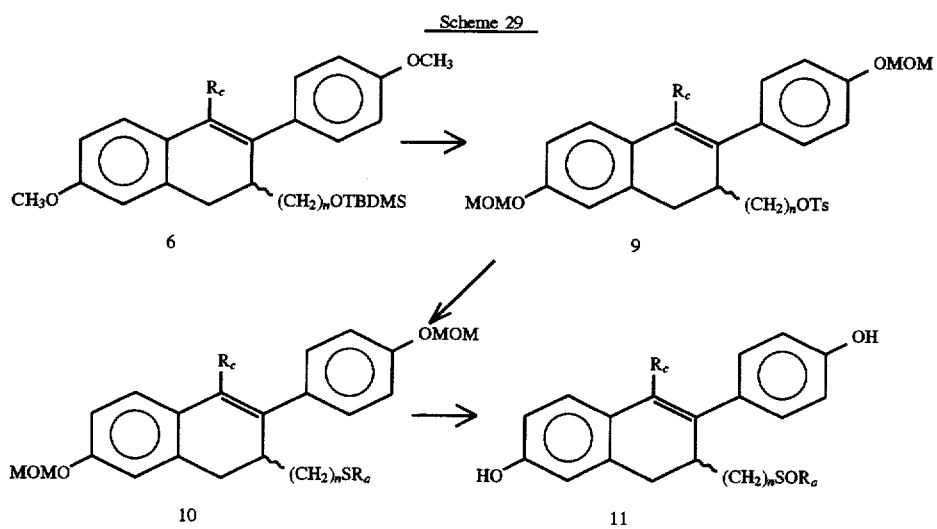

TBDMS: t-butyl dimethylsilyl
MOM: Methyloxymethyl

The compound 6 (n=9, $R_c$=$CH_3$) is deprotected with pyridine-HCl and the phenol function is selectively protected as MOM derivative by treatment with $CH_3OCH_2Cl$ in pyridine. The esterification of the alcohol with PTSCl in pyridine gives the compound 9 (n=9, $R_c$=$CH_3$) which is transformed in sulfide 10 (n=9,$R_a$=$C_5H_6F_5$, $R_c$=$CH_3$) with sodium hydride and $R_a$ SH. The oxidation with mCPBA and the acidic hydrolysis gives the sulfoxide 11 (EM 732, n=9, $R_a$=$C_5H_6F_5$, $R_c$=$CH_3$).

TABLE 2

| EM | n | $R_a$ | $R_c$ |
|---|---|---|---|
| EM 661 | 5 | $C_4H_2F_7$ | $C_2H_5$ |

TABLE 2-continued

| EM | n | $R_a$ | $R_c$ |
|---|---|---|---|
| EM 663 | 6 | $C_4H_9$ | $CH_3$ |
| EM 654 | 7 | $C_5H_{11}$ | $CH_3$ |
| EM 732 | 9 | $C_5H_6F_5$ | $CH_3$ |
| EM 656 | 10 | $C_4H_9$ | $C_2H_5$ |

EXAMPLE 30

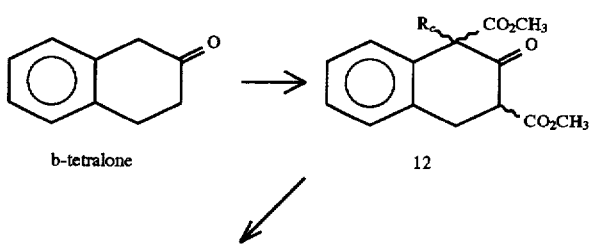

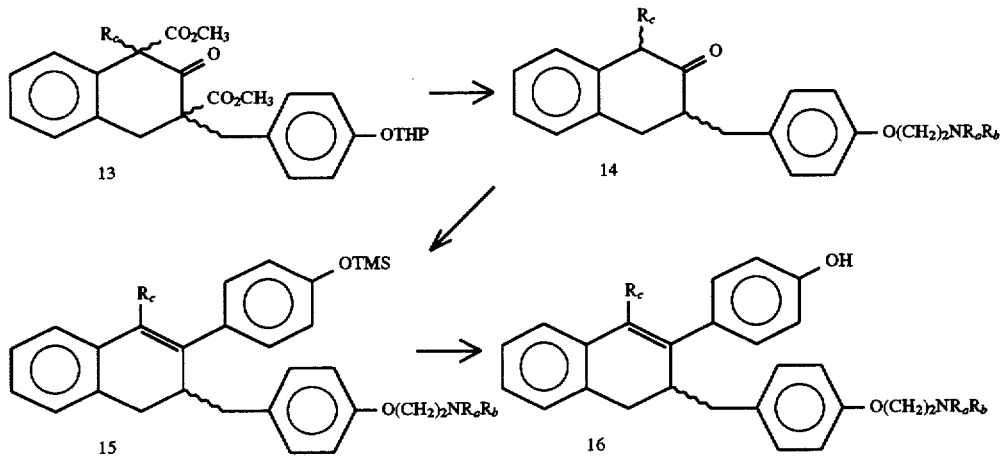

β-tetralone is alkylated with (MeO)$_2$CO and sodium hydride in THF at reflux followed the reaction of sodium hydride and RI (CH$_3$I) in THF and HMPA. The action of MeOCOCN in presence of LDA yield the compound 12 (R$_c$=CH$_3$) which is alkylated into compound 13 (R$_c$=CH$_3$) by IC$_6$H$_4$OTHP in presence of sodium hydride in THF and HMPA. The decarboalkoxylation with lithium bromide in pyridine followed by the modification of the phenol function (acidic hydrolysis and reaction with Cl (CH$_2$)$_2$ NC$_5$H$_{10}$ in presence of K$_2$CO$_3$) gives the ketone 14 (R$_a$R$_b$=C$_5$H$_{10}$) which is transformed into compound 15 (R$_a$R$_b$=C$_5$H$_{10}$) by reaction with the Grignard's reagent of Br C$_6$H$_4$OTMS in ether. The acidic hydrolysis gives the compound 16 (EM 431, R$_a$R$_b$=C$_5$H$_{10}$).

TABLE 3

[structure: naphthalene with R$_c$, phenol, O(CH$_2$)$_2$NR$_a$R$_b$]

| EM | R$_a$ | R$_b$ | R$_c$ |
|---|---|---|---|
| EM 360 | CH$_3$ | CH$_3$ | CH$_3$ |
| EM 431 | —C$_5$H$_{10}$— | | CH$_3$ |
| EM 363 | —C$_4$H$_8$— | | C$_2$H$_5$ |

EXAMPLE 31

Scheme 31

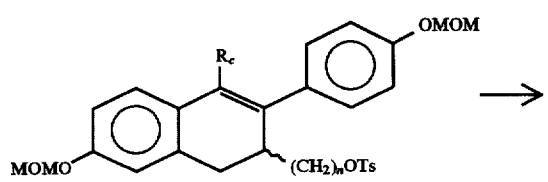

9

-continued
Scheme 31

[structure 17: MOMO-naphthalene-OMOM with (CH$_2$)$_n$NR$_a$R$_b$]

[structure 18: HO-naphthalene-OH with (CH$_2$)$_n$NR$_a$R$_b$]

The compound 17 (n=6, R$_a$R$_b$=—C$_5$H$_{10}$—, R$_c$=CH$_3$) is obtained by the reaction of HNR$_a$R$_b$ and sodium hydride on the compound 9. The acidic hydrolysis gives the compound 18 (EM 473, n=6, R$_a$R$_b$=—C$_5$H$_{10}$, R$_c$=CH$_3$).

TABLE 4

[structure: HO-naphthalene-OH with R$_c$ and (CH$_2$)$_n$NR$_a$R$_b$]

| EM | n | R$_a$ | R$_b$ | R$_c$ |
|---|---|---|---|---|
| EM 471 | 5 | CH$_3$ | CH$_3$ | CH$_3$ |
| EM 473 | 6 | —C$_5$H$_{10}$— | | CH$_3$ |
| EM 465 | 7 | —C$_4$H$_8$— | | C$_2$H$_5$ |

EXAMPLE 32

Scheme 32

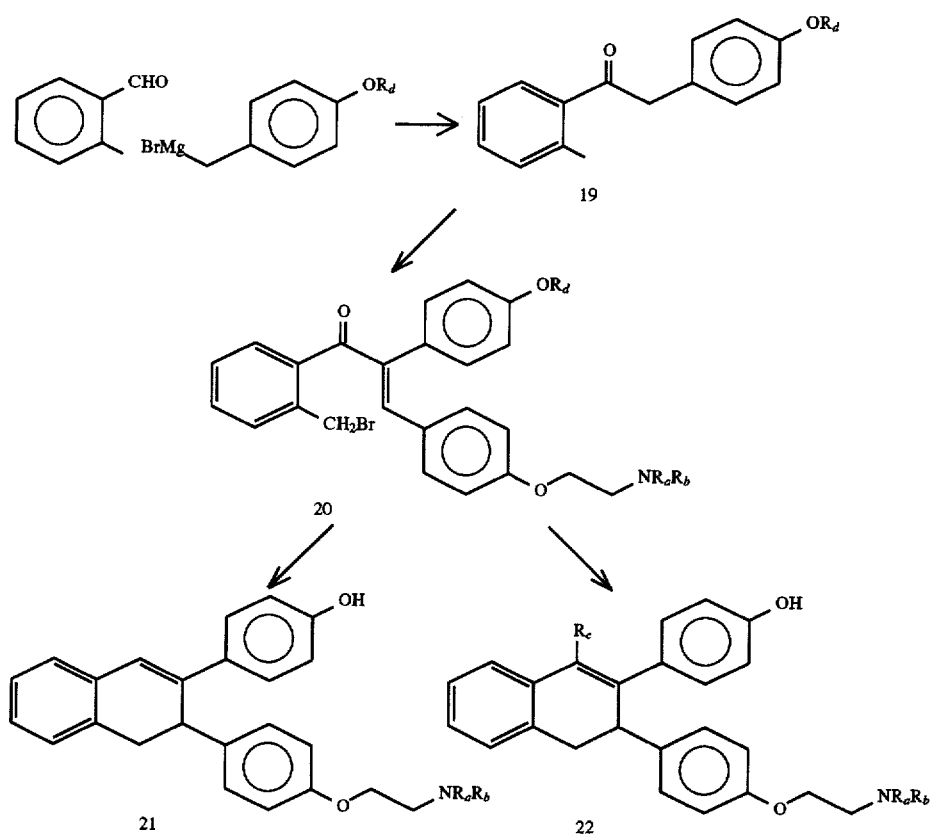

The reaction of the o-tolualdehyde with the Grignard's reagent of $BrCH_2C_6H_4OR_d$ ($CR_d$=THP) followed by the oxidation of the resulting alcohol by PCC (pyridinum chlorochromate) gave the compound 19. The reaction with $OHCC_6H_4O(CH_2)_2NC_5H_{10}$ in presence of sodium hydride followed by bromination with N-bromosuccimide on presence of light in $CCl_4$ gave the enone 20 ($R_aR_b$=—$C_5H_{10}$—). The product 21 ($R_aR_b$=—$C_5H_{10}$—) is obtained by cyclisation with (L-Bu)3SnH and AIBN (2'—2'-azobisisobutyronitrile) followed by reduction of the ketone with sodium borohydride and acidic removal of the protection and the alcohol function. The compound 22 (EM 735, $R_aR_b$=—$C_5H_{10}$—, $R_c$=$CH_3$) was obtained by cyclisation with LDA followed by Grignard's reaction with alkyl bromide and acidic removal of the protection.

TABLE 5

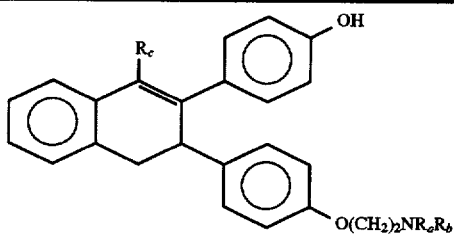

| EM | $R_a$ | $R_b$ | $R_c$ |
|---|---|---|---|
| EM 777 | $CH_3$ | $CH_3$ | $CH_3$ |
| EM 773 | $C_2H_5$ | $C_2H_5$ | $C_2H_5$ |
| EM 765 | —$C_5H_{10}$— | | $CH_3$ |
| EM 778 | —$C_4H_8$— | | $C_2H_5$ |
| EM 734 | $CH_3$ | $CH_3$ | $CH_3$ |
| EM 699 | $C_2H_5$ | $C_2H_5$ | $CH_3$ |
| EM 735 | —$C_5H_{10}$— | | $CH_3$ |
| EM 725 | —$C_4H_8$— | | $CH_3$ |
| EM 779 | $C_4H_2F_7$ | $CH_3$ | H |

EXAMPLE 33

Scheme 33

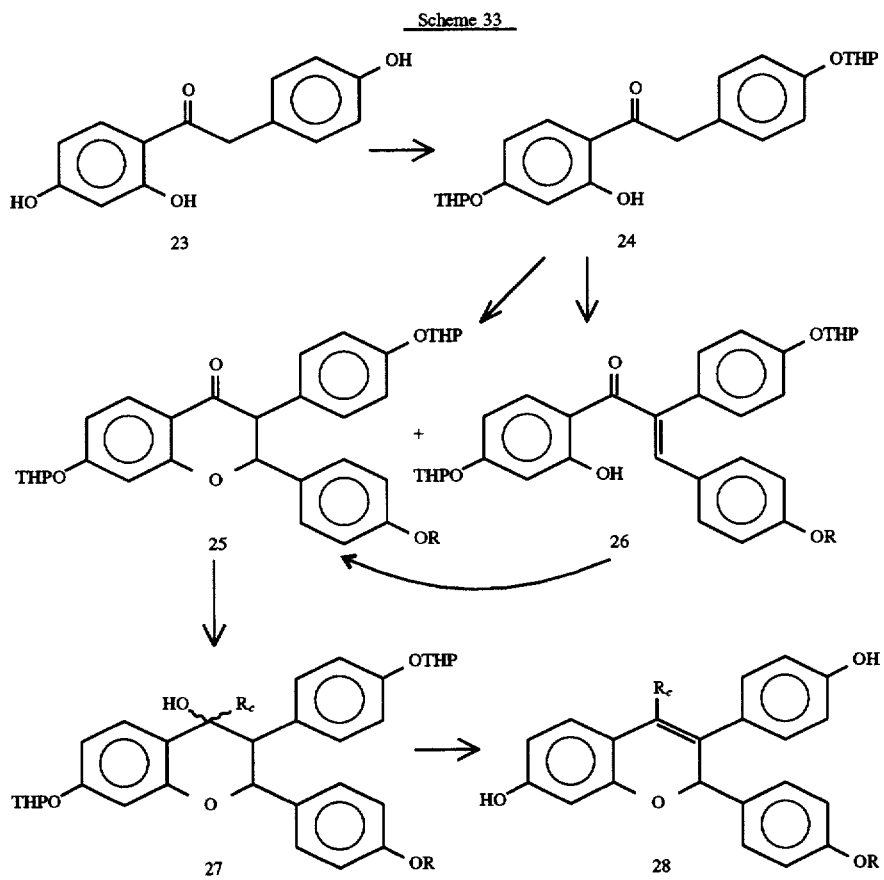

EM 349

The compound 26 (R=H, R$_c$=H) was reduced with sodium borohydride in ethanol and a mixture of resulting compound (300mg; 0.6mmol), 4-(2-chloroethyl)morpholine hydrochloride (267 mg; 1.4 mmol) cesium carbonate (978 mg; 3.0 mmol and potassium iodide (100 mg; 0.6 mmol) in N,N-dimethylformamide (10 ml) was kept at 90° C. and with stirring for 1 h. Water was added and the resulting mixture was extracted several times with a mixture of ether and ethyl acetate (1:1). Drying (MgSO$_4$) and removal of solvent gave a waxy material that was purified by chomatography on silica gel (hexanes: ethyl acetate; 3:7+a few drops of triethylamine) to yield the dehydrated derivative of the compound 27 (R=(CH$_2$)$_2$NC$_4$H$_8$O, R$_c$=H) (153 mg; 41%).

A solution of above compound(153 mg; 249μmol) in a mixture of acetic acid (60 ml) and water (6 ml) was kept at 100° C. for 10 min. The solvent was removed under reduced pressure and the residue was purified by chromatography on silica gel (ethyl acetate: acetone; 3:1) to yield compound 28 (EM-349, R=(CH$_2$)$_2$NC$_4$H$_8$O, R$_c$=H)(100 mg; 90%). (δ NMR; 300 MHz; solvent: CD$_3$OD; standard: TMS) 2.54 (4H; t; J 4.5Hz; cyclo-N-CH$_2$—CH$_2$—O—CH$_2$—CH$_2$—) 2.73 (2H; t; J 5.5Hz, O—CH$_2$—CH$_2$—N) 3.66 (4H; t; J 4.5 Hz; cyclo-N-CH$_2$—CH$_2$—O—CH$_2$—CH$_2$—) 4.04 (2H; t; J 5.5Hz; O—CH$_2$—CH$_2$—N) 6.11 CH; d; J 2.5Hz; CH Phenyl) 6.12 (1H; s; O—CH—Ph) 6.29 (1H; dd; J 2.8 Hz,8 Hz; CH Phenyl) 6.69 (2H; d; J 8.5 Hz; CH Phenyl) 6.78 (2H; d; J 8.5 Hz; CH Phenyl 6.94 (1H; d; J 8 Hz; CH Phenyl) 6.95 (1H; s; HC=C) 7.25 (2H; d; J 8.5 Hz; CH Phenyl) 7.31 (2H; d; J 8.5 Hz; CH Phenyl).

TABLE 6

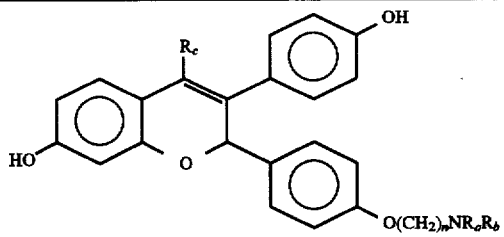

| EM | n | R$_a$ | R$_b$ | R$_c$ |
|---|---|---|---|---|
| EM 542 | 2 | CH$_3$ | CH$_3$ | CH$_3$ |
| EM 543 | 2 | —C$_4$H$_8$— | | CH$_3$ |
| EM 343 | 2 | —C$_5$H$_{10}$— | | CH$_3$ |
| EM 756 | 2 | —C$_5$H$_{10}$— | | C$_2$H$_5$ |
| EM 623 | 3 | C$_2$H$_5$ | C$_2$H$_5$ | CH$_3$ |
| EM 321 | 3 | —C$_4$H$_8$— | | CH$_3$ |
| EM 872 | 3 | —C$_5$H$_{10}$— | | C$_2$H$_5$ |
| EM 349 | 2 | —C$_4$H$_8$O— | | H |
| EM 691 | 3 | CH$_3$ | CH$_3$ | H |

EXAMPLE 34

Same synthesis as example 33 in scheme 33, the compound 23 being replaced by the 2',4-dihydroxyphenylacetophenone

TABLE 7

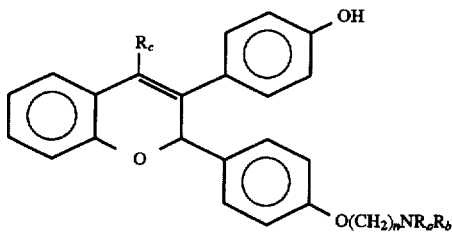

| EM | n | R$_a$ | R$_b$ | R$_c$ |
|---|---|---|---|---|
| EM 423 | 2 | —C$_5$H$_{10}$— | | C$_2$H$_5$ |
| EM 428 | 2 | —C$_4$H$_8$— | | CH$_3$ |
| EM 432 | 2 | CH$_3$ | CH$_3$ | CH$_3$ |
| EM 472 | 3 | —C$_5$H$_{10}$— | | CH$_3$ |
| EM 492 | 3 | —C$_4$H$_8$— | | C$_2$H$_5$ |

EXAMPLE 35

Same synthesis than example 33 in scheme 33, the compound 23 being replaced by the 2'-hydroxyphenylacetophenone

TABLE 8

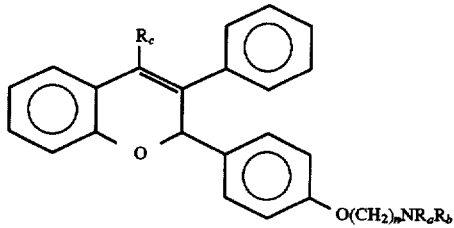

| EM | n | R$_a$ | R$_b$ | R$_c$ |
|---|---|---|---|---|
| EM 384 | 3 | —C$_5$H$_{10}$— | | CH$_3$ |
| EM 386 | 2 | CH$_3$ | CH$_3$ | CH$_3$ |
| EM 382 | 3 | CH$_3$ | CH$_3$ | C$_2$H$_5$ |

EXAMPLE 36

EM 350

Synthesis Described in Scheme 33

Thus the compound 27 (R=H, R$_c$=H) was reduced with sodium borohydride in ethanol and a mixture of resulting compound (300 mg; 0.6 mmol), chloroacetic acid, piperidylamide (242 mg; 1.5 mmol) and cesium carbonate (978 mg; 3.0 mmol) in N,N-dimethylformamide (10 ml) was kept at 90° C. and with stirring for 1 h. Water was added and the resulting mixture was extracted several times with ether. Drying (MgSO$_4$) and removal of solvent under reduced pressure gave a gummy residue that was purified by chomatography on silica gel (hexanes: ethyl acetate; 1:1) to yield compound 27 (R=CH$_2$CONC$_5$H$_{10}$, R$_c$=H) (127 mg; 34%).

A solution of above compound (127 mg; 203 μmol) in a mixture of acetic acid (10 ml) and water (1 ml) was kept at 100° C. for 10 min. The solvent was removed under reduced pressure and the residue was purified by chromatography on silica gel (ethyl acetate: hexanes; 1:1) to yield compound 28 (EM 350, R=CH$_2$CONC$_5$H$_{10}$, R$_c$=H) (43 mg; 46%). (δ NMR; 300 MHz; solvent: CD$_3$OD; standard: TMS) 1.4–1.7 (6H; m; cyclo—N—CH$_2$—CH$_2$—CH$_2$—CH$_2$—CH$_2$—) 3.40 (2H; t; J 5.5 Hz; cyclo—N—CH$_2$—CH$_2$—CH$_2$—CH$_2$—CH$_2$—) 3.49 (2H; t; J 5.5Hz; cyclo—N—CH$_2$—C$_2$—CH$_2$—CH$_2$—CH$_2$—) 4.67 (2H; s; O—CH$_2$—CO—N) 6.11 (1H; d; J 2 Hz; CH Phenyl) 6.13 (1H; s; O—CH—Ph) 6.29 (1H; dd; J 2 Hz,8 Hz; CH Phenyl) 6.69 (2H; d; J 8.5 Hz; CH Phenyl) 6.79 (2H; d; J 8.5 Hz; CH Phenyl) 6.94 (1H; d; J 8Hz; CH Phenyl) 6.95 (1H; s; HC=C) 7.25 (2H; d; J 8.5 Hz; CH Phenyl) 7.32 (2H; d; J 8.5 Hz; CH Phenyl). Mass Spectroscopy: M+457

28 (R=(CH$_2$)nCONMeBu, R$_c$=H)

All these compounds were prepared by the following procedure. However, when n was superior to 1, potassium iodide was added to the reaction mixtures during the coupling reactions.

Typical procedure 28 (EM 357, n=1)

Thus the compound 26 (R=H, R$_c$=H) was reduced with sodium borohydridee in ethanol and a mixture of resulting compound (418 mg; 0.84 mmol), N-methyl,N-butyl chloroacetamide (342 mg; 2.09 mmol) and cesium carbonate (1.36 g; 4.18 mmol in N,N-dimethylformamide (20 ml) was kept at 90° C. and with stirring for 12 h. Water was added and the resulting mixture was extracted several times with ether. Drying (MgSO$_4$) and removal of solvent under reduced pressure gave a gummy residue that was purified by chomatography on silica gel (hexanes: ethyl acetate; 1:1) to yield compound 27 (R=CH$_2$CONMeBU, R$_c$=H) (276 mg; 53%).

A solution of above compound (138 mg; 2201 μmol) in a mixture of acetic acid (10 ml) and water (1 ml) was kept at room temperature for 10 min. The solvent was removed under reduced pressure and the residue was purified by chromatography on silica gel (ethyl acetate: hexanes; 1:1) to yield compound 28 (EM 357, R=CH$_2$CONMeBu, R$_c$=H) (38 mg; 37%). (δ NMR; 300 MHz; solvent: CD$_3$OD; standard:TMS) 0.85–1.0 (3H; m; N—CH$_2$—CH$_2$—CH$_2$—CH$_3$) .1.2–1.35 (2H; m; N—CH$_2$—CH$_2$—CH$_2$—CH$_3$) 1.4–1.65 (2H; m; N—CH$_2$—CH$_2$—CH2—CH$_3$) 2.87 and 2.96 (3H; 2s; N—CH$_3$) 3.25–3.4 (2H; m; N—CH$_2$—CH$_2$—CH$_2$CH$_3$) 4.66 and 4.68 (2H; 2s; O—CH$_2$—CO—N) 6.12 (1H; d; Y 2.5 Hz; CH Phenyl) 6.13 (1H; s; O—CH—Ph) 6.29 (1H; dd; J 2.5 Hz.8 Hz; CH Phenyl) 6.70 (2H; d; J 8.5 Hz; CH Phenyl) 6.78 and 6.79 (2H; 2d; J 8.5 Hz; CH Phenyl) 6.94 (1H; d; J 8Hz; CH Phenyl) 6.95 (1H; s; HC=C) 7.25 (2H; d; J 8.5 Hz; CH Phenyl) 7.32 (2H; d; 18.5 Hz; CH Phenyl). Mass Spectroscopy: M+459

TABLE 9

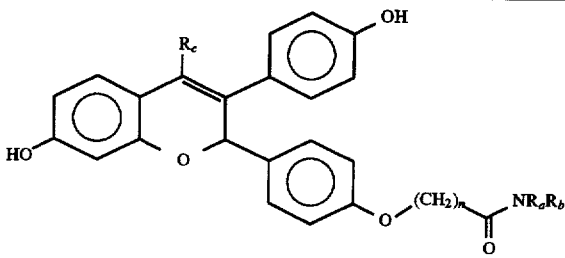

| EM | n | R$_a$ | R$_b$ | R$_c$ |
|---|---|---|---|---|
| EM 350 | 1 | —C$_5$H$_{10}$— | | H |
| EM 357 | 1 | CH$_3$ | C$_4$H$_9$ | H |
| EM 808 | 2 | CH$_3$ | C$_4$H$_9$ | H |

TABLE 9-continued

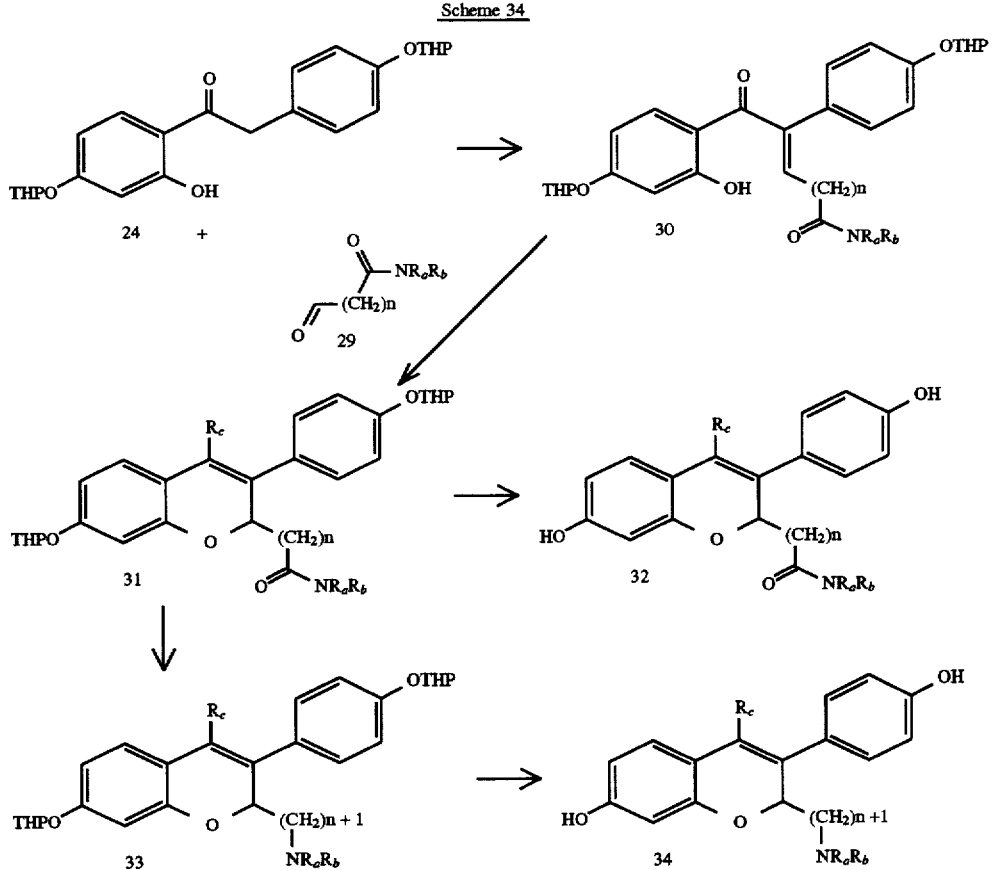

| EM | n | R$_a$ | R$_b$ | R$_c$ |
|---|---|---|---|---|
| EM 908 | 3 | CH$_3$ | C$_4$H$_9$ | H |
| EM 901 | 4 | CH$_3$ | C$_4$H$_9$ | H |

EXAMPLE 37

EM 345

Synthesis described in scheme 34

A mixture of compound 24 (2.52 g; 6.12 mmol), the aldehyde 29 (n=7, R$_a$=Me, R$_b$=Bu) (1.00g; 4.08 mmol) and piperidine (500 µl) in benzene (170 ml) was reflux for 48 h by means of a dean-stark apparatus. The solvent was removed under reduced pressure and the resulting oil was purified by chromatography on silica gel (hexanes: ethyl acetate; 7:3) to yield the chalcone 30 (n=7, R$_a$=Me, R$_b$=Bu) (620 mg; 77% corrected yield) and the unreacted starting material 24 (2.00 g).

To a solution of the chalcone 30 (n=7, R$_a$=Me, R$_b$=Bu) (469 mg; 0.73 mmol) in ethanol (30 ml) at room temperature and with stirring was slowly added sodium borohydride (34 mg; 0.89 mol). The reaction mixture was stirred for a further 12 h at room temperature. The solvent was removed under reduced pressure. The oily residue was taken in ethyl acetate and it was washed several times with saturated aqueous ammonium chloride solution. The organic extract was dried (MgSO$_4$) and solvent was removed under reduced pressure. The residue was purified by chromatography on silica gel (hexanes: ethyl acetate; 4:1) to yield the compound 31 (n=7, R$_a$=Me, R$_b$=Bu, R$_c$=H)(300 mg; 66%).

A solution of compound 31 (n=7, R$_a$=Me, R$_b$=Bu, R$_c$=H) (300 mg; 482 µmol in a mixture of acetic acid (30 ml) and water (3 ml) was kept at 100° C. for 30 min. The solvent was removed under reduced pressure and the residue was purified by chromatography on silica gel (ethyl acetate: hexanes; 1:4) to yield compound 32 (EM 345, n=7, R$_a$=Me, R$_b$=Bu, R$_c$=H) (104 mg; 48%). (δ NMR; 300 MHz; solvent: CDCl$_3$; standard: TMS) 0.85–1.0 (3H; m; N—CH$_2$—CH$_2$CH$_2$—CH$_3$).1.15–1.9 (16H; m; N—CH$_2$—CH$_2$—CH$_2$—CH$_3$ and O—CH—(CH$_2$)$_6$—CH$_2$—CO—N) 2.3–2.4 (2H; m; CH$_2$—CO—N 2.96 and 3.00 (3H; 2s; N—CH$_3$) 3.28 and 3.40 (2H; 2m; N—CH$_2$—CH$_2$—CH$_2$—CH$_3$) 5.15 (1H; dd; J 2 Hz,10 Hz; O—CH—CH$_2$) 6.44 (1H; dd; J 2 Hz, 8 Hz; CH Phenyl) 6.54 (1H; d; J 2 Hz; CH Phenyl) 6.60 (1H; S; HC=C) 6.84

(2H; d; J 8.5 Hz; CH Phenyl) 6.92 (1H; d; J 8 Hz; CH Phenyl) 7.31 (2H; d; J 8.5 Hz; CH Phenyl). Mass Spectroscopy: M+451

TABLE 10

[Structure: chromene-like with $R_c$, OH, HO, O, $(CH_2)_nCONR_aR_b$]

| EM | n | $R_a$ | $R_b$ | $R_c$ |
|---|---|---|---|---|
| EM 345 | 7 | $CH_3$ | $C_4H_9$ | H |
| EM 453 | 8 | $CH_3$ | $C_4H_2F_7$ | $CH_3$ |
| EM 358 | 9 | $CH_3$ | $C_4H_9$ | H |
| EM 467 | 10 | $CH_3$ | $C_4H_9$ | $CH_3$ |
| EM 532 | 10 | $-C_4H_8-$ | | $C_2H_5$ |

EXAMPLE 38

Typical procedure for compounds 34 (EM 371, n=10, $R_a$=Me, $R_b$=Bu, $R_c$=H) Synthesis described in scheme 34

To a solution of the amide 31 (n=10, $R_a$=Met $R_b$=Bu, $R_c$=H) (100 mg; 0.15 mmol) in tetrahydrofuran (10 ml under reflux and with stirring was added a solution of lithium aluminium hydride (1M in tetrahydrofuran; 0.42 ml; 0.42 mmol). The resulting mixture was refluxed for a further 48 h. 2N aqueous sodium hydroxide solution was added to the reaction mixture and the aqueous layer was extracted several times with ethyl acetate. The joined organic extracts were dried (MgSO$_4$) and solvent was removed under reduced pressure. The residue was purified by chromatography on silica gel (hexanes: acetone; 1:1) to yield the amine 33 (n=10, $R_a$=Me, $R_b$=Bu, $R_c$=H) (60 mg; 62%).

A solution of above compound (60 mg; 93μmol) and pyridinium p-toluenesulfonate (46 mg; 185 μmol in methanol (10 ml) was refluxed for 12 h. The solvent was removed under reduced pressure and the residue was purified by chromatography on silica gel (hexanes: acetone; 3:2) to yield the chromene 34 (EM 371, n=10, $R_a$=Me, $R_b$=Bu, $R_c$=H) (30 mg; 67%) (B NMR; 300MHz; solvent: CD$_3$OD; standard: TMS)0.93 (3H; t; 17.5 Hz; N—CH$_2$—CH$_2$—CH$_2$—CH$_3$).1.15–1.85 (24H; m; N—CH$_2$—CH$_2$—CH$_2$—CH$_3$ and O—CH—(CH$_2$)$_{10}$—CH$_2$—N) 2.24 (3H; s; N—CH$_3$) 2.35–2.45 (4H; m; CH$_2$—N—CH$_2$) 5.19 (1H; dd; J 2.5 Hz,10 Hz; O—CH—CH$_2$) 6.26 (1H; d; J 2.5 Hz; CH Phenyl) 6.33 (1H; dd; J 2.5 Hz,8.5 Hz; CH Phenyl) 6.59 (1H; s; HC—C) 6.78 (2H; d; J 8.5 Hz; CH Phenyl) 6.88 (1H; d; J 8 Hz; CH Phenyl) 7.30 (2H; d; J 8.5 Hz; CH Phenyl).

TABLE 11

[Structure: chromene with $R_c$, OH, HO, O, $(CH_2)_nNR_aR_b$]

| EM | n | $R_a$ | $R_b$ | $R_c$ |
|---|---|---|---|---|
| EM 631 | 5 | $-C_4H_8-$ | | $CH_3$ |
| EM 721 | 6 | $-C_5H_{10}-$ | | $CH_3$ |
| EM 371 | 10 | $CH_3$ | $C_4H_9$ | H |
| EM 612 | 7 | $C_2H_5$ | $C_2H_5$ | $C_2H_5$ |

EXAMPLE 39

Same synthesis as described in scheme 34 but the compound 29 is replaced by OHC(CH$_2$)nSORa and the reduction step was eliminated.

TABLE 12

[Structure: chromene with $R_c$, OH, HO, O, $(CH_2)_nSOR_a$]

| EM | n | $R_a$ | $R_c$ |
|---|---|---|---|
| EM 511 | 9 | $C_5H_6F_5$ | H |
| EM 513 | 10 | $C_4H_{10}$ | $CH_3$ |

EXAMPLE 40

Scheme 35

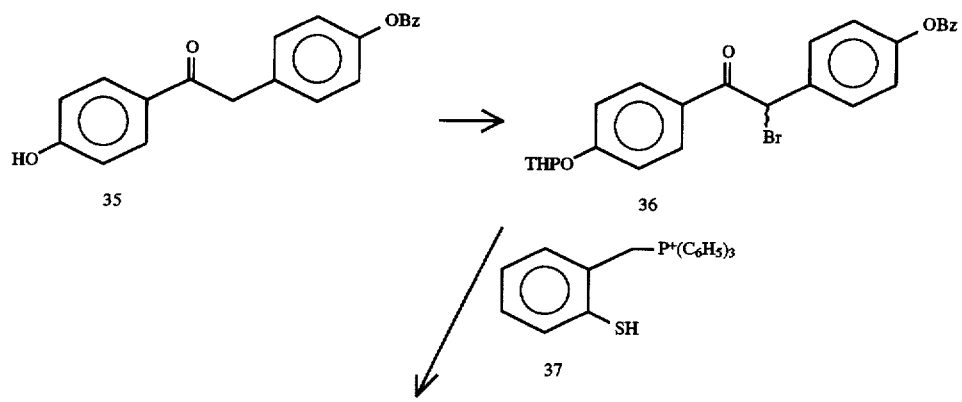

-continued
Scheme 35

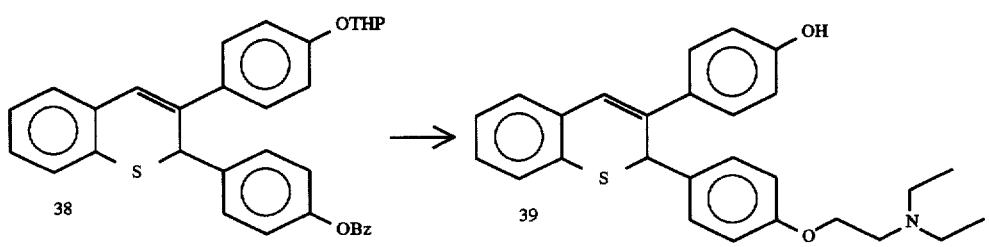

4'-hydroxy-2-(4-benzoyloxyphenyl) acetophenone as prepared from the commercial desoxyanisoïn (250 g)(hydrolysis of the methoxyl group with pyridine-HCl at 220° C. followed by the treatment with 120 ml of benzoyl chloride and 20 g of dimethylaminopyridine in 2 l of methylene chloride during 24 h) is bromined as usual manner with bromine in acetic acid at room temperature and the residue was without purification treated overnight with dihydropyran (150 ml and p-toluenesulfonic acid (10 g) in 2 l of methylene chloride at 0° C. The bromo-compound a6 is isolated (170 g) after flash chromatography on silica gel in using ethyl acetate/hexane mixture containing 0.1% triethylamine. This compound is treated for 10 min at room temperature with sodium methylate in methanol followed with 2-mercaptobenzyl triphenyl phosphonium salt a7 (obtained from reduced commercial thiosalicylic acid and triphenyl phosphine). The resulting mixture was heated at reflux for 3 h with sodium methylate in methanol and the compound 38 (95 g) is isolated after ether extraction and flash chromatography on silica gel with ethyl acetate/hexane mixture containing 0.1% triethylamine. The benzyl protection is hydrolysed with sodium carbonate in methanol-water solution at room temperature and a mixture of resulting compound, N,N, diethyl chloroethylamine HCl and cesium carbonate in N,N-dimethylformamide (20 ml) is kept at 90° C. and with stirring for 12 h, extracted several times with ether. Drying (MgSO$_4$) and removal of solvent under reduced pressure gives a gummy residue that is purified by chomatography on silica gel (hexanes: ethyl acetate; 1:1). The resulting compound in methanol (2 l is heated at reflux with p-toluenesulfonic acid (5 g) for 3 h. Extraction with ethyl acetate and flash chromatography with silica gel (hexanes: ethyl acetate) gives the compound 39 (EM 547) (68 g) of which structure was determined by spectroscopic means.

TABLE 13

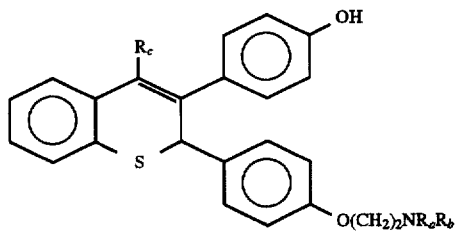

| EM | $R_a$ | $R_b$ | $R_c$ |
|---|---|---|---|
| EM 560 | —$C_5H_{10}$— | | H |
| EM 635 | —$C_4H_8$— | | $CH_3$ |
| EM 547 | $C_2H_5$ | $C_2H_5$ | H |

EXAMPLE 41

Same synthesis than the synthesis described in scheme 35 except the starting compound 35 is HOC$_6$H$_4$CO(CH$_2$)nCONR$_a$R$_b$

TABLE 14

![structure]

| EM | n | R$_a$ | R$_b$ | R$_c$ |
|---|---|---|---|---|
| EM 541 | 5 | CH$_3$ | C$_4$H$_9$ | H |
| EM 634 | 7 | CH$_3$ | C$_4$H$_9$ | CH$_3$ |
| EM 563 | 8 | CH$_3$ | C$_4$H$_9$ | H |
| EM 762 | 9 | CH$_3$ | C$_4$H$_9$ | H |
| EM 941 | 10 | —C$_4$H$_8$— | | CH$_3$ |

The compound 40 obtained by acylation and methylation of the commercial m-anisidine is treated in a Friedel-Craft reaction with the 4-methoxyphenylacetoyl chloride 41 and AlCl$_3$. A mixture of resulted compound 42, the aldehyde 43 (R=THP) and piperidine in benzene is refluxed for 48 h by means of a dean-stark apparatus. The solvent is removed under reduced pressure and the resulting oil is purified by chromatography on silica gel. The condensed compound 44 is transformed into compound 45 by alkalin treatment (KOH in methanol) and the protecting group R is replaced by (CH$_2$)$_2$NC$_5$H$_{10}$ by the method described in example 33. The resulting compound 45 is treated with methylmagnesium iodide in THF followed by pyridine-HCl treatment to give compound 46 (EM 821, R$_a$R$_b$=C$_5$H$_{10}$, R$_c$=CH$_3$).

EXAMPLE 42

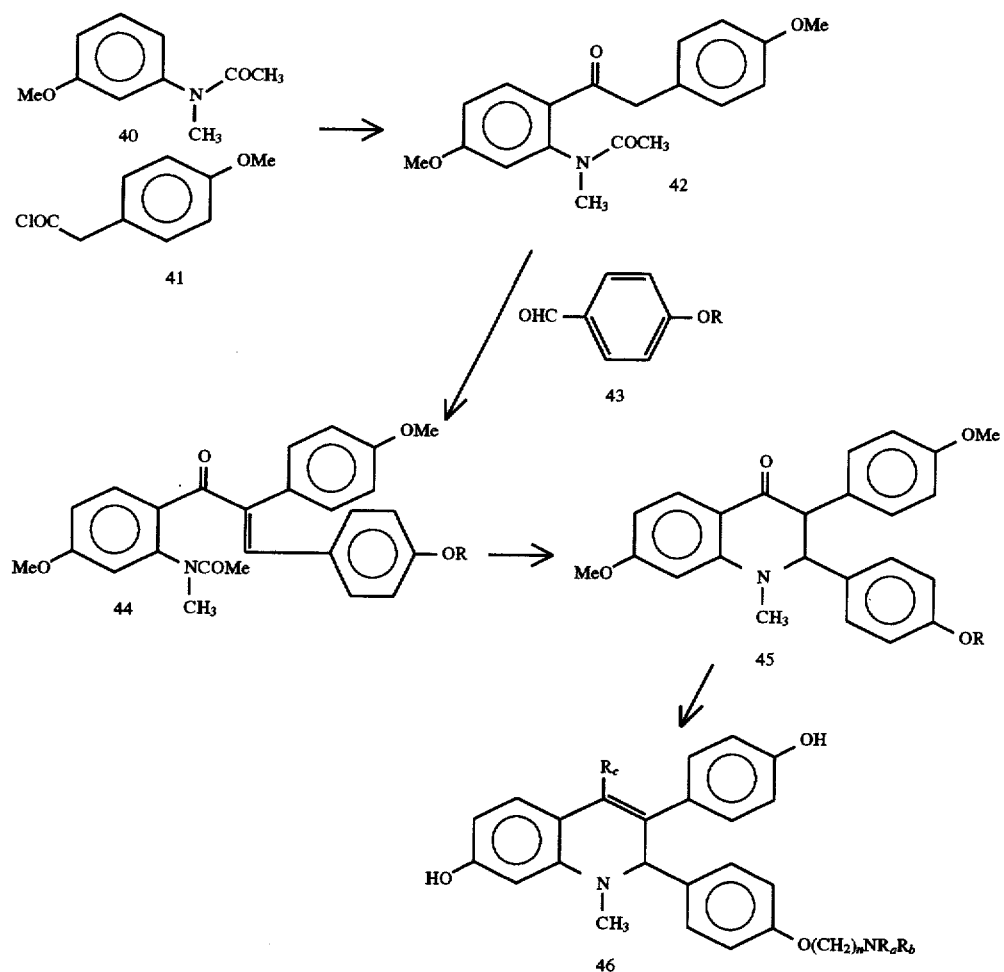

Scheme 36

TABLE 15

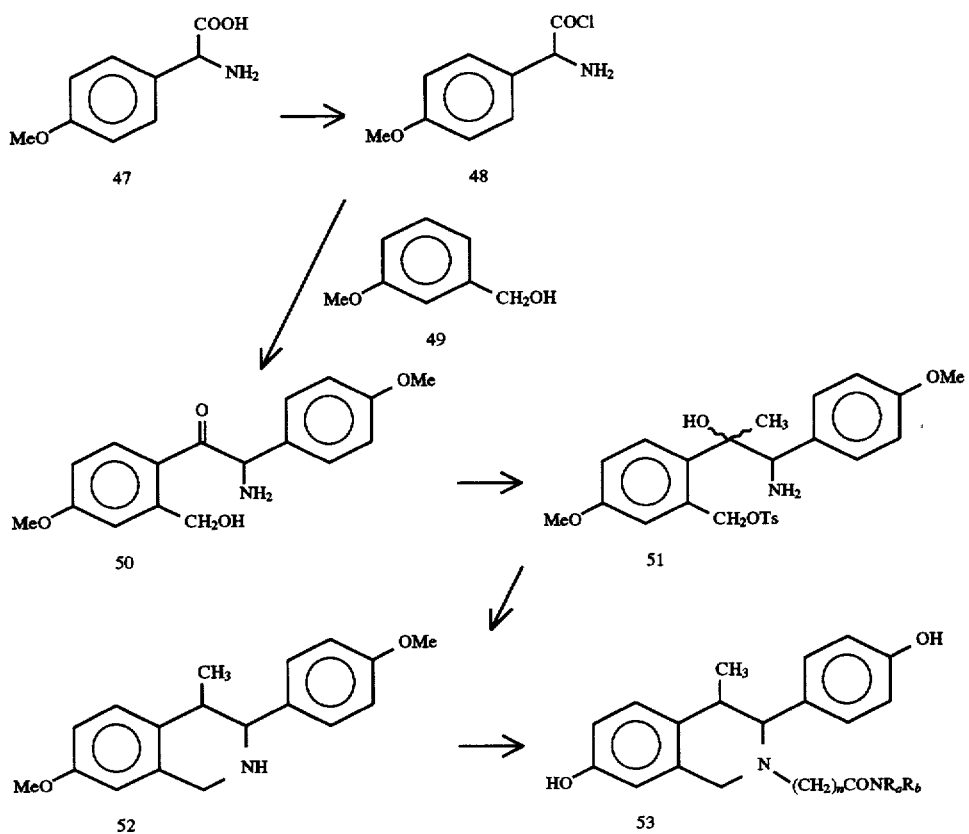

| EM | n | R_a | R_b | R_c |
|---|---|---|---|---|
| EM 821 | 2 | —C$_5$H$_{10}$— | | H |
| EM 753 | 2 | C$_2$H$_5$ | C$_2$H$_5$ | CH$_3$ |
| EM 637 | 3 | —C$_4$H$_8$— | | CH$_3$ |

TABLE 16

| EM | n | R_a | R_b | R_c |
|---|---|---|---|---|
| EM 865 | 6 | CH$_3$ | C$_4$H$_9$ | CH$_3$ |
| EM 876 | 9 | CH$_3$ | C$_4$H$_9$ | CH$_3$ |
| EM 877 | 10 | —C$_4$H$_8$— | | H |

EXAMPLE 44

Same synthesis than the synthesis described in scheme 37. The compound 53 is reduced with LiAlH$_4$ in THF.

EXAMPLE 43

Scheme 37

The 4-methoxyphenylglycine 47 (prepared from commercial 4-hydroxyphenylglycine) is treated with (COCl)$_2$. The resulting acid chloride 48 is used in a Friedel-Craft reaction on the 3-methoxybenzyl alcohol 49 in using aluminiumchloride as catalyst. The coupled compound 50 is treated with methyl magnesium iodide in THF followed by the treatment with p-toluenesulfonylchloride in pyridine and CH$_2$Cl$_2$ and dimethylaminopyridine. The resulting compound 51 is heated and reduced with LiAlH$_4$ into the compound 52. The alkylation with NaH and Br(CH$_2$)$_{10}$CONC$_4$H$_8$ in DMF gives the compound 53 (EM 877, R$_a$R$_b$=C$_4$H$_8$).

TABLE 17

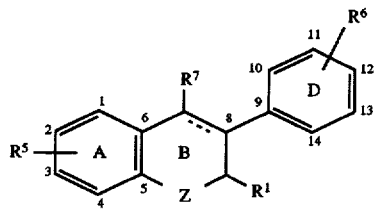

| EM | n | R_a | R_b | R_c |
|---|---|---|---|---|
| EM 626 | 5 | —$C_5H_{10}$— | | H |
| EM 628 | 6 | —$C_4H_8$— | | $CH_3$ |
| EM 605 | 7 | $CH_3$ | $CH_3$ | $CH_3$ |

The terms and descriptions used herein are preferred embodiments set forth by way of illustration only, and are not intended as limitations on the many variations which those of skill in the art will recognize to be possible in practicing the present invention as defined by the claims.

What is claimed is:

1. A compound whose molecular structure is:

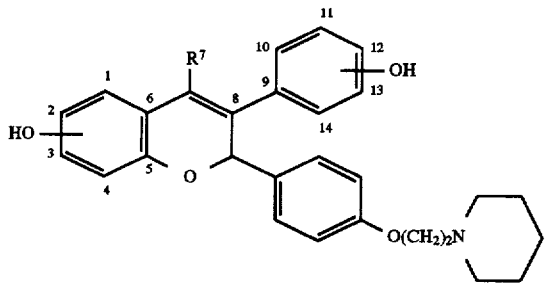

wherein the dotted line is an optional pi bond and Z is —O—, —NH—, —S— or —$CH_2$—;

wherein $R^5$ and $R^6$ are independently selected from the group consisting of hydrogen, hydroxyl and a moiety convertible in vivo to hydroxyl and are not simultaneously hydrogen and are not simultaneously at position 3 and position 12;

wherein $R^7$ is methyl, ethyl, propyl ethenyl or ethynyl; and wherein $R^1$ is selected from the group consisting of —$(CH_2)_{10}CONCH_3C_4H_9$, —$(CH_2)_6NC_5H_{10}$, —$(CH_2)_9 SOC_5H_6F_5$, and $\phi$—O—$(CH_2)_2NC_5H_{10}$.

2. The compound of claim 1, wherein Z is —O—.

3. A pharmaceutical composition comprising a pharmaceutically acceptable diluent or carrier and a therapeutically effective amount of the compound of claim 1.

4. The pharmaceutical composition of claim 3, wherein Z is —O—.

5. The pharmaceutical composition of claim 3 wherein said compound has the molecular structure:

wherein $R^7$ is methyl, ethyl, propyl, ethenyl or ethynyl and wherein the hydroxyl groups are not simultaneously at position 3 and position 12.

* * * * *